(12) United States Patent
Franklin et al.

(10) Patent No.: US 9,044,298 B2
(45) Date of Patent: Jun. 2, 2015

(54) SELF-ADJUSTING GASTRIC BAND

(75) Inventors: Ethan Franklin, Goleta, CA (US); Sean Snow, Carpinteria, CA (US); Erik Torjesen, Goleta, CA (US); Justin J. Schwab, Santa Barbara, CA (US); Zachary P. Dominguez, Santa Barbara, CA (US)

(73) Assignee: APOLLO ENDOSURGERY, INC., Austin, TX (US)

( * ) Notice: Subject to any disclaimer, the term of this patent is extended or adjusted under 35 U.S.C. 154(b) by 213 days.

(21) Appl. No.: 13/216,132

(22) Filed: Aug. 23, 2011

(65) Prior Publication Data

US 2012/0088962 A1   Apr. 12, 2012

Related U.S. Application Data

(63) Continuation-in-part of application No. 13/149,585, filed on May 31, 2011, now abandoned, and a continuation-in-part of application No. 13/049,453, filed on Mar. 16, 2011, now abandoned, said (Continued)

(51) Int. Cl.
*A61F 2/00* (2006.01)
*A61F 13/00* (2006.01)
*A61F 5/00* (2006.01)

(52) U.S. Cl.
CPC .................................. *A61F 5/0056* (2013.01)

(58) Field of Classification Search
CPC ..... A61F 5/005; A61F 5/0053; A61F 5/0056; A61F 5/0059; A61F 5/0063
USPC ............................. 600/37; 606/151, 153, 157
See application file for complete search history.

(56) References Cited

U.S. PATENT DOCUMENTS

| 1,174,814 A | 3/1916 | Brennan et al. |
| 1,830,947 A | 11/1931 | Klingel |

(Continued)

FOREIGN PATENT DOCUMENTS

| CA | 949965 | 6/1974 |
| CN | 1250382 | 4/2000 |

(Continued)

OTHER PUBLICATIONS

Brown et al; "Symmetrical Pouch Dilation After Laparoscopic Adjustable Gastric Banding: Incidence and Management"; Obesity Surgery; V. 18, pp. 1104-1108; 2008.

(Continued)

*Primary Examiner* — Jacqueline Cheng
*Assistant Examiner* — Eileen Hyde
(74) *Attorney, Agent, or Firm* — Gordon & Jacobson, PC

(57) ABSTRACT

Generally described herein are automatic, self-adjusting, gastric banding systems and improvements thereof, that are capable of automatically relaxing and contracting in response to a large bolus passing through the area of a patient's stomach constricted by a gastric band. Alternatively, and/or in addition in one or more embodiments, the gastric banding systems described herein may also help prevent pouch dilatation and/or erosion. The apparatus and systems described herein aid in facilitating obesity control and/or treating obesity-related diseases while generally being non-invasive once implanted. Furthermore, certain embodiments of the self-adjusting gastric banding systems disclosed herein are automatically adjustable without complicated fluid control mechanisms, flow rate limiting devices, and/or valves. The automatic adjustments may also be made in response to other changes in the patient's esophageal-gastric junction, for example, in response to size, shape, and or location changes.

7 Claims, 34 Drawing Sheets

Related U.S. Application Data application No. 13/149,585 is a continuation-in-part of application No. 12/770,617, filed on Apr. 29, 2010, now abandoned, said application No. 13/049,453 is a continuation-in-part of application No. 12/770,617, filed on Apr. 29, 2010.

(56) References Cited

U.S. PATENT DOCUMENTS

| | | |
|---|---|---|
| 1,999,683 A | 4/1935 | Borresen |
| 2,163,048 A | 6/1939 | McKee |
| 2,339,138 A | 1/1944 | Black |
| 2,405,667 A | 8/1946 | Ottesen |
| 2,438,231 A | 3/1948 | Schultz et al. |
| 2,635,907 A | 4/1953 | Heimbuch |
| 2,714,469 A | 8/1955 | Carlson |
| 2,936,980 A | 5/1960 | Rapata |
| 3,059,645 A | 10/1962 | Hasbrouck et al. |
| 3,189,961 A | 6/1965 | Heller |
| 3,667,081 A | 6/1972 | Burger |
| 3,840,018 A | 10/1974 | Heifetz |
| 3,955,834 A | 5/1976 | Ahlrot |
| 4,053,176 A | 10/1977 | Hilbush |
| 4,118,805 A | 10/1978 | Reimels |
| 4,133,315 A | 1/1979 | Berman et al. |
| 4,157,713 A | 6/1979 | Clarey |
| 4,176,412 A | 12/1979 | Peterson |
| 4,236,521 A | 12/1980 | Lauterjung |
| 4,271,827 A | 6/1981 | Angelchick |
| 4,299,012 A | 11/1981 | Oetiker |
| 4,340,083 A | 7/1982 | Cummins |
| 4,399,809 A | 8/1983 | Baro et al. |
| 4,408,597 A | 10/1983 | Tenney, Jr. et al. |
| 4,417,567 A | 11/1983 | Trick |
| 4,424,208 A | 1/1984 | Wallace et al. |
| 4,442,153 A | 4/1984 | Meltsch |
| 4,450,375 A | 5/1984 | Siegal |
| 4,485,805 A | 12/1984 | Foster, Jr. |
| 4,492,004 A | 1/1985 | Oetiker |
| 4,551,862 A | 11/1985 | Haber |
| 4,558,699 A | 12/1985 | Bashour |
| 4,559,699 A | 12/1985 | Owen et al. |
| 4,582,640 A | 4/1986 | Smestad et al. |
| 4,582,865 A | 4/1986 | Balazs et al. |
| 4,592,339 A | 6/1986 | Kuzmak et al. |
| 4,592,355 A | 6/1986 | Antebi |
| 4,601,713 A | 7/1986 | Fuqua |
| 4,667,672 A | 5/1987 | Romanowski |
| 4,671,351 A | 6/1987 | Rappe |
| 4,693,695 A | 9/1987 | Cheng |
| 4,694,827 A | 9/1987 | Weiner et al. |
| 4,696,288 A | 9/1987 | Kuzmak et al. |
| 4,708,140 A | 11/1987 | Baron |
| 4,716,154 A | 12/1987 | Malson et al. |
| 4,753,086 A | 6/1988 | Schmidt |
| 4,760,837 A | 8/1988 | Petit |
| 4,803,075 A | 2/1989 | Wallace et al. |
| 4,881,939 A | 11/1989 | Newman |
| 4,883,467 A | 11/1989 | Franetzki et al. |
| 4,886,787 A | 12/1989 | de Belder et al. |
| 4,896,787 A | 1/1990 | Delamour et al. |
| 4,915,690 A | 4/1990 | Cone et al. |
| 4,925,446 A | 5/1990 | Garay et al. |
| 4,944,487 A | 7/1990 | Holtermann |
| 4,944,659 A | 7/1990 | Labbe et al. |
| 4,958,791 A | 9/1990 | Nakamura |
| 4,969,899 A | 11/1990 | Cox, Jr. |
| 4,994,019 A | 2/1991 | Fernandez et al. |
| 5,045,060 A | 9/1991 | Melsky et al. |
| 5,074,868 A | 12/1991 | Kuzmak |
| 5,084,061 A | 1/1992 | Gau et al. |
| 5,091,171 A | 2/1992 | Yu et al. |
| 5,116,652 A | 5/1992 | Alzner |
| 5,120,313 A | 6/1992 | Elftman |
| 5,143,724 A | 9/1992 | Leshchiner et al. |
| 5,152,770 A | 10/1992 | Bengmark et al. |
| 5,160,338 A | 11/1992 | Vincent |
| 5,188,609 A | 2/1993 | Bayless et al. |
| 5,224,494 A | 7/1993 | Enhorning |
| 5,226,429 A | 7/1993 | Kuzmak |
| 5,246,456 A | 9/1993 | Wilkinson |
| 5,246,698 A | 9/1993 | Leshchiner et al. |
| 5,259,399 A | 11/1993 | Brown |
| 5,326,349 A | 7/1994 | Baraff |
| 5,343,894 A | 9/1994 | Frisch et al. |
| 5,356,883 A | 10/1994 | Kuo et al. |
| 5,360,445 A | 11/1994 | Goldowsky |
| 5,391,156 A | 2/1995 | Hildwein et al. |
| 5,399,351 A | 3/1995 | Leshchiner et al. |
| 5,449,363 A | 9/1995 | Brust et al. |
| 5,449,368 A | 9/1995 | Kuzmak |
| 5,458,568 A | 10/1995 | Racchini et al. |
| 5,509,888 A | 4/1996 | Miller |
| 5,531,716 A | 7/1996 | Luzio et al. |
| 5,535,752 A | 7/1996 | Halperin et al. |
| 5,554,113 A | 9/1996 | Novak et al. |
| 5,562,714 A | 10/1996 | Grevious |
| 5,601,604 A | 2/1997 | Vincent |
| 5,607,418 A | 3/1997 | Arzbaecher |
| 5,633,001 A | 5/1997 | Agerup |
| 5,653,718 A | 8/1997 | Yoon |
| 5,658,298 A | 8/1997 | Vincent et al. |
| 5,676,162 A | 10/1997 | Larson, Jr. et al. |
| 5,695,504 A | 12/1997 | Gifford, III et al. |
| 5,704,893 A | 1/1998 | Timm |
| 5,713,911 A | 2/1998 | Racenet et al. |
| 5,733,257 A | 3/1998 | Sternby |
| 5,748,200 A | 5/1998 | Funahashi |
| 5,766,232 A | 6/1998 | Grevious et al. |
| 5,769,877 A | 6/1998 | Barreras, Sr. |
| 5,785,295 A | 7/1998 | Tsai |
| 5,817,113 A | 10/1998 | Gifford, III et al. |
| 5,827,529 A | 10/1998 | Ono et al. |
| 5,833,698 A | 11/1998 | Hinchliffe et al. |
| 5,861,014 A | 1/1999 | Familoni |
| RE36,176 E | 3/1999 | Kuzmak |
| 5,886,042 A | 3/1999 | Yu et al. |
| 5,904,697 A | 5/1999 | Gifford, III et al. |
| 5,910,149 A | 6/1999 | Kuzmak |
| 5,928,195 A | 7/1999 | Malamud et al. |
| 5,938,669 A | 8/1999 | Klaiber et al. |
| 5,944,696 A | 8/1999 | Bayless et al. |
| 5,944,751 A | 8/1999 | Laub |
| 5,993,473 A | 11/1999 | Chan et al. |
| 6,013,679 A | 1/2000 | Kuo et al. |
| 6,024,340 A | 2/2000 | Lazarus et al. |
| 6,024,704 A | 2/2000 | Meador et al. |
| 6,048,309 A | 4/2000 | Flom et al. |
| 6,067,991 A | 5/2000 | Forsell |
| 6,074,341 A | 6/2000 | Anderson et al. |
| 6,074,378 A | 6/2000 | Mouri et al. |
| 6,083,249 A | 7/2000 | Familoni |
| 6,090,131 A | 7/2000 | Daley |
| 6,102,678 A | 8/2000 | Peclat |
| 6,102,922 A | 8/2000 | Jakobsson et al. |
| 6,171,321 B1 | 1/2001 | Gifford, III et al. |
| 6,193,734 B1 | 2/2001 | Bolduc et al. |
| 6,203,523 B1 | 3/2001 | Haller et al. |
| 6,210,345 B1 | 4/2001 | Van Brunt |
| 6,210,347 B1 | 4/2001 | Forsell |
| 6,221,024 B1 | 4/2001 | Miesel |
| 6,224,857 B1 | 5/2001 | Romeo et al. |
| 6,306,088 B1 | 10/2001 | Krausman et al. |
| 6,327,503 B1 | 12/2001 | Familoni |
| 6,371,965 B2 | 4/2002 | Gifford, III et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,387,105 B1 | 5/2002 | Gifford, III et al. |
| 6,417,750 B1 | 7/2002 | Shon |
| 6,418,934 B1 | 7/2002 | Chin |
| 6,419,696 B1 | 7/2002 | Ortiz et al. |
| 6,432,040 B1 | 8/2002 | Meah |
| 6,439,539 B1 | 8/2002 | Powell |

(56) References Cited

U.S. PATENT DOCUMENTS

| | | |
|---|---|---|
| 6,443,957 B1 | 9/2002 | Addis |
| 6,443,965 B1 | 9/2002 | Gifford, III et al. |
| 6,450,173 B1 | 9/2002 | Forsell |
| 6,450,946 B1 | 9/2002 | Forsell |
| 6,451,034 B1 | 9/2002 | Gifford, III et al. |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyos Garza |
| 6,457,801 B1 | 10/2002 | Fish et al. |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,474,584 B2 | 11/2002 | Ekich |
| 6,475,136 B1 | 11/2002 | Forsell |
| 6,485,496 B1 | 11/2002 | Suyker et al. |
| 6,491,704 B2 | 12/2002 | Gifford, III et al. |
| 6,491,705 B2 | 12/2002 | Gifford, III et al. |
| 6,511,490 B2 | 1/2003 | Robert |
| 6,517,556 B1 | 2/2003 | Monassevitch |
| 6,527,701 B1 | 3/2003 | Sayet et al. |
| 6,547,801 B1 | 4/2003 | Dargent et al. |
| 6,565,582 B2 | 5/2003 | Gifford, III et al. |
| 6,579,301 B1 | 6/2003 | Bales et al. |
| 6,601,604 B1 | 8/2003 | Cooper |
| 6,615,084 B1 | 9/2003 | Cigaina |
| 6,627,620 B1 | 9/2003 | Nielsen |
| 6,630,486 B1 | 10/2003 | Royer |
| 6,632,239 B2 | 10/2003 | Snyder et al. |
| 6,646,628 B2 | 11/2003 | Shirochi et al. |
| 6,676,674 B1 | 1/2004 | Dudai |
| 6,685,668 B1 | 2/2004 | Cho et al. |
| 6,685,963 B1 | 2/2004 | Taupin et al. |
| 6,691,047 B1 | 2/2004 | Fredricks |
| 6,715,731 B1 | 4/2004 | Post et al. |
| 6,729,600 B2 | 5/2004 | Mattes et al. |
| 6,754,527 B2 | 6/2004 | Stroebel et al. |
| 6,767,924 B2 | 7/2004 | Yu et al. |
| 6,811,136 B2 | 11/2004 | Eberhardt et al. |
| 6,820,651 B2 | 11/2004 | Seuret et al. |
| 6,834,201 B2 | 12/2004 | Gillies et al. |
| 6,871,090 B1 | 3/2005 | He et al. |
| 6,889,086 B2 | 5/2005 | Mass et al. |
| 6,916,326 B2 | 7/2005 | Benchetrit |
| 6,921,819 B2 | 7/2005 | Piron et al. |
| 6,924,273 B2 | 8/2005 | Pierce |
| 6,940,467 B2 | 9/2005 | Fisher et al. |
| 6,966,875 B1 | 11/2005 | Longobardi |
| 7,017,583 B2 | 3/2006 | Forsell |
| 7,021,147 B1 | 4/2006 | Subramanian et al. |
| 7,037,344 B2 | 5/2006 | Kagan et al. |
| 7,040,349 B2 | 5/2006 | Moler et al. |
| 7,054,690 B2 | 5/2006 | Imran |
| 7,058,434 B2 | 6/2006 | Wang et al. |
| 7,060,080 B2 | 6/2006 | Bachmann |
| 7,118,526 B2 | 10/2006 | Egle |
| 7,119,062 B1 | 10/2006 | Alvis et al. |
| 7,128,750 B1 | 10/2006 | Stergiopulos |
| 7,144,400 B2 | 12/2006 | Byrum et al. |
| 7,172,607 B2 | 2/2007 | Hofle et al. |
| 7,177,693 B2 | 2/2007 | Starkebsum |
| 7,191,007 B2 | 3/2007 | Desai et al. |
| 7,204,821 B1 | 4/2007 | Clare et al. |
| 7,223,239 B2 | 5/2007 | Schulze et al. |
| 7,238,191 B2 | 7/2007 | Bachmann |
| 7,240,607 B2 | 7/2007 | Fish |
| 7,255,675 B2 | 8/2007 | Gertner et al. |
| 7,263,405 B2 | 8/2007 | Boveja et al. |
| 7,282,023 B2 | 10/2007 | Frering |
| 7,288,064 B2 | 10/2007 | Boustani et al. |
| 7,297,103 B2 | 11/2007 | Jarsaillon et al. |
| 7,299,082 B2 | 11/2007 | Feldman et al. |
| 7,310,557 B2 | 12/2007 | Maschino et al. |
| 7,311,716 B2 | 12/2007 | Byrun |
| 7,311,717 B2 | 12/2007 | Egle |
| 7,314,443 B2 | 1/2008 | Jordan et al. |
| 7,314,636 B2 | 1/2008 | Caseres et al. |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,364,542 B2 | 4/2008 | Jambor et al. |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,457,668 B2 | 11/2008 | Cancel et al. |
| 7,481,763 B2 | 1/2009 | Hassler, Jr. et al. |
| 7,500,944 B2 | 3/2009 | Byrum et al. |
| 7,502,649 B2 | 3/2009 | Ben-Haim et al. |
| 7,530,943 B2 | 5/2009 | Lechner |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,670,279 B2 | 3/2010 | Gertner |
| 7,699,770 B2 | 4/2010 | Hassler, Jr. et al. |
| 7,712,470 B2 | 5/2010 | Gertner |
| 7,727,141 B2 | 6/2010 | Hassler, Jr. et al. |
| 7,741,476 B2 | 6/2010 | Lebreton |
| 7,758,493 B2 | 7/2010 | Gingras |
| 7,763,039 B2 | 7/2010 | Ortiz et al. |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,775,967 B2 | 8/2010 | Gertner |
| 7,794,386 B2 | 9/2010 | Brooks |
| 7,811,298 B2 | 10/2010 | Birk |
| 7,824,422 B2 | 11/2010 | Benchetrit |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos, Jr. et al. |
| 7,862,502 B2 | 1/2011 | Pool et al. |
| 7,879,068 B2 | 2/2011 | Dlugos et al. |
| 7,951,067 B2 | 5/2011 | Byrum et al. |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0098097 A1 | 7/2002 | Singh |
| 2002/0139208 A1 | 10/2002 | Yatskov |
| 2002/0183765 A1 | 12/2002 | Adams |
| 2002/0193679 A1 | 12/2002 | Malave et al. |
| 2002/0198548 A1 | 12/2002 | Robert |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0060873 A1 | 3/2003 | Gertner et al. |
| 2003/0066536 A1 | 4/2003 | Forsell |
| 2003/0073880 A1 | 4/2003 | Polsky et al. |
| 2003/0093157 A1 | 5/2003 | Casares et al. |
| 2003/0100910 A1 | 5/2003 | Gifford, III et al. |
| 2003/0120288 A1 | 6/2003 | Benchetrit |
| 2003/0148995 A1 | 8/2003 | Piron et al. |
| 2003/0158564 A1 | 8/2003 | Benchetrit |
| 2003/0158569 A1 | 8/2003 | Wazne |
| 2003/0181890 A1 | 9/2003 | Schulze et al. |
| 2003/0181917 A1 | 9/2003 | Gertner |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0049209 A1 | 3/2004 | Benchetrit |

(56) References Cited

U.S. PATENT DOCUMENTS

| | | |
|---|---|---|
| 2004/0059393 A1 | 3/2004 | Policker et al. |
| 2004/0064110 A1 | 4/2004 | Forsell |
| 2004/0068847 A1 | 4/2004 | Belisle et al. |
| 2004/0106899 A1 | 6/2004 | McMichael et al. |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |
| 2005/0038498 A1 | 2/2005 | Dubrow et al. |
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0082793 A1 | 4/2005 | Lee |
| 2005/0100779 A1 | 5/2005 | Gertner |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Knudson et al. |
| 2005/0136122 A1 | 6/2005 | Sadozai et al. |
| 2005/0142152 A1 | 6/2005 | Leshchiner et al. |
| 2005/0143765 A1 | 6/2005 | Bachmann et al. |
| 2005/0143766 A1 | 6/2005 | Bachmann et al. |
| 2005/0154274 A1 | 7/2005 | Jarsaillon et al. |
| 2005/0171568 A1 | 8/2005 | Duffy |
| 2005/0183730 A1 | 8/2005 | Byrum |
| 2005/0192531 A1 | 9/2005 | Birk |
| 2005/0192601 A1 | 9/2005 | Demarais |
| 2005/0192629 A1 | 9/2005 | Saadat et al. |
| 2005/0216042 A1 | 9/2005 | Gertner |
| 2005/0227936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neill |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler, Jr. |
| 2005/0267500 A1 | 12/2005 | Hassler, Jr. |
| 2005/0267533 A1 | 12/2005 | Gertner |
| 2005/0271729 A1 | 12/2005 | Wang |
| 2005/0277899 A1 | 12/2005 | Conlon et al. |
| 2005/0283041 A1 | 12/2005 | Egle |
| 2005/0288739 A1 | 12/2005 | Hassler, Jr. et al. |
| 2005/0288740 A1 | 12/2005 | Hassler, Jr. et al. |
| 2006/0015138 A1 | 1/2006 | Gertner |
| 2006/0020298 A1 | 1/2006 | Camilleri et al. |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0122147 A1 | 6/2006 | Wohlrab |
| 2006/0142700 A1 | 6/2006 | Sobelman et al. |
| 2006/0142790 A1 | 6/2006 | Gertner |
| 2006/0161139 A1 | 7/2006 | Levine et al. |
| 2006/0161186 A1 | 7/2006 | Hassler, Jr. et al. |
| 2006/0167531 A1 | 7/2006 | Gertner et al. |
| 2006/0173238 A1 | 8/2006 | Starkebaum |
| 2006/0173424 A1 | 8/2006 | Conlon |
| 2006/0183967 A1 | 8/2006 | Lechner |
| 2006/0189887 A1 | 8/2006 | Hassler, Jr. et al. |
| 2006/0189888 A1 | 8/2006 | Hassler, Jr. et al. |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212051 A1 | 9/2006 | Snyder et al. |
| 2006/0212053 A1 | 9/2006 | Gertner |
| 2006/0229696 A1 | 10/2006 | Boustani |
| 2006/0235448 A1 | 10/2006 | Roslin et al. |
| 2006/0246137 A1 | 11/2006 | Hermitte et al. |
| 2006/0247721 A1 | 11/2006 | Maschino et al. |
| 2006/0247722 A1 | 11/2006 | Maschino et al. |
| 2006/0252982 A1 | 11/2006 | Hassler, Jr. |
| 2006/0252983 A1 | 11/2006 | Lembo et al. |
| 2006/0257488 A1 | 11/2006 | Hubbard |
| 2006/0264699 A1 | 11/2006 | Gertner |
| 2006/0276812 A1 | 12/2006 | Hill et al. |
| 2006/0293627 A1 | 12/2006 | Byrum et al. |
| 2007/0015954 A1 | 1/2007 | Dlugos |
| 2007/0015955 A1 | 1/2007 | Tsonton |
| 2007/0015956 A1 | 1/2007 | Crawford et al. |
| 2007/0016231 A1 | 1/2007 | Jambor et al. |
| 2007/0016262 A1 | 1/2007 | Gross et al. |
| 2007/0027356 A1 | 2/2007 | Ortiz |
| 2007/0027358 A1 | 2/2007 | Gertner et al. |
| 2007/0044655 A1 | 3/2007 | Fish |
| 2007/0077292 A1 | 4/2007 | Pinsky |
| 2007/0078476 A1 | 4/2007 | Hull, Sr. et al. |
| 2007/0125826 A1 | 6/2007 | Shelton |
| 2007/0156013 A1 | 7/2007 | Birk |
| 2007/0167672 A1 | 7/2007 | Dlugos et al. |
| 2007/0167982 A1 | 7/2007 | Gertner et al. |
| 2007/0173685 A1 | 7/2007 | Jambor et al. |
| 2007/0173888 A1 | 7/2007 | Gertner et al. |
| 2007/0179335 A1 | 8/2007 | Gertner et al. |
| 2007/0185373 A1 | 8/2007 | Tsonton |
| 2007/0185462 A1 | 8/2007 | Byrum |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann et al. |
| 2007/0250086 A1 | 10/2007 | Wiley et al. |
| 2007/0255335 A1 | 11/2007 | Herbert et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2007/0265646 A1 | 11/2007 | McCoy et al. |
| 2007/0293716 A1 | 12/2007 | Baker et al. |
| 2007/0298005 A1 | 12/2007 | Thibault |
| 2008/0009680 A1 | 1/2008 | Hassler, Jr. |
| 2008/0015406 A1 | 1/2008 | Dlugos et al. |
| 2008/0015501 A1 | 1/2008 | Gertner |
| 2008/0027269 A1 | 1/2008 | Gertner |
| 2008/0027469 A1 | 1/2008 | Bachmann |
| 2008/0071306 A1 | 3/2008 | Gertner |
| 2008/0097496 A1 | 4/2008 | Chang et al. |
| 2008/0108862 A1 | 5/2008 | Jordan et al. |
| 2008/0147002 A1 | 6/2008 | Gertner |
| 2008/0161717 A1 | 7/2008 | Gertner |
| 2008/0161875 A1 | 7/2008 | Stone |
| 2008/0167647 A1 | 7/2008 | Gertner |
| 2008/0167648 A1 | 7/2008 | Gertner |
| 2008/0172072 A1 | 7/2008 | Pool et al. |
| 2008/0188766 A1 | 8/2008 | Gertner |
| 2008/0195092 A1 | 8/2008 | Kim et al. |
| 2008/0208240 A1 | 8/2008 | Paz |
| 2008/0221598 A1 | 9/2008 | Dlugos et al. |
| 2008/0243071 A1 | 10/2008 | Quijano et al. |
| 2008/0249806 A1 | 10/2008 | Dlugos et al. |

(56) References Cited

U.S. PATENT DOCUMENTS

| | | |
|---|---|---|
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0300618 A1 | 12/2008 | Gertner |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0187202 A1 | 7/2009 | Ortiz et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0216256 A1* | 8/2009 | Nicholson, IV ............ 606/157 |
| 2009/0220176 A1 | 9/2009 | Fusco |
| 2009/0222031 A1 | 9/2009 | Axelsson |
| 2009/0222065 A1 | 9/2009 | Dlugos, Jr. et al. |
| 2009/0228063 A1 | 9/2009 | Dlugos, Jr. et al. |
| 2009/0228072 A1 | 9/2009 | Coe et al. |
| 2009/0270904 A1 | 10/2009 | Birk et al. |
| 2009/0306462 A1 | 12/2009 | Lechner |
| 2010/0010291 A1 | 1/2010 | Birk et al. |
| 2010/0049224 A1 | 2/2010 | Vargas |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0106617 A1 | 4/2010 | Snow |
| 2010/0145378 A1 | 6/2010 | Gertner |
| 2010/0152532 A1 | 6/2010 | Marcotte |
| 2010/0168508 A1 | 7/2010 | Gertner |
| 2010/0185049 A1 | 7/2010 | Birk et al. |
| 2010/0191265 A1 | 7/2010 | Lau et al. |
| 2010/0191271 A1 | 7/2010 | Lau et al. |
| 2010/0204647 A1 | 8/2010 | Gertner |
| 2010/0204723 A1 | 8/2010 | Gertner |
| 2010/0217071 A1 | 8/2010 | Ricol |
| 2010/0226988 A1 | 9/2010 | Lebreton |
| 2010/0228080 A1 | 9/2010 | Tavori et al. |
| 2010/0234682 A1 | 9/2010 | Gertner |
| 2010/0249803 A1 | 9/2010 | Griffiths |
| 2010/0280310 A1 | 11/2010 | Raven |
| 2010/0305397 A1 | 12/2010 | Birk et al. |
| 2010/0312046 A1 | 12/2010 | Lau et al. |
| 2010/0312147 A1 | 12/2010 | Gertner |
| 2010/0324358 A1 | 12/2010 | Birk et al. |
| 2010/0324359 A1 | 12/2010 | Birk |
| 2011/0071341 A1 | 3/2011 | Dlugos |
| 2011/0201874 A1 | 8/2011 | Birk et al. |

FOREIGN PATENT DOCUMENTS

| | | |
|---|---|---|
| CN | 1367670 | 9/2002 |
| DE | 10020688 | 12/2000 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 | 9/2000 |
| EP | 1072282 | 1/2001 |
| EP | 1105073 | 6/2001 |
| EP | 1396242 | 3/2004 |
| EP | 1396243 | 3/2004 |
| EP | 1491167 | 12/2004 |
| EP | 1491168 | 12/2004 |
| EP | 1529502 | 5/2005 |
| EP | 1547549 | 6/2005 |
| EP | 1574189 | 9/2005 |
| EP | 1600183 | 11/2005 |
| EP | 1602346 | 12/2005 |
| EP | 1704833 | 9/2006 |
| EP | 1719480 | 11/2006 |
| EP | 1736123 | 12/2006 |
| EP | 1736195 | 12/2006 |
| EP | 1736202 | 12/2006 |
| EP | 1743605 | 1/2007 |
| EP | 1829504 | 9/2007 |
| EP | 1829505 | 9/2007 |
| EP | 1829506 | 9/2007 |
| EP | 1967168 | 9/2008 |
| EP | 1992315 | 11/2008 |
| EP | 2074970 | 7/2009 |
| EP | 2074971 | 7/2009 |
| EP | 2074972 | 7/2009 |
| EP | 2095796 | 9/2009 |
| EP | 2095798 | 9/2009 |
| EP | 2191796 | 6/2010 |
| FR | 2688693 | 9/1993 |
| FR | 2769491 | 4/1999 |
| FR | 2783153 | 3/2000 |
| FR | 2797181 | 2/2001 |
| FR | 2799118 | 4/2001 |
| FR | 2823663 | 10/2002 |
| FR | 2921822 | 4/2009 |
| GB | 1174814 | 12/1969 |
| GB | 2090747 | 7/1982 |
| JP | 57-171676 | 10/1982 |
| JP | 2-019147 | 1/1990 |
| JP | 11-244395 | 9/1999 |
| JP | 2003/526410 | 9/2003 |
| JP | 2005/131380 | 5/2005 |
| JP | 2005-334658 | 12/2005 |
| WO | WO 86/00079 | 1/1986 |
| WO | WO 86/00912 | 2/1986 |
| WO | WO 89/11701 | 11/1989 |
| WO | WO 90/00369 | 1/1990 |
| WO | WO 92/20349 | 11/1992 |
| WO | WO 94/02517 | 2/1994 |
| WO | WO 96/33751 | 1/1996 |
| WO | WO 98/35639 | 8/1998 |
| WO | WO 98/35640 | 8/1998 |
| WO | WO 00/00108 | 1/2000 |
| WO | WO 00/01428 | 1/2000 |
| WO | WO 00/09047 | 2/2000 |
| WO | WO 00/09049 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/41671 | 6/2001 |
| WO | WO 01/47435 | 7/2001 |
| WO | WO 01/47575 | 7/2001 |
| WO | WO 01/49245 | 7/2001 |
| WO | WO 01/52777 | 7/2001 |
| WO | WO 01/68007 | 9/2001 |
| WO | WO 01/85071 | 11/2001 |
| WO | WO 02/05753 | 1/2002 |
| WO | WO 02/09792 | 2/2002 |

(56) References Cited

FOREIGN PATENT DOCUMENTS

| WO | WO 02/19953 | 3/2002 |
|---|---|---|
| WO | WO 02/26317 | 4/2002 |
| WO | WO 02/053093 | 7/2002 |
| WO | WO 02/065948 | 8/2002 |
| WO | WO 02/096326 | 12/2002 |
| WO | WO 03/007782 | 1/2003 |
| WO | WO 03/055420 | 7/2003 |
| WO | WO 03/057092 | 7/2003 |
| WO | WO 03/059215 | 7/2003 |
| WO | WO 03/077191 | 9/2003 |
| WO | WO 03/101352 | 12/2003 |
| WO | WO 03/105732 | 12/2003 |
| WO | WO 2004/014245 | 2/2004 |
| WO | WO 2004/019671 | 3/2004 |
| WO | WO 2004/108025 | 12/2004 |
| WO | WO 2004/112563 | 12/2004 |
| WO | WO 2005/007232 | 1/2005 |
| WO | WO 2005/009305 | 2/2005 |
| WO | WO 2005/067994 | 7/2005 |
| WO | WO 2005/072195 | 8/2005 |
| WO | WO 2005/087147 | 9/2005 |
| WO | WO 2005/094447 | 10/2005 |
| WO | WO 2005/112888 | 12/2005 |
| WO | WO 2006/040647 | 4/2006 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | 2008058028 A2 | 5/2008 |
| WO | WO 2008/063673 | 5/2008 |
| WO | WO 2008/134755 | 11/2008 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.

Dixon et al.; "Pregnancy After Lap-Band Surgery: Management of the Band to Achieve Healthy Weight Outcomes"; Obesity Surgery; V. 11, pp. 59-65; 2001.

Neary et al.; "Peptide YY(3-36) and Glucagon-Like Peptide-1($_{7-36}$) Inhibit Food Intake Additively"; Endocrinology; V.146; pp. 5120-5127; 2005.

Padidela et al.; "Elevated basal and post-feed glucagon-like petide 1 (GLP-1) concentrations in the neonatel period"; European Journal of Endocrinology; v. 160; pp. 53-58; 2009.

Shi et al.; "Sexually Dimorphic Responses to Fat Loss After Caloric Restriction or Surgical Lipectomy"; Am. J. Physiol. Endocrinol. Metab.; V. 293; E316-E326; 2007.

The Lap-Band Device & How it Works; http://lapband.com/en/learn_about-lapband/device_how_it_works/.

Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.

Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.

Adrian et al.; "Mechanism of Pancreatic Polypeptide Release in Man." The Lancet; pp. 161-163; Jan. 22, 1977.

Anson; "Shape Memory Alloys—Medical Applications," Source: Materials World, vol. 7, No. 12, pp. 745-747, Dec. 1999.

Asakawa et al; "Antagonism of Ghrelin Receptor Reduces Food Intake and Body Weight Gain in Mice"; Gut.; V.52; pp. 947-952; 2003.

Baggio et al. "Biology of Incretins: GLP-1 and GIP"; Gastroenrology; V. 132; pp. 2131-2157; 2007.

Ballantyne; "Peptide YY(1-36) and Peptide YY(3-36): Part I. Distribution, Release, and Actions"; Obesity Surgery; V.16; pp. 651-658; 2006.

Ballantyne; "Peptide YY(1-36) and Peptide YY(3-36): Part II. Changes after Gastrointestinal Surgery and Bariatric Surgery"; Obesity Surgery; V.16; pp. 795-803; 2006.

Berne et al; "Physiology"; V. 5; pp. 55-57, 210, 428, 540, 554, 579, 584, 591; 2004.

BioEnterics Lap-Band Adjustable Gastric Banding System, Inamed Health, pub., pp. 1-115; Aug. 28, 2003.

Boulant et al.; "Cholecystokinin in Transient Lower Oesophageal Sphincter Relaxation Due to Gastric Distension in Humans"; Gut.; V. 40; pp. 575-581; 1997.

Bradjewin et al.; "Dose Ranging Study of the Effects of Cholecystokinin in Healthy Volunteers"; J. Psychiatr. Neurosci.; V. 16 (2); pp. 91-95; 1991.

Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.

Chaptini et al.; "Neuroendocrine Regulation of Food Intake"; Current Opinion in Gastroenterology; V. 24; pp. 223-229; 2008.

Chaudhri; "Can Gut Hormones Control Appetite and Prevent Obesity?" Diabetes Care; V. 31; Supp 2; pp. S284-S289; Feb. 2008.

Cohen et al.; "Oxyntomodulin Suppresses Appetite and Reduces Food Intake in Humans"; J. Clin. Endocrinol. Metab.; V. 88; No. 10; pp. 4696-4701; 2003.

Corno et al.; "A new implantable device for telemetric control of pulmonary blood flow"; New ideas; received Apr. 24, 2004; received in revised form Jul. 12, 2002; 10 pages.

Corno et al.; "FlowWatchTM in clipped and inclipped position"; Interact Cardio Vase Thorac Surg 2002; 1:46-49; Copyright @ 2002 The European Association for Cardio-thoracic Surgery; 1 page.

Cummings et al.; "Plasma Ghrelin Levels After Diet-Induced Weight Loss or Gastric Bypass Sugery"; N. Engl J. Med; V. 346, No. 21; pp. 1623-1630; May 23, 2002.

Cummings; "Gastrointestinal Regulation of Foot Intake"; The Food Journal of Clinical Investigation; V. 117, N. 1; pp. 13-23; Jan. 2007.

Dakin et al.; "Oxyntomodulin Inhibits Food Intake in the Rat"; Endocrinology; V. 142; No. 10; pp. 4244-4250; 2001.

Dakin et al.; "Peripheral Oxyntomodulin Reduces Food Intake and Body Weight gain in Rats"; Endocrinology; V. 145; No. 6; pp. 2687-2695; Jun. 2004.

Davison; "Activation of Vagal-Gastric Mechanoreceptors by Cholecystokinin"; Proc. West. Pharmocol. Soc.; V. 29; pp. 363-366; 1986.

De Waele et al.; "Endoscopic vol. Adjustment of Intragastric Balloons for Intolerance"; Obesity Surgery; V. 11; pp. 223-224; 2001.

De Waele et al.; "Intragastric Balloons for Preoperative Weight Reduction"; Obesity Surgery; V. 58; pp. 58-60; 2001.

Desai et al.; "Molecular Weight of Heparin Using 13C Nuclear Magnetic Resonance Spectroscopy" Journal of Pharmaceutical Science, V. 84, I 2; 1995, Abstract only.

Doldi et al.; "Intragastric Balloon: Another Option for Treatment of Obesity and Morbid Obesity"; Hepato-Gastroenterology; V. 51, N. 55; pp. 294-307; Jan.-Feb. 2004.

Doldi et al.; "Treatment of Morbid Obesity with Intragastric Balloon in Association with Diet"; Obesity Surgery; V. 10, pp. 583-587; 2000.

Doldi et al; "Intragastric Balloon in Obese Patients"; Obesity Surgery; V. 10, 578-581; 2000.

Ekblad et al.; "Distribution of Pancreatic Peptide and Peptide-YY"; Peptides; V. 23; pp. 251-261; 2002.

El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.

Galloro et al; "Preliminary Endoscopic Technical Report of an New Silicone Intragastric Balloon in the Treatment of Morbid Obesity"; Obesity Surgery; V. 9, pp. 68-71; 1999.

(56) References Cited

OTHER PUBLICATIONS

GinShiCel MH Hydroxy Propyl Methyl Cellulose, Web Page http://www.ginshicel.cn/MHPC.html, Nov. 12, 2008.
Girard; "The incretins: From the concept to their use in the treatment of type 2 diabetes. Part A: Incretins: Concept and physiological functions"; Diabetes and Metabolism; V. 34; pp. 550-559; 2008.
Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.
Grise et al.; "Peptide YY Inhibits Growth of Human Breast Cancer in Vitro and in Vivo"; Journal of Surgical Research; V. 82; pp. 151-155; 1999.
Grundy; "Signaling the State of the Digestive Tract"; Autonomic Neuroscience: Basic and Clinical; V. 125; pp. 76-80; 2006.
Grundy; "Vagal Control of Gastrointestinal Function"; Bailliere's Clinical Gastroenterology; V. 2; No. 1; pp. 23-43; 1988.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Hameed et al.; "Gut hormones and appetite control." Oral Diseases; V. 15; pp. 18-26; 2009.
Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.
Hodson et al. "Management of Obesity with the New Intragastric Balloon"; Obesity Surgery; V. 11, pp. 327-329, 2001.
Holzer; "Gastrointestinal Afferents as Targets of Novel Drugs for the Treatment of Functional Bowel Disorders and Visceral Pain"; European Journal of Pharmacology; V. 429; pp. 177-193; 2001.
Houpt; "Gastrointestinal Factors in Hunger and Satiety." Neuroscience and Behavioral Reviews; V. 6; pp. 145-164; 1982.
Jones; "Molecular, pharmacological, and clinical aspects of liraglutide, a oncedaily human GLP-1 analogue"; Molecular and Cellular Endocrinology; V. 297; pp. 137-140; 2009.
Kerem et al.; "Exogenous Ghrelin Enhances Endocrine and Exocrine Regeneration in Pancreatectomized Rats"; J Gastrointest Surg.; V.13; pp. 775-783, 2009.
Kesty et al.; "Hormone-based therapies in the regulation of fuel metabolism and body weight"; Expert Opin. Biol. Ther.; V. 8; No. 11; pp. 1733-1747; 2008.
Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.
Kojima et al.; "A role for pancreatic polypeptide in feeding and body weight regulation." Peptides; V. 28; pp. 459-463; 2007.
Kulicke et al. "Visco-Elastic Propeerties of Sodium Hyaluronate Solutions," American Institute of Physics; pp. 585-587; 2008.
Lap-Band AP System Adjustable Gastric Banding System With OmniformTM Design: Directions for Use (DFU); Allergan, 16 pages; 2009.
Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.
Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.
Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.
Mathus-Vliegen et al. "Treating Morbid and Supermorbid Obesity" International Journal of Gastroenterology; V. 5, No. 1, pp. 9-12; 2000.

Medeiros et al.; "Processing and metabolism of Peptide-YY: Pivotal roles of Dipeptidase-IV, Aminopeptidase-P, and Endopeptidase-24. 11"; Endocrinology; V. 134, No. 5; pp. 2088-2094; 1994.
Naslund et al. "Pranidal subcutaneous injections of glucagon-like peptide-1 cause weight loss in obese human subjects"; British Journal of Nutrition; V. 91; pp. 439-446; 2004.
Potier et al.; "Protein, amino acids, and the control of food intake"; Current Opinion in Clinical Nutrition and Metabolic Care; V. 12; pp. 54-58; 2009.
Qjan et al.; "Pulmonary delivery of a GLP-1 receptor agonist, BMS-686117"; International Journal of Pharmaceutics; V. 366; pp. 218-220; 2008.
Rang et al.; "Pharmacology"; V. 5; pp. 203, 397, 402, 524; 2004.
Raybould et al.; "Integration of Postprandial Gastrointestinal Tract: Role of CCK and Sensory Pathways"; Annals of New York Academy of Science; pp. 143-156; 1994.
Renshaw et al. "Peptide YY: A Potential Therapy for Obesity"; Current Drug Targets; V. 6; pp. 171-179; 2005.
Sannino et al.; "Crosslinking of Cellulose Derivatives and Hyaluronic Acid with Water-Soluble Carbodiimide" Polymer 46; pp. 11206-11212; 2005.
Shechter et al.; "Reversible PEGylation of peptide YY3-36 prolongs its inhibition of food intake in mice"; FEBS Letters; V. 579; pp. 2439-2444; 2005.
Silver et al.; "Physical Properties of Hyaluronic Acid and Hydroxypropylmethylcellulose in Solution: Evaluation of Coating Abillity" Journal of Applied Biomaterials, V. 5; pp. 89-98, 1994.
Small et al.; "Gut hormones and the control of appetite"; TRENDS in Endocrinology and Metabolism; V. 15. No. 6; pp. 259-263; Aug. 2004.
Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.
Tezel; "The Science of Hyaluronic Acid Dermal Fillers," Journal of Cosmetic and Laser Therapy (2008) 10: pp. 35-42.
Tolhurst et al.; "Nutritional regulation of glucagon-like peptidel secretion"; J. Physiol.; V. 587, No. 1; pp. 27-32; 2009.
Totte et al.; "Weight Reduction by Means of Intragastric Device: Experience with the Bioenterics Intragastric Balloon"; Obesity Surgery; V. 11, pp. 519-523; 2001.
Tough et al.; "$Y_4$ Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.
Tseng et al; "Peptide YY and cancer: Current findings and potential clinical applications"; Peptides; V. 23; pp. 389-395; 2002.
Valassi et al.; "Neuroendocrine control of food intake"; Nut. Metab. & Cariovasc. Disease; V. 18; pp. 158-168; 2008.
Van Der Lely et al.; "Biological, Physiological, Pathophysiological Aspects of Ghrelin"; Endocrine Reviews; V. 25, No. 3; pp. 426-457; 2004.
Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; Sep. 2001.
Wahlen et al.; "The BioEnterics Intragastric Balloon (BIB): How to Use It"; Obesity Surgery; V. 11; pp. 524-527; 2001.
Wang et al.; "Plasma Ghrelin Modulation in Gastric Band Operation and Sleeve Gastrectomy"; Obes. Surg.; pp. 357-362; 2008.
Weiner et al.; "Preparation of Extremely Obese Patients for Laparoscopic Gastric Banding by Gastric Balloon Therapy"; Obesity Surgery; V. 9, pp. 261-264, 1999.
Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.
Yuzuriha et al.; "Gastrointestinal Hormones (anorexigenic peptide YY and orexigenic ghrelin) influence neural tube development"; FASEB J.; V. 21; pp. 2108-2112; 2007.

* cited by examiner

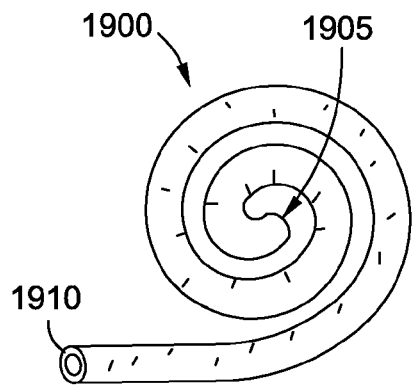
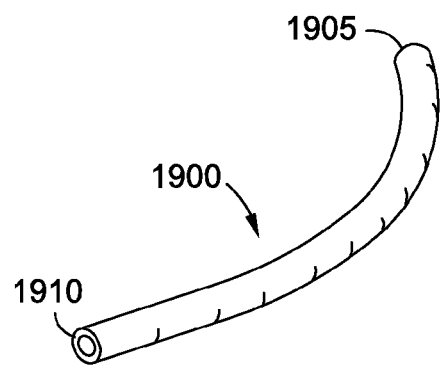
FIG. 19A  FIG. 19B
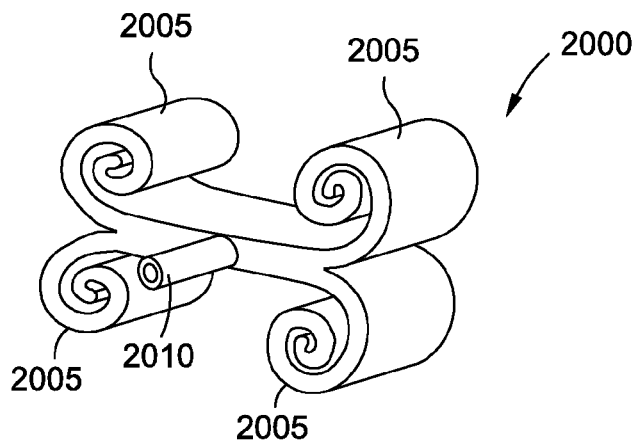
FIG. 20A
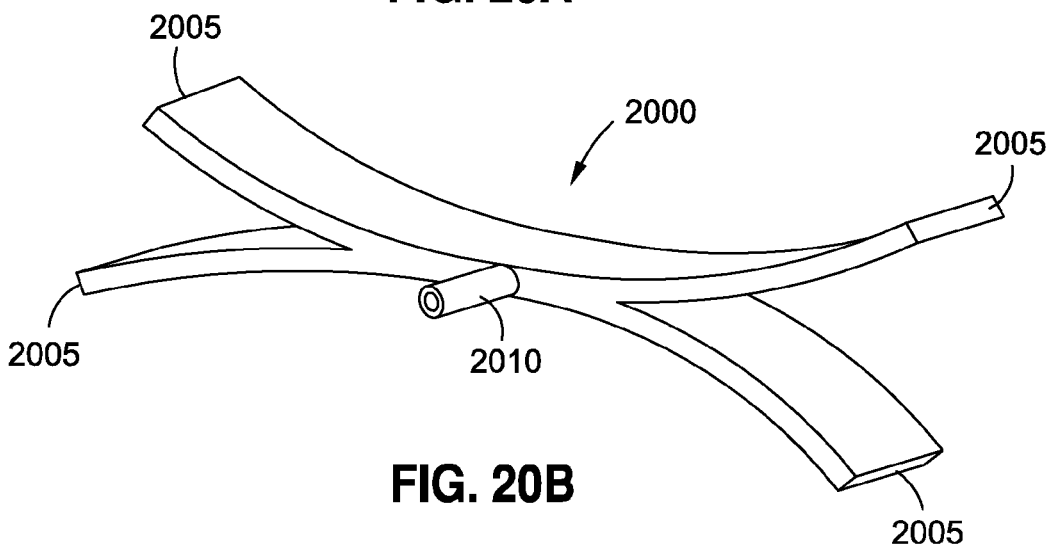
FIG. 20B

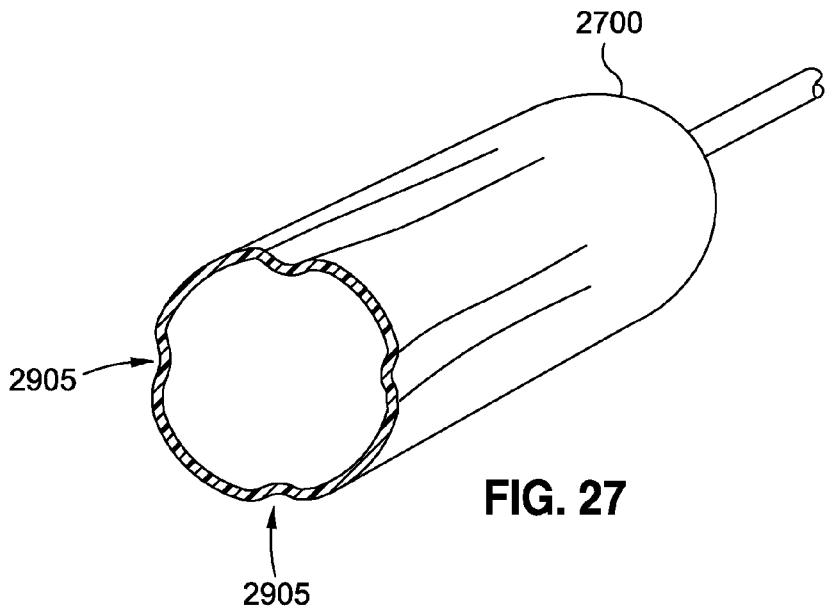
FIG. 27
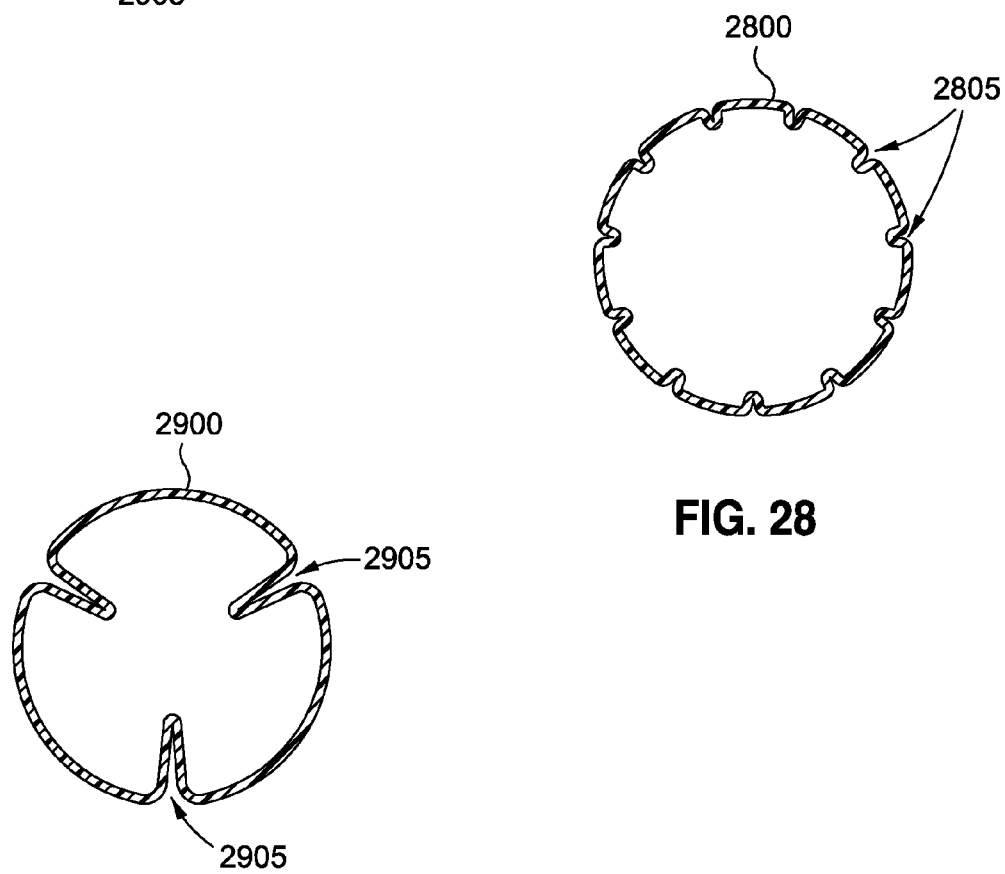
FIG. 28
FIG. 29

Dual Connected Piston

Connected Displacing Chambers

Interlaced Leafs

Single Damping Piston

SELF-ADJUSTING GASTRIC BAND

CROSS REFERENCE TO RELATED APPLICATIONS

This application is a continuation-in-part of U.S. patent application Ser. No. 13/149,585 filed on May 31, 2011, and is a continuation-in-part of U.S. patent application Ser. No. 13/049,453 filed on Mar. 16, 2011, both of which are a continuation-in-part of U.S. patent application Ser. No. 12/770,617 filed on Apr. 29, 2010, the entire disclosure of each of these applications are incorporated herein by this specific reference.

FIELD

The present invention generally relates to medical systems, devices and uses thereof for treating obesity and/or obesity-related diseases. More specifically, the present invention relates to gastric banding systems that may self-adjust to changes in a patient.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts food's passage into a lower portion of the stomach. When the stoma is of an appropriate size that is restricted by a gastric band, food held in the upper portion of the stomach may provide a feeling of satiety or fullness that discourages overeating. Unlike gastric bypass procedures, gastric band apparatus are reversible and require no permanent modification to the gastrointestinal tract. An example of a gastric banding system is disclosed in Roslin, et al., U.S. Patent Pub. No. 2006/0235448, the entire disclosure of which is incorporated herein by this specific reference.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction.

However, the level of tightness of the gastric band may effect the patient's sensations and satisfaction level. In other words, if the gastric band is underfilled, the patient may experience hunger; but if the gastric band is overfilled (and thus "too tight"), the patient may experience tightness in the chest region, suffer from a food bolus blockage, and the like.

Sometimes, adjustment of a gastric band may be desirable in between adjustments made by a physician. For example, during normal operation of the gastric band, the band applies pressure to the outer surface of the upper stomach. However, it may be difficult to achieve the most effective level of tightness, and further, physicians may tend to err on the side of underfilling the gastric band (thereby decreasing efficacy of the gastric band system) as they consider the risk of overfilling the gastric band.

Some attempts have been made to develop a gastric band that promotes an effective fill level. For example, with reference to FIGS. 1A-1B, Lau, et al., U.S. Patent Pub. No. 2010/0191271 discloses an elastic bladder that is in constant fluid communication with the expandable balloon portion of a gastric band in order to continuously adjust the gastric band. With reference to FIG. 1C, Lau, et al., U.S. Patent Pub. No. 2010/0191265 discloses an alternative elastic bladder having four wings.

With reference to FIG. 2A, Coe, et al., U.S. Patent Pub. No. 2009/0216255 discloses a flow control device A that moves fluid between a hydraulic restriction system and a fluid source B. The additional flow control device A controls a rate of fluid flow between the restriction device and the fluid source B. With reference to FIG. 2B, Coe, et al., European Patent Application No. 2 074 970 A1 discloses a separate restriction device and pressure adjustment device C. The pressure adjustment device C regulates a constant force applied by the restriction device using, for example, a bellows and a spring.

With reference to FIG. 2C, Lechner, U.S. Patent Pub. No. 2009/0054914 discloses a controllable stomach band that has a chamber for controlling restriction of the stomach band. The chamber is coupled to a separate pressure chamber D that receives fluid leaving the chamber in the stomach band. The pressure chamber D is separated from the esophageal-gastric junction of the patient's stomach.

Further, with respect to FIG. 3, Steffen, U.S. Patent Pub. No. 2009/0062826 discloses an adjustable gastric band with a "conveyance device" that is powered by a "power storage device." The power storage device operates the conveyance device to move fluid between expandable chambers to adjust the gastric band.

Accordingly, it is desirable to develop a self-adjusting gastric band that will provide the needed pressure to the stomach to create the stoma and facilitate weight control, but that will also adapt and open up to allow a large bolus to pass through. It is further desirable to create an automatically self-adjusting gastric band that does not require an electrical power source and/or external adjustments, to allow a large bolus to pass through.

Additionally, it is desirable to make the adjustments without additional, complicated fluid control mechanisms, flow rate limiting devices, and/or valves to regulate the transfer of fluid within the self-adjusting gastric band. Moreover, it is desirable to make these adjustments to the gastric band utilizing compliant components to both reduce and restore the constriction of the gastric band.

SUMMARY

This Summary is included to introduce, in an abbreviated form, various topics to be elaborated upon below in the Detailed Description.

Generally described herein are automatic, self-adjusting, gastric banding systems and improvements thereof that are capable of automatically relaxing and contracting in response to a large bolus passing through the area of a patient's stomach constricted by a gastric band. Alternatively, and/or in addition in one or more embodiments, the gastric banding systems described herein may also help prevent pouch dilatation and/or erosion. The apparatus and systems described herein may aid in facilitating obesity control and/or treating obesity-related diseases while generally being non-invasive once implanted. The automatic adjustments may also be made in response to other changes in the patient's esophageal-gastric junction, for example, in response to size, shape, and or location changes.

In one embodiment, a self-adjusting gastric band system for the treatment of obesity that adjusts to allow a bolus to pass through a constriction in a patient's stomach is disclosed. A bolus is, for example, any mass or object which may obstruct or at least partially obstruct any part of the gastrointestinal tract such as the lower esophagus, upper stomach or esophageal-gastric junction. The self-adjusting gastric band system comprises a gastric band having an inner portion, an outer portion, and an inflatable portion. The inner portion is configured to be placed around a portion of the patient's stomach to thereby create the constriction in the patient's stomach. The self-adjusting gastric band system also comprises a ring attached to the outer portion of the gastric band, the ring having a plurality of segmented portions, wherein each segmented portion includes an aperture, an access port fluidly coupled to the inflatable portion of the gastric band to fill and drain a fluid into or out of the inflatable portion, and a compliant reservoir fluidly coupled to the inflatable portion and the access port, the compliant reservoir capable of relaxing the constriction formed in the stomach by the gastric band by receiving fluid from the inflatable portion thereby allowing the bolus to pass through the relaxed constriction.

Further, the gastric band comprises a first compliant portion coupled to a part of the system. For example, the first compliant portion may be coupled to the inflatable portion, the access port, and/or the tubing. The first compliant portion automatically relaxes the constriction formed by the self-adjusting gastric band and allows the large bolus to pass through the constriction. After the bolus passes through the constriction, the gastric band automatically returns to its previous state.

In accordance with various embodiments, the first compliant portion facilitates automatically relaxing the constriction formed by the self-adjusting gastric band without causing a fluid to exit the inflatable portion of the gastric band. For example, the self-adjusting gastric band may comprise a ring coupled to the inflatable portion of the gastric band. The ring provides structure and support to the inflatable portion, and the ring facilitates disposing the inflatable portion about the esophageal-gastric junction.

The ring may be a flexible ring with a diameter that expands when a predetermined pressure is generated in the inflatable portion. For example, the predetermined pressure may be generated in response to the large bolus passing through the esophageal-gastric junction. The flexible ring expands to automatically relax the constriction formed by the self-adjusting gastric band. In various embodiments, the ring has a durometer in the range of approximately 20 to approximately 70.

According to a further embodiment, the first compliant portion receives a first amount of fluid from the inflatable portion when the large bolus causes a pressure in the first compliant portion to exceed an expansion pressure. Receiving the first amount of fluid from the inflatable portion facilitates relaxing the constriction formed by the self-adjusting gastric band and allowing the large bolus to pass through the constriction.

In an embodiment, the first compliant portion is fluidly coupled to the inflatable portion. The first compliant portion facilitates removing the first amount of fluid from the inflatable portion when the large bolus passes through the constriction.

According to another embodiment, the self-adjusting gastric band further comprises a second compliant portion fluidly coupled to the access port. The second compliant portion automatically removes a second amount of fluid from the inflatable portion via the access port to facilitate relaxing the constriction formed by the inflatable portion.

The tubing of the gastric banding system may be compliant tubing that expands in response to a pressure in the tubing exceeding a tubing expansion pressure when the large bolus passes through the constriction formed by the self-adjusting gastric band. In this regard, a third amount of fluid is removed from the inflatable portion when the compliant tubing expands. The tubing may be perforated to facilitate receiving the fluid from the inflatable portion via the tubing.

Further, another embodiment of the self-adjusting gastric band comprises a third compliant portion fluidly coupled to the tubing for automatically receiving a third amount of fluid from the inflatable portion via the tubing when the large bolus enters the esophageal-gastric junction. Receiving the third amount of fluid from the inflatable portion facilitates relaxing the constriction formed by the gastric band and allowing the large bolus to pass through the constriction.

The compliant components, according to various embodiments, comprise a kink-resisting feature. Further, the compliant components may comprise a leak-resisting feature. These components may be an elastic polymer, a balloon, a rubber container, a silicone container, a collapsible container, a bellows, and combinations thereof.

In an embodiment, a vacuum device may be used in transferring fluid from a gastric band to a reservoir to assist the patient in facilitating the passage of a large bolus through a constriction of the gastric band.

In an embodiment, a gastric banding system may include a tube with a gap or cut located within a balloon or reservoir. The gap or cut may allow for fluid transfer between fluidly-coupled components to the balloon or reservoir. In this manner, fluid may flow to the reservoir from an inflatable portion of the gastric banding system to relieve the pressure induced by the large bolus.

In an embodiment, a gastric banding system may include a tube with slits or holes located within a balloon or reservoir. The slits or holes may allow for fluid transfer between fluidly-coupled components to the balloon or reservoir. In this manner, fluid may flow to the reservoir from an inflatable portion of the gastric banding system to relieve the pressure induced by the large bolus.

In an embodiment, a gastric banding system may include a tube-like reservoir configured to inflate and deflate based on a volume level within the reservoir. The tube-like reservoir may be compliant and may have a star-shaped outer circumference in a first state and a circular, uniform outer circumference in a second state. Alternatively, or in addition, the middle portions of the tube-like reservoir may expand in diameter as more fluid is added.

In an embodiment, a gastric banding system may include a flattened reservoir having a uniform configuration, an indented configuration or a u-shaped configuration for inflating and deflating based on a volume level within the reservoir. In addition to providing a unique, expandable shape profiled over a continuous length, improved performance may be achieved through reduction of the effects of the external forces on fluid within an adjacent, non-compliant component.

In an embodiment, a gastric banding system may include a tube-on-tube reservoir having an outer non-compliant tube intended to prevent kinking, bending, or any other fluid disruption to an inner compliant tube. The inner compliant tube may be separated from the outer non-compliant tube by a gap which allows the inner compliant tube to expand (to fill the gap).

In an embodiment, a gastric banding system may include a reservoir with a winged portion, a coiled portion or an enlarged portion configured to inflate and deflate based on a volume level within the reservoir. These reservoirs may be attached or coupled to an access port of a gastric banding system.

In an embodiment, a gastric banding system may include a reservoir with internal structures such as a spring, a cage or a ring. The internal structures may act to prevent kinking, bending of the compliant portion, or otherwise prevent fluid flow interruptions within the reservoir.

In an embodiment, a gastric banding system may include a reservoir with external structures such as a skeleton or a protective layer. The external structures may act to prevent kinking, bending of the compliant portion, or otherwise prevent fluid flow interruptions within the reservoir.

In an embodiment, a gastric banding system may include a reservoir having depressions, pleatings or longitudinal structures along an outer circumferential perimeter. The depressions, pleatings or longitudinal structures may allow for easier and more predictable deflation of the reservoir, e.g., during implantation or removal procedures.

In an embodiment, a gastric banding system may have one or more reservoirs oriented radially from the gastric band.

In an embodiment, a gastric banding system may include non-saline fill substances such as a gel, a pseudoplastic material, or a Bingham plastic. The non-saline fill substances may have different properties that allow for different pressure behaviors when an external pressure is applied to the gastric banding system (e.g., when a large or small bolus is swallowed by the patient).

In an embodiment, a gastric banding system may be self-contained and may be filled with one or more of a various number of different fill substances. The self-contained gastric banding system may include a ring, one or more cushions, and one or more hinges that flex when a pressure is exerted on the cushions (e.g., when a patient swallows a large or small bolus of food).

In an embodiment, a gastric banding system may include a hybrid gas-saline component. The gas component may be a balloon or other gas filled member coated with a gas-impermeable coating and may be designed to flow between other components of the gastric banding system based on the pressure exerted, e.g., by a large bolus passing through a constriction formed by the gastric band.

In an embodiment, a gastric banding system may include an access port having a movable surface, which may move in response to a pressure change within the gastric banding system. For example, the movable surface may be a complaint portion that moves to increase the volume of the fluid portion (and therefore increases compliance) when the pressure increases within the gastric banding system (e.g., in response to a large bolus moving through a constriction of the gastric band). Once the pressure is reduced (e.g., the large bolus passing through the constriction), the movable surface may return to its original position, thereby decreasing the volume of the fluid portion of the access port. The access port may further include a septum, a fluid-permeable membrane, o-rings and a gas spring portion filled with a gas. Alternatively or in addition, the gas spring portion may be replaced with a wave spring, a cantilever spring, a constant force spring, a coil spring, a leaf spring, a Belleville spring, a hybrid polymer coil-air spring and the like.

In an embodiment, a gastric banding system may include a flow-rate control device. The flow rate control device may improve comfort of a patient when a large bolus is passing through the constriction by increasing the rate that fluid flows out of the gastric band and into the reservoir. In this manner, the pressure increase may be significantly reduced. Once the bolus passes, the reservoir-side pressure may gradually decrease as the gastric band begins to inflate again with fluid, and the gastric banding system may approach the equilibrium pressure.

In an embodiment, a gastric banding system may include a gastric band without a locking portion, and with a more inflexible ring portion. More particularly, instead of having a flexibly-stiff ring locked in place at an open end (as traditionally utilized in a standard gastric band), the gastric banding system does not include a locking portion and replaces the flexibly-stiff ring with a more inflexible ring such as a snap ring, a split ring, retaining ring and the like.

In an embodiment, a gastric banding system may include a ring and corresponding inflatable portions having a wider portion. The wider portion may operate to stimulate and restrict the patient's esophageal-gastric junction when the patient is not eating or swallowing small boluses. When the patient swallows medium-sized boluses, the wider portion may channel the medium bolus through the standard portions. And when the patient swallows large boluses, the wider portion may function to relieve the stress on the patient's tissue and assist to prevent formations of pouch dilatations.

In an embodiment, a gastric banding system may include a gastric band without a ring portion. The gastric band without a ring portion may be more flexible (e.g., by having decreased ring stiffness) than a standard gastric band, thereby resulting in a gastric banding system having muted pressure or force spikes on the tissues (e.g., in the esophageal-gastric junction) in a patient when the patient consumes a large bolus of food.

In an embodiment, a gastric banding system may include a gastric band with a modified ring portion. The modified ring portion may be more flexible (e.g., by having decreased ring stiffness) than a standard gastric band, thereby resulting in gastric banding systems having muted pressure or force spikes on the tissues (e.g., in the esophageal-gastric junction) in a patient when the patient consumes a large bolus of food.

In an embodiment, the ring and/or the belt of a standard or compliant gastric band may be modified to result in a band with increased compliance. For example, the ring and/or the belt may be modified with respect to material and/or geometry to increase compliance.

In an embodiment, a self-adjusting gastric band may comprise an inflatable portion disposable about an esophageal-gastric junction of the patient, a ring attached to the inflatable portion, the ring having a plurality of segmented portions, wherein each segmented portion includes an aperture, an access port fluidly coupled to the inflatable portion to fill and drain the inflatable portion, and a compliant reservoir fluidly coupled to the inflatable portion and the access port, the compliant reservoir for automatically relaxing the constriction formed by the self-adjusting gastric band and allowing the bolus to pass through the constriction by receiving fluid from the inflatable portion.

In an embodiment, a self-adjusting gastric band for the treatment of obesity that adjusts to allow a bolus of food to pass through a constriction in a patient's stomach formed by the self-adjusting gastric band, the self-adjusting gastric band comprising an inflatable portion disposable about an esophageal-gastric junction of the patient, a ring attached to the inflatable portion having a belt attached to a first end of the ring and a buckle attached to the second end of the ring configured to receive and secure the belt, the ring further comprising a tapered band between the belt and the buckle, an access port fluidly coupled to the inflatable portion to fill and drain the inflatable portion, and a compliant reservoir fluidly coupled to the inflatable portion and the access port, the compliant reservoir for automatically relaxing the constriction formed by the self-adjusting gastric band and allowing the bolus to pass through the constriction by receiving fluid from the inflatable portion.

In an embodiment, a self-adjusting gastric band may comprise a compliant inner tubing having a length and a diameter configured to be filled with saline, an outer shell disposed about the length of the compliant inner tubing and having a diameter greater than the diameter of the compliant inner tubing, and a compressible material completely filling a space between an outside surface of the compliant inner tubing and an inner surface of the outer shell.

In an embodiment, a self-adjusting gastric band may comprise an inflatable portion disposable about an esophageal-gastric junction of the patient, and a ring attached to the inflatable portion along an outer surface of the inflatable portion, the ring including a damping mechanism configured to resist displacement when a load greater than a predetermined threshold is applied, and to not resist displacement when a load smaller than a predetermined threshold is applied.

In an embodiment, a self-adjusting gastric band may comprise an inflatable portion disposable about an esophageal-gastric junction of the patient, a ring attached to the inflatable portion, a stretch limiter configured to limit the expansion of the inflatable portion, an access port fluidly coupled to the inflatable portion to fill and drain the inflatable portion and a compliant reservoir fluidly coupled to the inflatable portion and the access port, the compliant reservoir for automatically relaxing the constriction formed by the self-adjusting gastric band and allowing the bolus to pass through the constriction by receiving fluid from the inflatable portion.

BRIEF DESCRIPTION OF THE DRAWINGS

The features, obstacles, and advantages of the present invention will become more apparent from the detailed description set forth below when taken in conjunction with the drawings, wherein:

FIG. 19A illustrates a perspective view of a coiled reservoir in a first state according to an embodiment of the present invention.

FIG. 19B illustrates a perspective view of the coiled reservoir of FIG. 19A in a second state according to an embodiment of the present invention.

FIG. 20A illustrates a perspective view of a reservoir having winged portions in a first state according to an embodiment of the present invention.

FIG. 20B illustrates a perspective view of the reservoir having winged portions of FIG. 20A in a second state according to an embodiment of the present invention.

FIG. 27 illustrates a perspective, cross-sectional view of a reservoir having depressions according to an embodiment of the present invention.

FIG. 28 illustrates a cross-sectional view of a reservoir having depressions according to an embodiment of the present invention.

FIG. 29 illustrates a cross-sectional view of a reservoir having depressions according to an embodiment of the present invention.

DETAILED DESCRIPTION

Apparatuses, systems and/or methods that implement the embodiments of the various features of the present invention will now be described with reference to the drawings. The drawings and the associated descriptions are provided to illustrate some embodiments of the present invention and not to limit the scope of the present invention. Throughout the drawings, reference numbers are re-used to indicate correspondence between referenced elements.

The present invention generally provides self-adjusting gastric banding systems, for example, for treatment of obesity and obesity related conditions, as well as systems for allowing automatic self-adjustment of gastric bands when a patient swallows a large bolus.

Self-adjusting gastric bands are effective in helping a patient lose weight when the band is properly tightened around the patient's esophageal-gastric junction. During normal operation, the band applies pressure to the outer surface of the upper stomach. But, in some instances, the patient may swallow a bolus which is too large to pass through the constriction produced by the band—for example, when the patient swallows a large piece of steak. The result can be a painful experience which, if it persists, may require medical intervention to release the blockage.

In accordance with various embodiments of the present invention, the self-adjusting gastric band provides the needed pressure to the stomach to encourage weight loss. However, when a large bolus of food is swallowed, the self-adjusting gastric band temporarily and automatically opens up to allow the bolus through. After the bolus passes through, the mechanisms within the band return the band to its original size and shape. In an embodiment, electrical power and/or power external to the patient is not utilized to perform these adjustments. Further, in an embodiment, complicated fluid control mechanisms, flow rate limiting devices, and/or valves are not utilized to regulate the transfer of fluid within the self-adjusting gastric band.

Figure 1A:
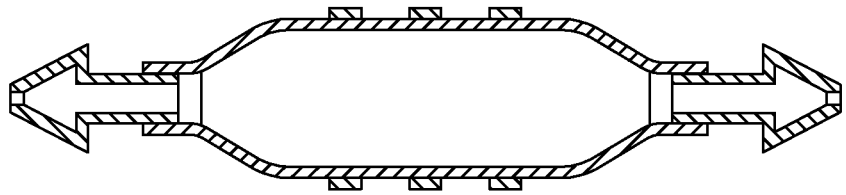
FIG. 1A illustrates a prior art system that includes a elastic bladder.
Figure 1B:
FIG. 1B illustrates a prior art system that includes an elastic bladder having a fold.
Figure 1C:
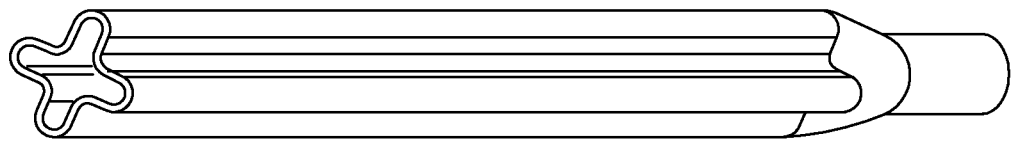
FIG. 1C illustrates a prior art system that includes an elastic bladder having four wings.
Figure 2A:
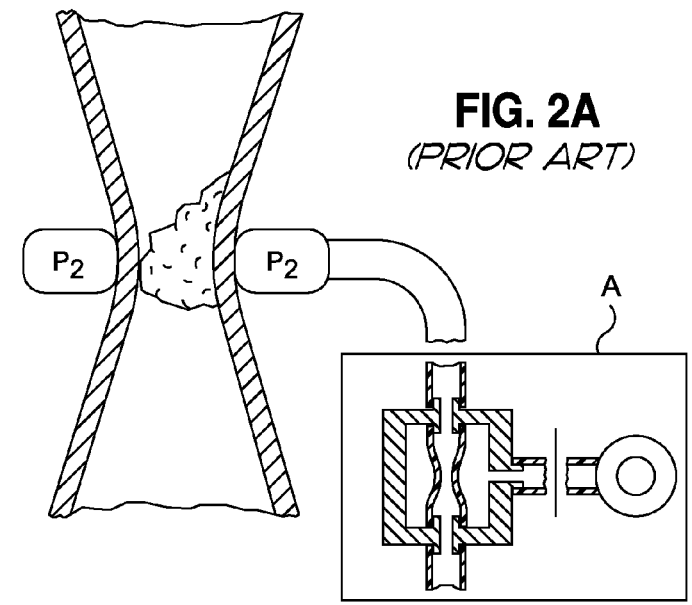
FIG. 2A illustrates a prior art system that includes a flow rate limiting device.
Figure 2B:
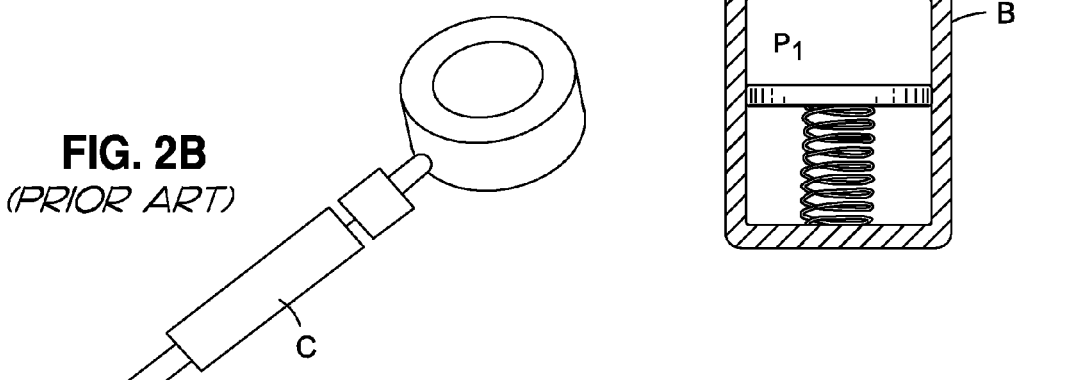
FIG. 2B illustrates a prior art system that includes a fluid control mechanism.
Figure 2C:
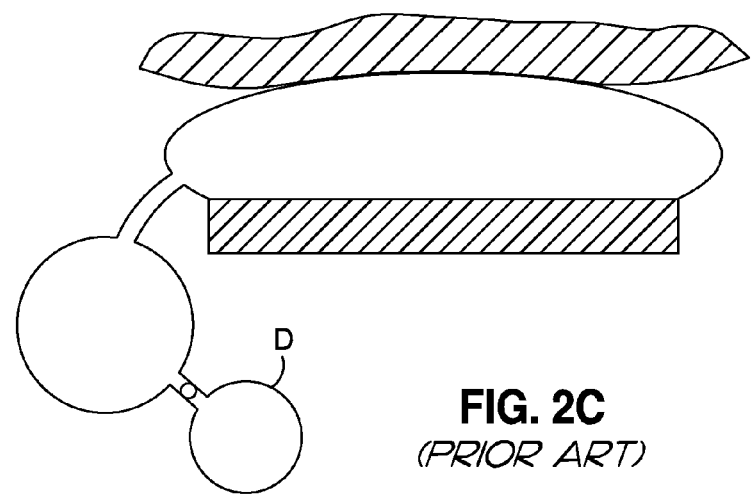
FIG. 2C illustrates a prior art system that includes a valve and a chamber separated from the esophageal-gastric junction.
Figure 3:
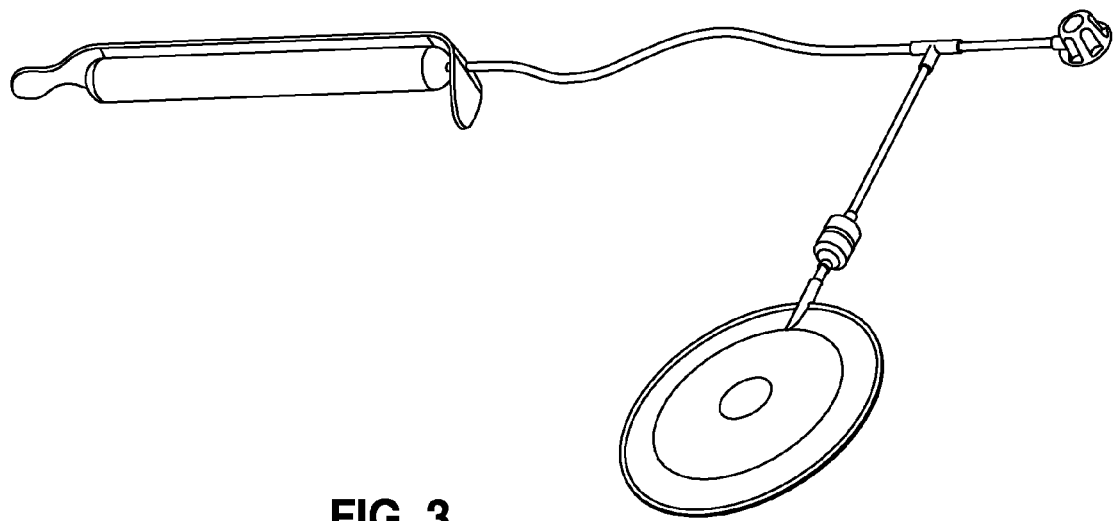
FIG. 3 illustrates a prior art system that includes a gastric band with a "conveyance device" that is powered by a "power storage device."
Figure 4:
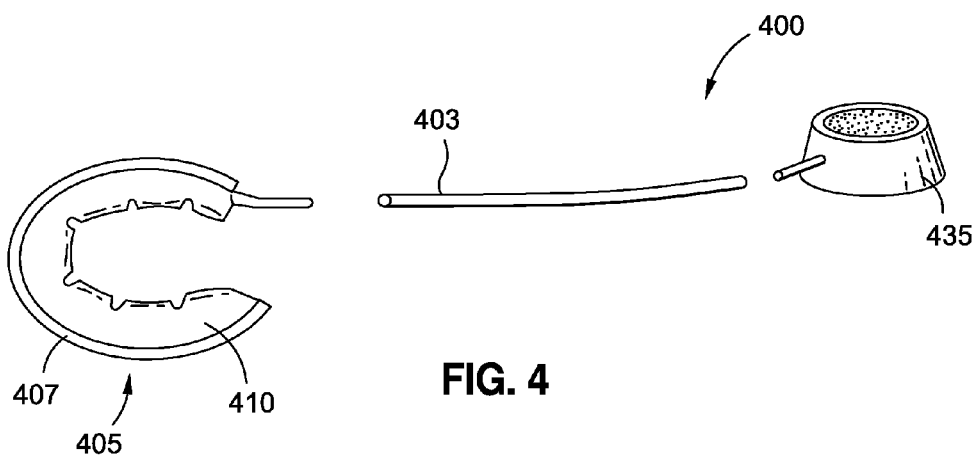
FIG. 4 illustrates an exploded, perspective view of a self-adjusting gastric banding system according to an embodiment of the present invention.

Turning now to FIG. 4, a self-adjusting gastric banding system 400 includes a gastric band 405 coupled to a subcutaneous injection port 435 via tubing 403. The gastric band 405 includes a circular ring 407 and an inflatable portion 410 disposed on the inside of the ring 407. The inflatable portion 410 separates the patient's stomach from the ring 407 when the gastric band 405 is implanted around the esophageal-gastric junction of the patient's stomach. The ring 407 provides structure and support to the inflatable portion 410, and facilitates implanting the gastric band 405 around the patient's stomach.

The access port 435 may be sutured onto the rectus muscle sheath or any other conveniently accessible muscle. The rectus muscle sheath provides a secure surface on which to attach the access port 435 under a layer of fat that separates the patient's skin from the muscle.

The inflatable portion 410 may be filled and drained with a fluid via the tubing 403. For example, the tubing 403 may be connected to the subcutaneous access port 435 for filling and draining the inflatable portion 410 via subcutaneous injections. The inflatable portion 410 may also be coupled to a reservoir to facilitate automatic adjustment of the inflatable portion 410, and the constriction it causes, when a large bolus attempts to pass through the constriction. When more fluid is introduced in the inflatable portion 410, the constriction around the stomach generally becomes tighter. Correspondingly, when less fluid is present, the constriction loosens and/or opens up.

The fluids used within the gastric band 405 may include any fluid that is biocompatible and incompressible. The fluid has no adverse effect on the patient in the unlikely event that a leak emanates from the system. The fluid can simply be water or any biocompatible polymer oil such as caster oil. In an example embodiment, the fluid is saline, a drug, and/or combinations thereof.

In an embodiment, the ring 407 is designed to be a compliant portion of the gastric band 405. For example, the ring 407 may flex and/or expand in response to a bolus of food moving through the constriction caused by the gastric band 405. The ring 407 may have flexible components and rigid components, such that the flexible components expand when a certain elevated and/or maximum pressure is reached in the inflatable portion 410. This elevated pressure may exist due to the presence of an obstruction such as a bolus near the gastric band 405. As the ring 407 expands, the diameters of the ring 407 and the inflatable portion 410 increase, and the constriction on the stomach due to the gastric band 405 is reduced to allow the bolus to pass through. When the bolus has passed, the elevated pressure no longer exists, and the gastric band 405 returns to the pre-obstruction state.

In another embodiment, the entire ring 407 may be flexible and/or expandable such that a diameter of the ring 407 increases in response to the elevated pressure in the inflatable portion 410. For example, the ring 407 may be constructed of silicone that has a durometer in the range of approximately 20 to approximately 70.

It should be understood that the flexible ring 407 and the other mechanisms disclosed herein for automatically adjusting the constriction of the gastric band 405 are only example embodiments. Any mechanism for automatically adjusting the constriction of the gastric band 405 that does not include electrical power, power external to the patient, complicated fluid control mechanisms, flow rate limiting devices, and/or valves is contemplated within the scope of the present invention. As an example, the term "automatically" refers to situations when the compliant member expands, moves, contracts or is altered without the use of an electronic device causing the change.

Figure 5:
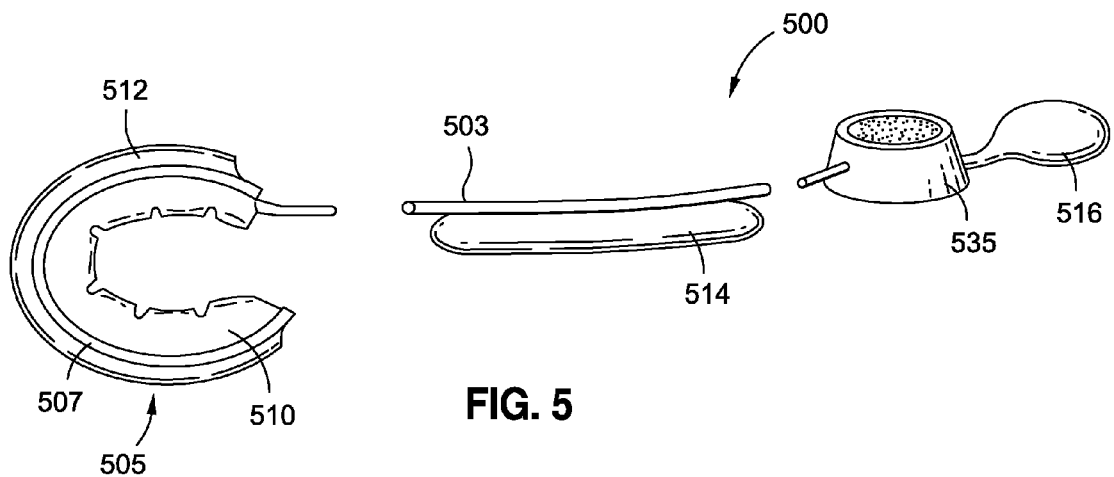
FIG. 5 illustrates an exploded, perspective view of a self-adjusting gastric banding system having various compliant components according to an embodiment of the present invention.

With reference to FIG. 5, various compliant components may be utilized to automatically adjust the constriction of the gastric band 505 about the esophageal-gastric junction of the patient's stomach. Although three compliant components are illustrated in FIG. 5, as noted above, one or more of the components may be present in various embodiments of the present invention.

For example, in an embodiment, a band compliant component 512 is fluidly coupled to the inflatable portion 510 of the gastric band 505. The compliant component 512 is located on the outside of the ring 507, opposite the inflatable portion 510, and may be coupled to the ring 507 and the inflatable portion 510. Further, in an embodiment, one or more fluid ports may extend from the inflatable portion 510 to the compliant component 512 to fluidly couple the inflatable portion 510 to the compliant component 512.

Figure 6:
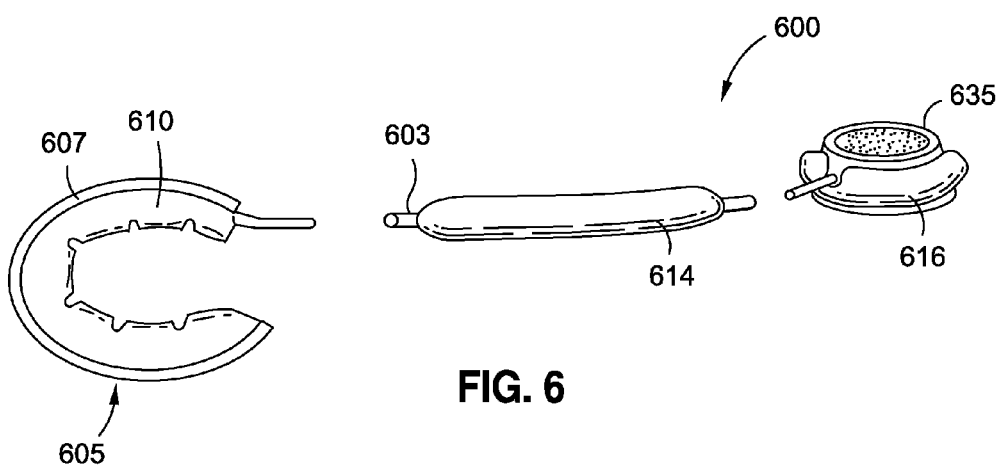
FIG. 6 illustrates an exploded, perspective view of another self-adjusting gastric banding system having various compliant components according to an embodiment of the present invention.

With reference to FIGS. 5 and 6, and in accordance with various embodiments, a tube compliant component 514, 614 may be fluidly coupled to the tubing 503, 603. As illustrated in FIG. 6, the compliant component 614 may run along substantially the entire length of the tubing 603. In another embodiment, as illustrated in FIG. 5, the compliant component 514 may be limited to a smaller section of the entire length of the tubing 503. The compliant component 514, 614 may be fluidly coupled to the tubing 503 at one or more locations. For example, with reference to FIG. 6, the compliant component 614 and the tubing 603 may be perforated to allow for efficient transfer of the fluid between the tubing 603 and the compliant component 614.

In another embodiment, the tubing 603 itself may be compliant, and the durometer, thickness, and/or diameter of the tubing 603 may be altered to achieve a desired degree of compliance. Other components of the gastric band 605 may similarly have altered properties in order to achieve a desired degree of compliance.

In an embodiment where the tube compliant component 514, 614 facilitates automated adjustment of the gastric band 505, 605, the compliant component 514, 614 may have features configured to resist kinking and/or leakage of the tubing 503, 603. For example, the compliant component 514, 614 may include rigid portions (e.g., similar to a skeleton) and flexible portions. The rigid components may give structure to the compliant component 514, 614 and/or the tubing 503, 603 to prevent kinking and/or leakage due to external forces on the compliant component 514, 614 and/or the tubing 503, 603. The flexible components may automatically expand in response to an increased pressure in the inflatable portion 510, 610 of the gastric band 505, 605.

In accordance with another embodiment, and with continued reference to FIGS. 5 and 6, the access port 535, 635 may be fluidly coupled to a port compliant component 516, 616. As illustrated in FIG. 5, the compliant component 516 may be a balloon, reservoir, or other expandable device that is adjacent to the port 535. In an embodiment as illustrated in FIG. 6, the compliant component 616 may substantially surround the access port 635. The compliant component 616 may be fluidly coupled to the access port 635 at a single location near a coupling between the tubing 603 and the access port 635. In another embodiment, the compliant component 616 may be fluidly coupled to the access port 635 at multiple locations.

As noted above, any combination of the inflatable portion compliant component 512, a compliant ring 407, the tube compliant component 514, 614, and/or the port compliant component 516, 616 may be used in accordance with various embodiments. When the pressure in the inflatable portion 510, 610 exceeds a predetermined pressure, the compliant components 407, 512, 514, 516, 614, 616, in any particular configuration or combination, expand to receive an amount of the fluid from the inflatable portion 510, 610 via the inflatable portion 510, 610, the tubing 503, 603, and/or the access port 535, 635, and/or to reduce the constriction formed by the gastric band 405, 505, 605. The predetermined pressure may be predetermined based on a pressure that would indicate an obstruction is attempting to pass through the constriction caused by the gastric band 405, 505, 605.

The compliant components 407, 512, 514, 516, 614, 616 described herein, in accordance with various embodiments, may be designed with an expansion pressure at which pressure the components 407, 512, 514, 516, 614, 616 begin to expand, to receive fluid from the inflatable portion 510, 610 of the gastric band 505, 605, and/or to reduce the constriction formed by the gastric band 405, 505, 605. The expansion pressure may be configured to correspond to a predetermined pressure in the inflatable portion 410, 510, 610 that may indicate an obstruction exists in the esophageal-gastric junction.

For example, the obstruction may result in a large spike in intra-esophageal pressure that exceeds the expansion pressure and causes the compliant components to expand and receive fluid from the inflatable portion 510, 610. The reduction in fluid in the inflatable portion 510, 610 causes the constriction around the patient's stomach to loosen, in order to relieve the spike in pressure and allow the obstruction to pass through the esophageal-gastric junction. When the obstruction passes, the increased pressure in the inflatable portion 510, 610 is reduced, and the fluid flows back into the inflatable portion 510, 610 due to the elasticity of the compliant components 512, 514, 516, 614, 616, to restore the original amount of constriction of the gastric band 505, 605. This change in constriction of the gastric band 505, 605 results or is achieved without the use of flow rate limiting devices or valves.

The various compliant components disclosed herein may have any shape or configuration that facilitates removing an amount of fluid from the inflatable portion of the gastric band in response to an increased pressure in the inflatable portion. For example, the compliant components may be selected from a group consisting of a compressible reservoir, an elastic polymer, a balloon, a rubber container, a silicone container, a collapsible container, a bellows, and combinations thereof that are configured to contain the fluid.

Figure 7A:
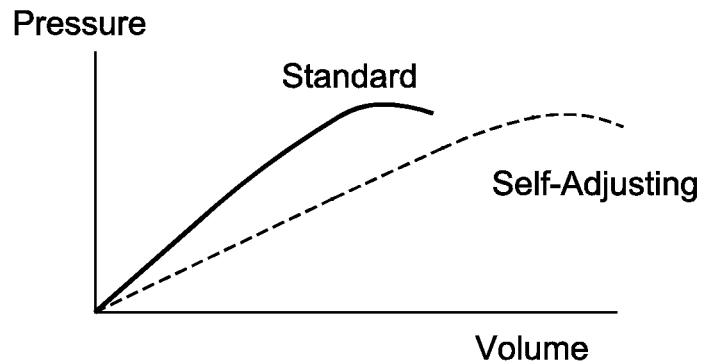
FIG. 7A illustrates a chart showing pressure-volume curves for a standard gastric band and a self-adjusting gastric band according to an embodiment of the present invention.

The graph in FIG. 7A illustrates, according to various embodiments, the effect the compliant components described herein have on the pressure in the gastric banding system. As can be seen in FIG. 7A, a standard gastric banding system without compliant components has a certain pressure-volume relationship. After the gastric banding system is flushed with saline to remove any air trapped within the system (e.g., in the gastric band, the tubing, and the port), the pressure-volume relationship generally takes the form illustrated by the "Standard" curve in FIG. 7A. The dashed "Compliant" curve illustrates an example embodiment of the pressure-volume relationship for a gastric banding system with one or more compliant components. As illustrated, the self-adjusting gastric banding system may include a greater volume of saline than a standard gastric banding system for a given level of pressure.

Figure 7B:
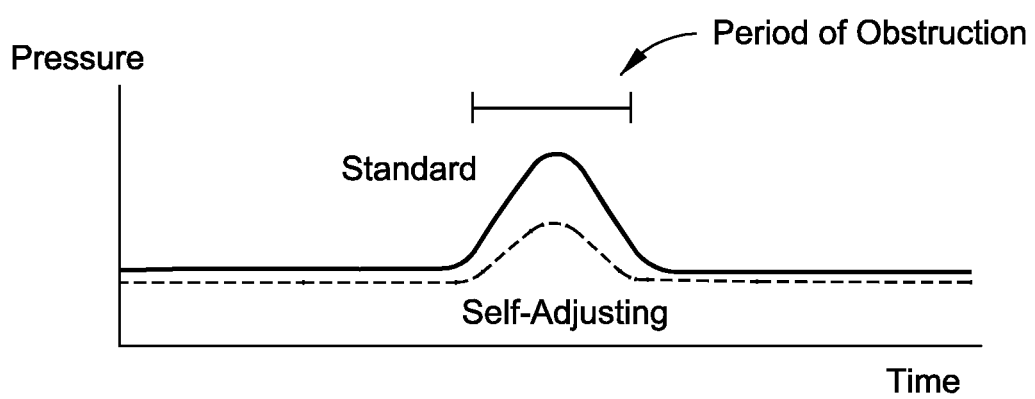
FIG. 7B illustrates a chart showing pressure-time curves for a standard gastric band and a self-adjusting gastric band subject to a period of obstruction according to an embodiment of the present invention.

The graph in FIG. 7B illustrates, according to various embodiments, pressure characteristics of a "Standard" gastric banding system and a "Self-Adjusting" gastric banding system during use of the systems in a patient. Initially, the two systems are set to the same operating pressure, for example, for a desired level of constriction of the patient's stomach. As a large bolus of food or some other obstruction encounters the gastric band, the pressure in each system increases. As illustrated, the standard system has a larger pressure increase during the period of obstruction than the self-adjusting gastric banding system experiences. This smaller increase in pressure, according to various embodiments, is due to the addition of the reservoir space in the compliant component(s). As pressure in the gastric banding system increases, fluid is transferred into the reservoir space. Once the obstruction passes, the fluid is automatically returned from the reservoir space back into the gastric band.

Figure 8A:
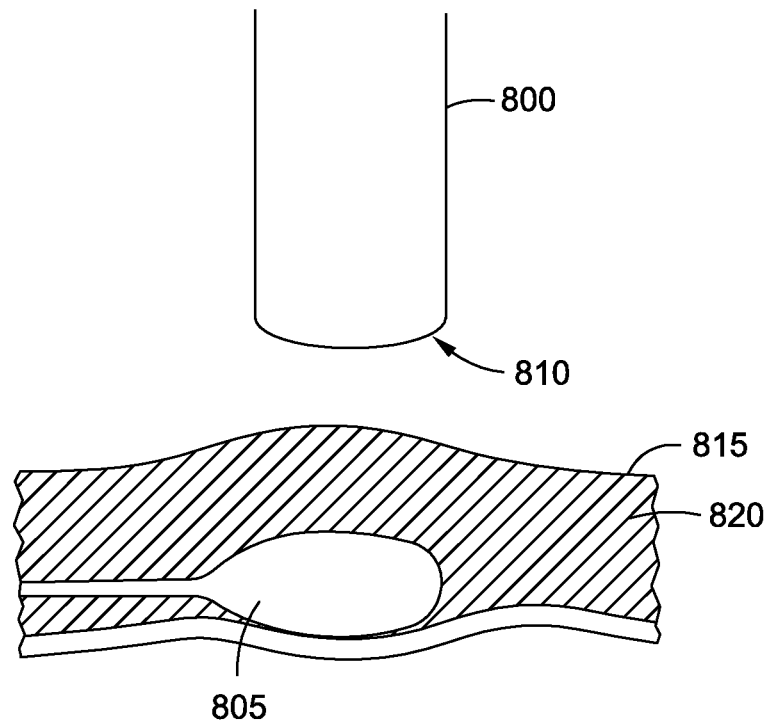
FIG. 8A illustrates a vacuum device configured to provide suction on a patient's skin proximal to the compliant reservoir according to an embodiment of the present invention.

FIG. 8A illustrates an embodiment of a vacuum device 800 which may be used to assist the patient in transferring fluid into a reservoir 805 from a gastric band (not shown) to allow a large bolus to pass through the constriction of the gastric band. The vacuum device 800 may include a tip 810, which in one embodiment, may have a diameter substantially equal to the diameter of the reservoir 805.

Figure 8B:
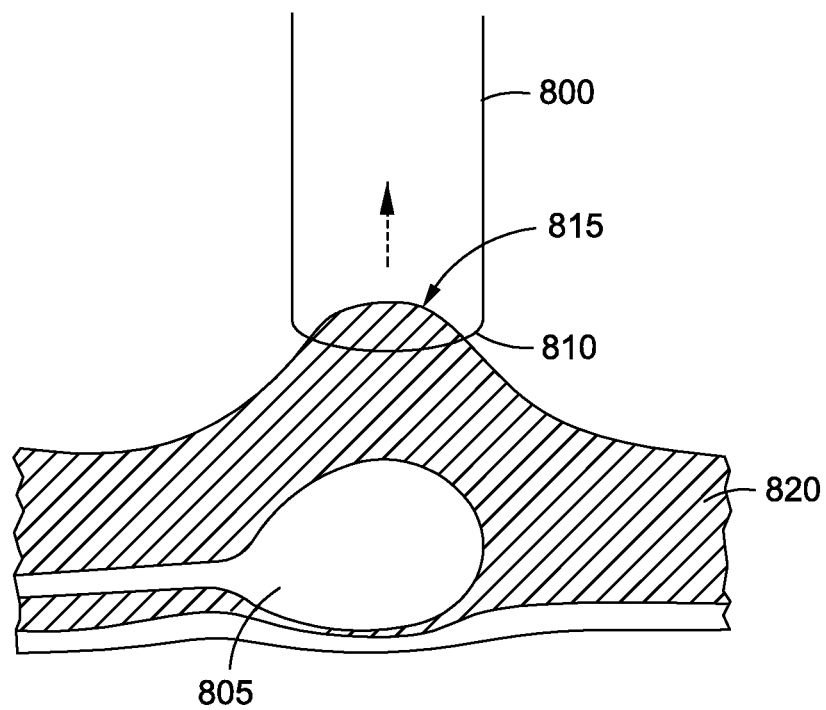
FIG. 8B illustrates the vacuum device of FIG. 8A in an operational state according to an embodiment of the present invention.

As shown in FIG. 8B, when the vacuum device 800 is activated and brought close to a patient's skin 815, the vacuum device 800, by using suction, may form a seal on a contacted area of the patient's skin 815 and slightly pull or tug on the patient's skin 815 and a subcutaneous fat layer 820 located below the skin 815. The vacuum device 800 may be configured to provide suction strength of differing magnitudes, but without harming the patient. Since there is no pathway for air or bodily fluids to collect between the subcutaneous fat layer 820 of the patient and the top surface of the reservoir 805, the top surface of the reservoir 805 may be pulled towards the vacuum device 800 along with the subcutaneous fat layer 820. As a result of the suction created, fluid may flow out of the gastric band (not shown) and into the reservoir 805 thereby relaxing a constriction caused by the gastric band and allowing a bolus of food to pass through the constriction.

Specific embodiments of a compliant self-adjusting gastric banding system having been described, attention will now be turned to additional and/or alternative improvements which may be integrated and/or implemented with any number of obesity-preventing systems, including the self-adjusting gastric banding systems described herein.

Figure 9:
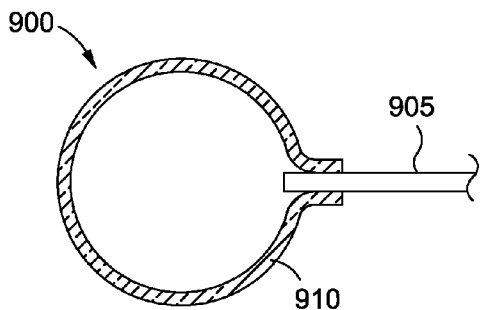
FIG. 9 illustrates a cross-sectional view of a compliant tubing-reservoir system according to an embodiment of the present invention.

Turning to FIG. 9, a close-up view of a compliant tubing-reservoir system 900 is illustrated. The compliant tubing-reservoir system 900 may include a tubing 905 which terminates at or inside a balloon or a reservoir 910. In one embodiment, the tubing (not shown in FIG. 5) may connect an injection port (e.g., injection port 535 of FIG. 5) and a reservoir (e.g., port compliant portion 516 of FIG. 5) thereby allowing a fluid path to travel through the tubing 905 to the reservoir 910. While shown here in FIG. 9 to terminate in the reservoir 910, the tubing 905 may, in one embodiment, continue and pass through. In operation, the tubing-reservoir system 900 may relieve increases in pressure, for example, generated by the passing of a large bolus swallowed by the patient. The relief may result from the transfer of fluid or other substances from an inflatable portion (not shown) through the tubing 905 and into the elastically deformable balloon or reservoir 910.

Figure 10:
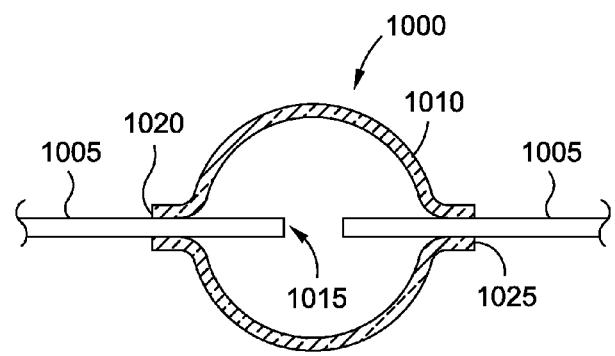
FIG. 10 illustrates a cross-sectional view of a compliant tubing-reservoir system having a gap or cut sealed within a reservoir according to an embodiment of the present invention.

FIG. 10 illustrates one embodiment of a fluid path connecting component for a pass-through tubing-reservoir system 1000 where a tubing 1005 passes through both a first opening 1020 and a second opening 1025 of a balloon or reservoir 1010. Here, the tubing 1005 may include a gap or cut 1015 inside the reservoir 1010 (which creates a fluid path between the tubing 1005 and the reservoir 1010). The gap 1015 is sealed within the reservoir 1010 such that the addition of fluid may enlarge the reservoir 1010 while the reduction of fluid may shrink or decrease the size of the reservoir 1010. In operation, the tubing-reservoir system 1000 may relieve increases in pressure, for example, generated by the passing of a large bolus swallowed by the patient. The relief may result from the transfer of fluid or other substances from an inflatable portion (not shown) through the tubing 1005 and into the elastically deformable reservoir 1010.

Figure 11:
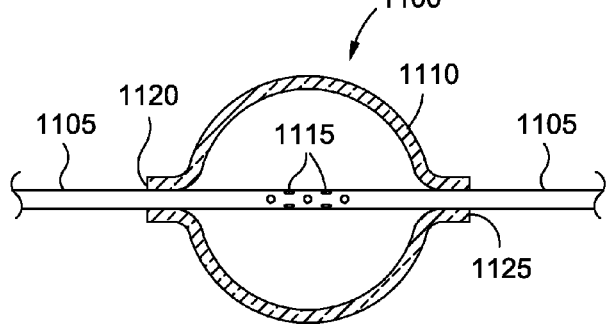
FIG. 11 illustrates a cross-sectional view of a compliant tubing-reservoir system having slits or holes sealed within a reservoir according to an embodiment of the present invention.

FIG. 11 illustrates an embodiment of a pass-through tubing-reservoir system 1100 where a tubing 1105 passes through both a first opening 1120 and a second opening 1125 of a balloon or reservoir 1110. The tubing 1105 is shown with a series of holes or slits 1115 located at a position inside the reservoir 1110 which allows fluid and/or other substances to exit the tubing 1105 and into the reservoir 1110. The same holes or slits 1115 further allow fluid and/or other substances to enter the tubing 1105 from the reservoir 1110, thereby creating the fluid path between the tubing 1105 and the reservoir 1110. In operation, the tubing-reservoir system 1100 may relieve increases in pressure, for example, generated by the passing of a large bolus swallowed by the patient. The relief may result from the transfer of fluid or other substances from an inflatable portion (not shown) through the tubing 1105 and into the elastically deformable balloon or reservoir 1110.

Figure 12:
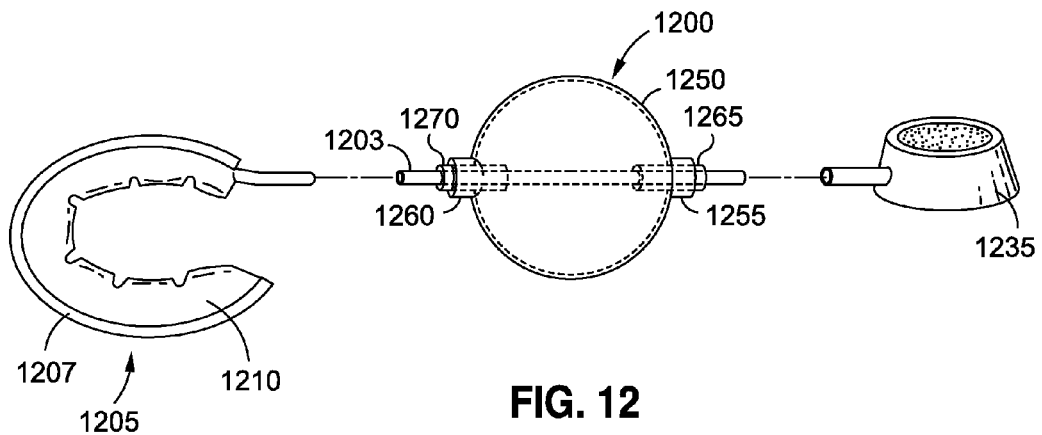
FIG. 12 illustrates an exploded, perspective view of a compliant tubing-reservoir system according to an embodiment of the present invention.

FIG. 12 illustrates an embodiment of a compliant pass-through tubing-reservoir system 1200 where a tubing 1203 passes through both a first opening 1255 and a second opening 1260 of a balloon or reservoir 1250. The system 1200 may also include a first collar 1265 and a second collar 1270 for facilitating the connection of the reservoir 1250 to the tubing 1203. The tubing 1203 may be fixed to the reservoir 1250 by the customizably-fitted first collar 1265 and the customizably-fitted second collar 1270. Here, the tubing 1203 and/or the reservoir 1250 may be compliant components creating a fluid path between a gastric band 1205 and a port 1235. In one embodiment, the gastric band 1205 and the port 1235 may be the gastric band 405 and the port 435 of FIG. 4, respectively. The gastric band 1205 may include a circular ring 1207 and an inflatable portion 1210. Similarly, the circular ring 1207 and the inflatable portion 1210 may be the circular ring 407 and the inflatable portion 410 of FIG. 4, respectively. In operation, the tubing-reservoir system 1200 may relieve increases in pressure, for example, generated by the passing of a large bolus swallowed by the patient. The relief may result from the transfer of fluid or other substances from the inflatable portion 1210 through the tubing 1203 and into the elastically deformable reservoir 1250.

In one embodiment, the balloons/reservoirs 910, 1010, 1110 and 1250 may be a spherical balloon constructed of biocompatible, elastomeric material. However, the balloon/reservoirs 910, 1010, 1110 and 1250 may be any other shape (e.g., a cylindrical balloon, etc.).

In one embodiment, each of the tubing-reservoir systems 900, 1000, 1100 and 1200 may be considered a compliant system having one or more compliant components. Moreover, the systems 900, 1000, 1100 and 1200 may be arranged with other components of a gastric banding system (e.g., gastric banding system 500 or 600) in series or in parallel with each other to optimize the overall compliance, and to add redundancy to the gastric banding system (e.g., gastric banding system 500 or 600), if desired.

Figure 13A:
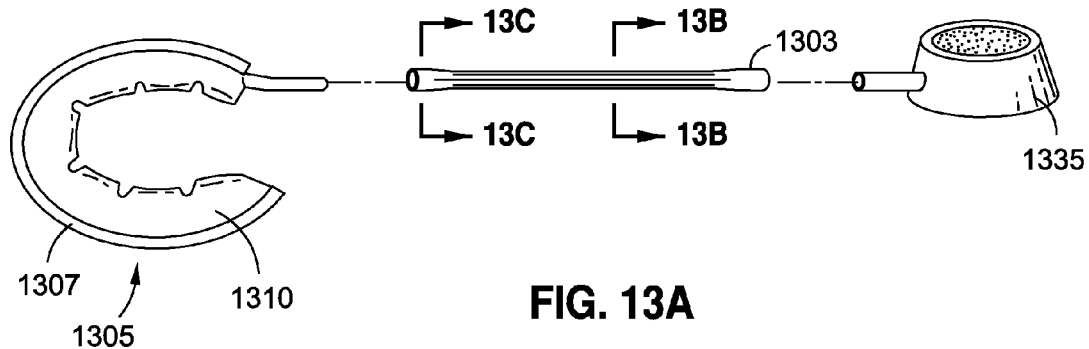
FIG. 13A illustrates an exploded, perspective view of a compliant tubing-reservoir system having a tube-shaped reservoir according to an embodiment of the present invention.
Figure 13B:
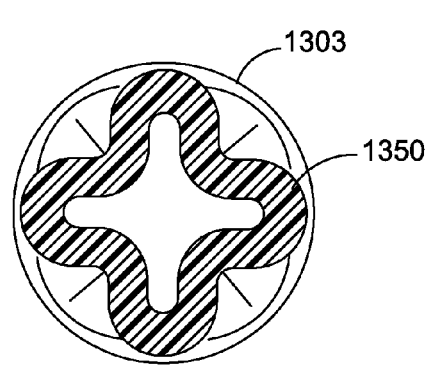
FIG. 13B illustrates a cross-sectional view of a non-extruded area of the tube-shaped reservoir of FIG. 13A according to an embodiment of the present invention.
Figure 13C:
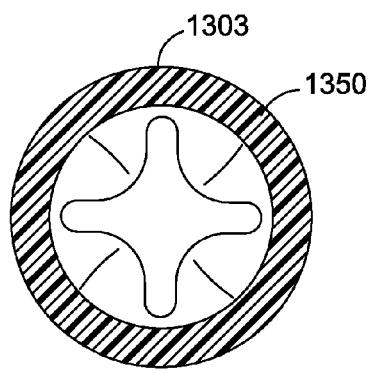
FIG. 13C illustrates a cross-sectional view of an as-extruded area of the tube-shaped reservoir of FIG. 13A according to an embodiment of the present invention.

FIGS. 13A-C illustrate one embodiment of a compliant gastric banding system 1300 having a compliant reservoir 1303. The compliant gastric banding system 1300 may further include a gastric band 1305 having a ring 1307 and an inflatable portion 1310 fluidly coupled to an access port 1335 via the reservoir 1303. As shown, the reservoir 1303 may have a tube-like appearance and may replace a balloon-type reservoir (e.g., reservoir/balloon 910, 1010, 1110, 1250) as a compliant component in any gastric banding system (e.g., gastric banding systems 900, 1000, 1100, 1200). FIG. 13A generally illustrates the reservoir 1303 in an as-extruded view. The reservoir 1303, as further shown by FIGS. 13B and 13C, may include a star-shaped structure defining an outer circumference 1350 and may be sized to expand when holding fluid that is displaced from an adjacent non-compliant fluid-carrying device (e.g., the inflatable portion 1310). In operation, the reservoir 1303 may include star-shaped folds when in a natural, deflated state as shown in FIG. 13B. However, as fluid and/or other substances begin to move into the reservoir 1303 and exert pressure on the inner walls, the star-shaped folds may deform and expand, thereby changing the appearance of the outer circumference 1350 as shown in FIG. 13C. Here, the outer circumference 1350 may appear more similar to a normal, cylindrical tube. As the fluid moves out of the reservoir 1303, the star-shaped folds may begin to re-appear and the outer circumference 1350 may revert back to its star-shaped form as shown in FIG. 13B. The reservoir 1303 may be constructed from a polymer such as silicone, in various durometers so as to expand at a controlled rate.

Figure 14A:
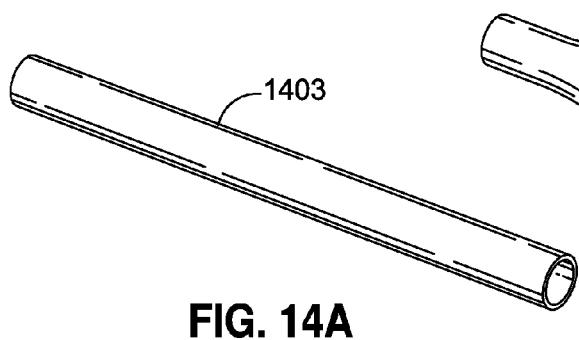
FIG. 14A illustrates a perspective view of a tube-shaped reservoir in a non-expanded state according to an embodiment of the present invention.
Figure 14B:
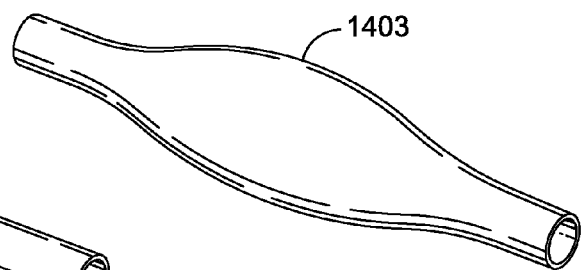
FIG. 14B illustrates a perspective view of the tube-shaped reservoir of FIG. 14A in an as-expanded state according to an embodiment of the present invention.

FIGS. 14A and 14B illustrate one embodiment of a compliant tube-like reservoir 1403 in an as-molded state (e.g., when not overly filled with a fluid) and an expanded state (e.g., when filled with a fluid above a threshold volume), respectively. The reservoir 1403 may replace a balloon-type reservoir (e.g., reservoir/balloon 910, 1010, 1110, 1250) or another tube-like reservoir (e.g., reservoir 1303) as a compliant component for any gastric banding system (e.g., gastric banding systems 900, 1000, 1100, 1200, 1300). In operation, the reservoir 1403 may appear very similar to a non-compliant, stiff tube when in a natural, as-molded state as shown in FIG. 14A. However, as fluid and/or other substances begin to move into the reservoir 1403 and exert pressure on the inner walls, the elastic wall of the reservoir 1403 may begin to deform and expand, thereby appearing more similar to the expanded state as shown in FIG. 14B. As the fluid moves out of the reservoir 1403, the elastic walls may begin to regain its original, as-molded appearance. Similar to the reservoir 1303 of FIGS. 13A-C, the reservoir 1403 may be constructed from a polymer such as silicone, in various durometers so as to expand at a controlled rate. In one embodiment, the reservoir 1403 may have a uniform diameter of between about 1 and 100 millimeters in a natural, as-molded state and may inflate to a diameter of about 10 to 1000 millimeters in an expanded state (as measured at the location of the greatest diameter).

Figure 15:
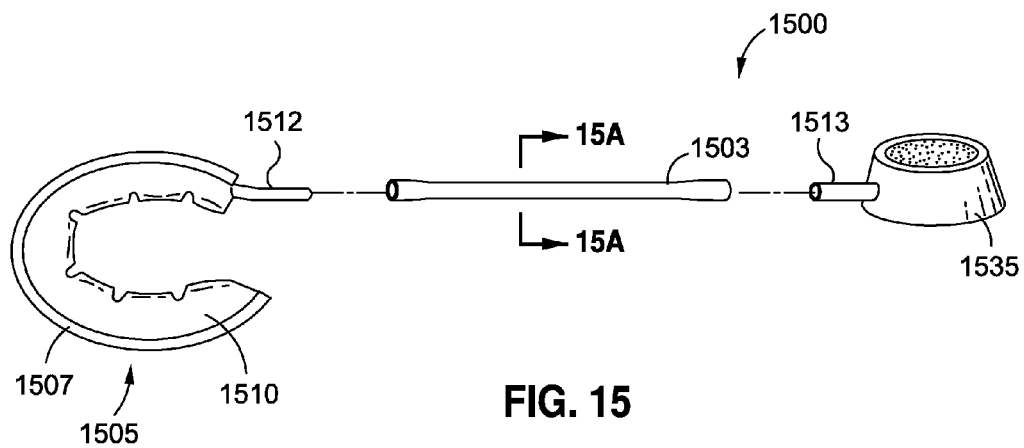
FIG. 15 illustrates an exploded, perspective view of a compliant tubing-reservoir system having a tube-shaped reservoir according to an embodiment of the present invention.

FIG. 15 illustrates one embodiment of a compliant gastric banding system 1500 having a compliant reservoir 1503. The compliant gastric banding system 1500 may further include a gastric band 1505 having a ring 1507 and an inflatable portion 1510 fluidly coupled to an access port 1535 via the reservoir 1503. As shown, the reservoir 1503 may have a flattened tube-like appearance and may replace a balloon-type reservoir (e.g., reservoir/balloon 910, 1010, 1110, 1250) as a compliant component in any gastric banding system (e.g., gastric banding systems 900, 1000, 1100, 1200). As shown, the reservoir 1503 may appear to have a flattened, tubular structure and may be sized to expand and hold fluid displaced from an adjacent non-compliant reservoir (e.g., inflatable portion 1510). The reservoir 1503 may be a fluid conduit for fluid transfer between the gastric band 1505 and the access port 1535. In one embodiment, the reservoir 1503 may be designed to be the compliant component and may function to allow for expansion so that unwanted fluid may move from a coupled stiffer tube (e.g., tube 1512 or 1513), thus reducing the amount of fluid in the stiffer tube (e.g., the tube 1512 or 1513), for a short period of time, when pressure is applied to the fluid within the stiffer tube (e.g., the tube 1512 or 1513).

Figure 15A:
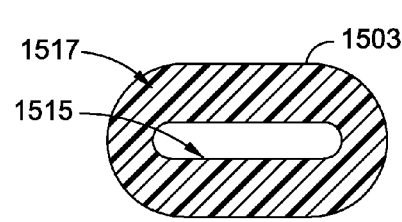
FIG. 15A illustrates a cross-sectional view of the tube-shaped reservoir of FIG. 15 according to an embodiment of the present invention.

FIG. 15A is a cross-sectional view of the reservoir 1503 of FIG. 15 and illustrates that a cross-sectional area 1515 within the reservoir 1503 where the fluid flows is continuous and smaller than a cross-sectional area 1517 of the reservoir 1503 itself. In addition to providing a unique, expandable shape profiled over a continuous length, improved performance may be achieved through reduction of the effects of the external forces on fluid within an adjacent, non-compliant component.

Figure 16:
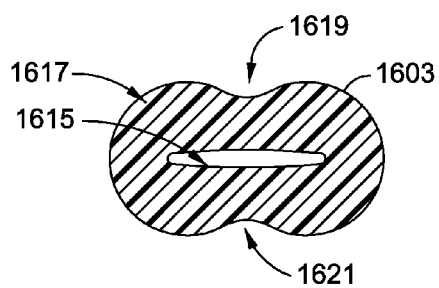
FIG. 16 illustrates a cross-sectional view of another tube-shaped reservoir according to an embodiment of the present invention.

In one embodiment, the reservoir 1503 of FIG. 15 may be replaced by a reservoir 1603 of FIG. 16. A cross-section of the tube 1603 is illustrated in FIG. 16. As shown, a cross-sectional area 1615 within the reservoir 1603 where the fluid flows is continuous and smaller than a cross-sectional area 1617 of the tube reservoir itself. In addition to providing a unique, expandable shape profiled over a continuous length, improved performance may be achieved through reduction of the effects of the external forces on fluid within an adjacent, non-compliant component. As compared to the reservoir 1503 of FIG. 15, the tube 1603 may, in one embodiment, have a smaller cross-sectional area 1617 where fluid may flow such that, an increase in fluid may cause indented portions 1619 and 1621 to expand.

Figure 17A:
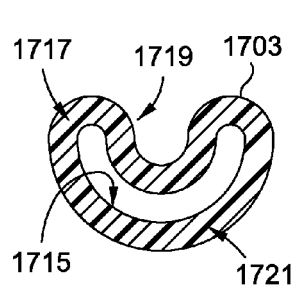
FIG. 17A illustrates a cross-sectional view of a tube-shaped reservoir in a first state according to an embodiment of the present invention.
Figure 17B:
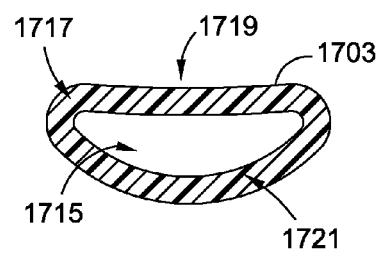
FIG. 17B illustrates a cross-sectional view of the tube-shaped reservoir of FIG. 17A in a second state according to an embodiment of the present invention.
Figure 17C:
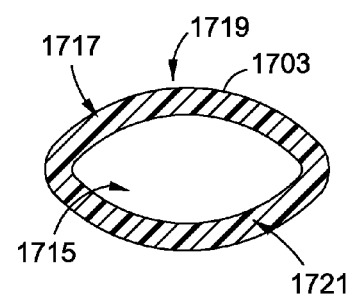
FIG. 17C illustrates a cross-sectional view of the tube-shaped reservoir of FIG. 17A in a third state according to an embodiment of the present invention.

In one embodiment, the reservoir 1503 of FIG. 15 may be replaced with a reservoir 1703 of FIG. 17A. A cross-section of the reservoir 1703 is illustrated in FIG. 17A. As shown, a cross-sectional area 1715 within the reservoir 1703 where the fluid flows is continuous and smaller than a cross-sectional area 1717 of the reservoir 1703 itself. In addition to providing a unique, expandable shape profiled over a continuous length, improved performance may be achieved through reduction of the effects of the external forces on fluid within an adjacent, non-compliant component. As compared to the reservoir 1503 of FIG. 15, the reservoir 1703 may, in one embodiment, include a U-shaped tubular structure sized to expand such that a top portion 1719 may be configured to expand from a U-shaped curve to a flatter curve (as shown in FIG. 17B) when more fluid is added to the reservoir 1703. When even more fluid is added to the reservoir 1703 (e.g., beyond a certain volume threshold), the flatter curve may protrude outward (as shown in FIG. 17C). In one embodiment, as the top portion 1719 changes from the U-shaped curve to the flatter curve to the protruded curve as fluid is added, the bottom portion 1721 may expand longitudinally (e.g., straighten out) as shown in FIGS. 17B and 17C.

The reservoirs 1503, 1603 and 1703 may each be constructed out of a polymer such as silicon, in various durometers. By controlling the durometer of the constructed material, the expansion rates as fluid is added to the reservoirs 1503, 1603 and 1703 may be controlled.

Figure 18A:
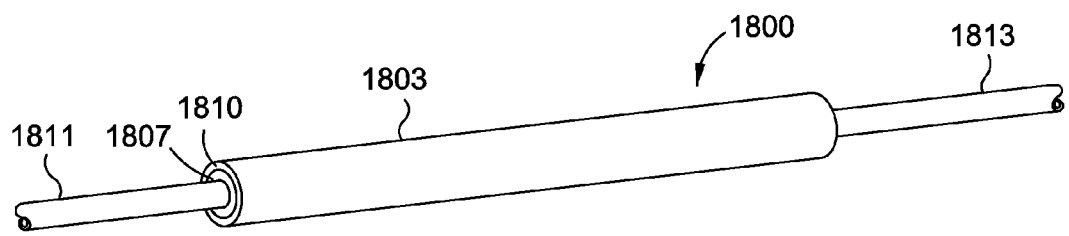
FIG. 18A illustrates a close-up view of a compliant tube-on-tube reservoir system according to an embodiment of the present invention.
Figure 18B:
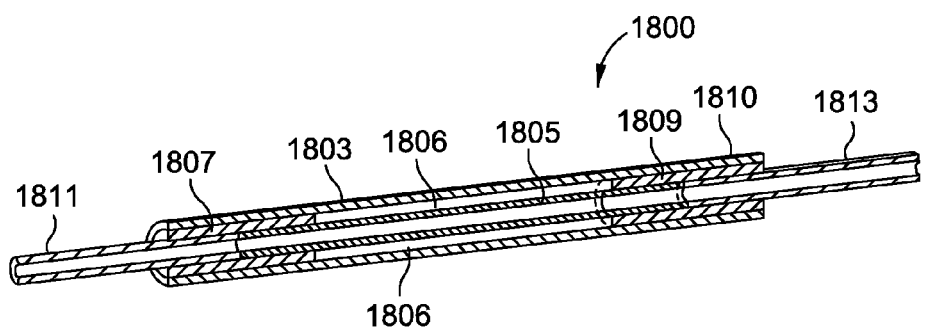
FIG. 18B illustrates a cross-sectional view of the compliant tube-on-tube reservoir system of FIG. 18A according to an embodiment of the present invention.

FIG. 18A illustrates an embodiment of a compliant tube-on-tube reservoir system 1800. The reservoir system 1800 may replace a balloon-type reservoir (e.g., reservoir/balloon 910, 1010, 1110, 1250) or another tube-like reservoir (e.g., reservoir 1303) as a compliant component for any gastric banding system (e.g., gastric banding systems 900, 1000, 1100, 1200, 1300). In one embodiment, the compliant tube-on-tube reservoir system 1800 may include a tube 1803 having an outer tube 1810 and joining portions (first joining portion 1807 shown here) configured to couple the tube 1803 (including an inner compliant tube 1805, shown in FIG. 18B) with non-compliant tube portions 1811 and 1813. FIG. 18B illustrates a cross sectional view of the system 1800, including the internal structure not shown in FIG. 18A. The inner compliant tube 1805 may enlarge when fluid is introduced into the cavity of the inner compliant tube 1805. The inner compliant tube 1805 may include a diameter substantially equivalent to the diameters of the non-compliant tube portions 1811 and 1813. The inner compliant tube 1805 may be coupled to the non-compliant tube portions 1811 and 1813 by the first joining portion 1807 and a second joining portion 1809. As shown, the joining portions 1807 and 1809 may be configured to have an inner circumference sized to fit both the inner compliant tube 1805 and the non-compliant tube portions 1811 and 1813. In one embodiment, the joining portions 1807 and 1809 do not contact one another, but instead form a gap 1806 between them. The gap 1806 may further be defined by the outer surface of the inner compliant tube 1805 and the inner surface of the outer tube 1810. The gap 1806 may serve as a sealed space for expansion of the inner compliant tube 1805 and to provide a buffer when the outer tube 1810 is compressed. The outer tube 1810 may, in one embodiment, be rigid, and may be further sized to fit the joining portions 1807 and 1809 within its internal cavity. Generally, as a patient's body presses on the non-compliant tube portions 1811 and 1813, and/or on the outer tube 1810, kinks, bending, or compression which disrupts fluid flow may be prevented.

Figure 18C:
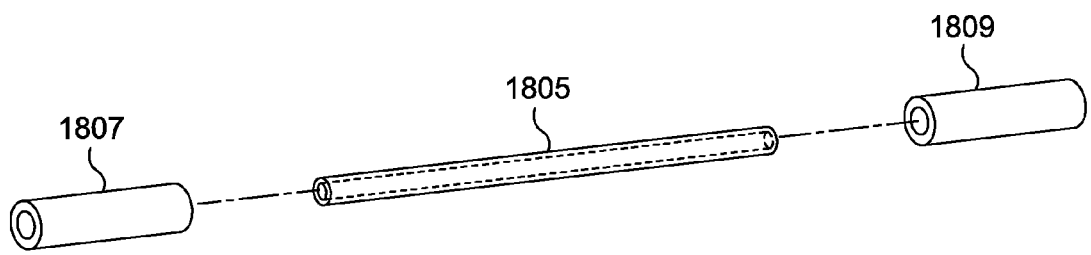
FIG. 18C illustrates a partial, exploded view of the compliant tube-on-tube reservoir system of FIG. 18A according to an embodiment of the present invention.
Figure 18D:
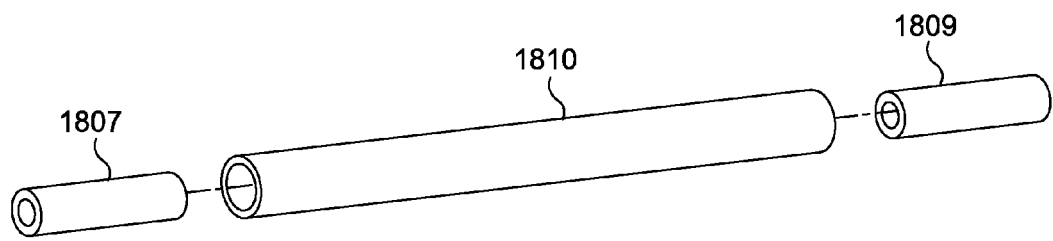
FIG. 18D illustrates a partial, exploded view of the compliant tube-on-tube reservoir system of FIG. 18A according to an embodiment of the present invention.
Figure 18E:
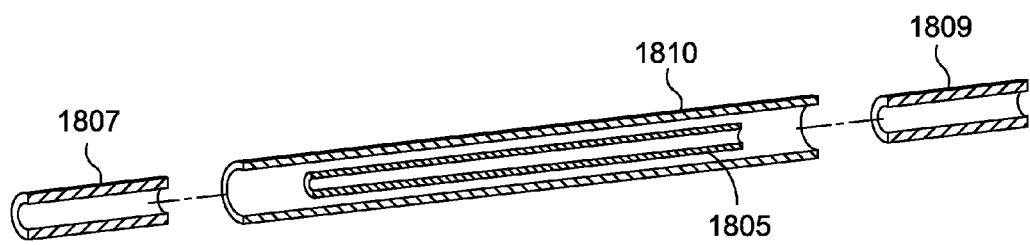
FIG. 18E illustrates a cross-sectional view of the compliant tube-on-tube reservoir system of FIG. 18D according to an embodiment of the present invention.
Figure 18F:
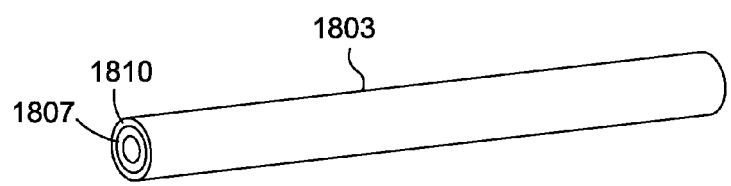
FIG. 18F illustrates a perspective view of a portion of the compliant tube-on-tube reservoir system of FIG. 18A according to an embodiment of the present invention.
Figure 18G:
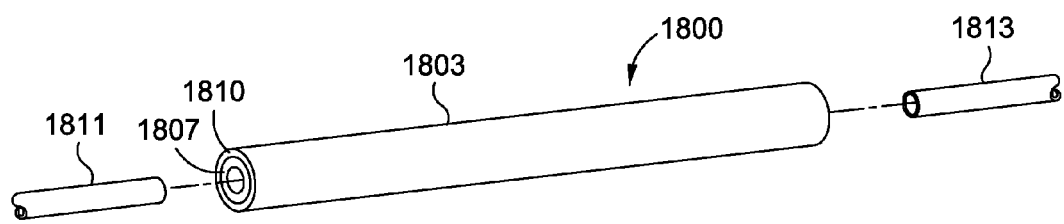
FIG. 18G illustrates a partial, exploded view of the compliant tube-on-tube reservoir system of FIG. 18A according to an embodiment of the present invention.

FIGS. 18C-18G illustrate a method of constructing the system 1800 of FIGS. 18A and 18B. As shown in FIG. 18C, the inner compliant tube 1805 may be inserted into the first joining portion 1807 and the second joining portion 1809. In one embodiment, an adhesive may be used to attach the surfaces. However, other attachment methods may be practiced without the use of any adhesive (e.g., where the inner compliant tube 1805 is sized to fit tightly into the cavity of the joining portions 1807 and 1809). FIG. 18D illustrates the outer tube 1810 overlaying the joining portions 1807 and 1809. FIG. 18E illustrates a deconstructed view of the placement of the inner compliant tube 1805 with respect to the outer tube 1810. FIG. 18F illustrates the compliant tube 1803 as fully constructed. FIG. 18G illustrates the insertion of the two non-compliant tube portions 1811 and 1813 into the compliant tube 1803 to complete the tube-on-tube reservoir system 1800.

As discussed above with respect to FIGS. 5 and 6, port compliant components 516 and 616 may be used in accordance with various embodiments, such that when the pressure in the inflatable portion 510, 610 exceeds a predetermined pressure, the port compliant component 516 and 616 may expand to receive an amount of fluid from the inflatable portion 510, 610, the tubing 503, 603, and/or the access port 535, 635, and/or to reduce the constriction formed by the gastric band 505, 605. FIGS. 19A-19B, 20A-20B and 21A-21C illustrate additional compliant reservoir systems 1900, 2000 and 2100, respectively, that may be implemented as port compliant components 516 and 616.

The compliant reservoir systems 1900, 2000 and 2100 may be constructed such that a portion of their compliance comes from a conformational change or a shape-change in the systems 1900, 2000 and 2100. For example, as the pressure inside the reservoir systems 1900, 2000 and 2100 increases, one or more portions may move to a different location or change to a different state. More particularly, the systems 1900, 2000 and 2100 take on a different shape in a pressurized state.

With respect to FIG. 19A, the compliant reservoir system 1900 may be "coiled" in a precurved shape as shown in an unpressurized state. As the pressure increases inside the system 1900 (e.g., as fluid flows into the system 1900 through a distal end 1910), a proximal end 1905 of the coiled, precurved shape may begin to "uncoil" and straighten out as the system 1900 expands from a flat tube to a more rounded tube, as shown in FIG. 19B. As the pressure is removed, the system 1900 may reform and revert into the coil-like shape due to stresses in the material.

FIG. 20A illustrates a compliant reservoir system 2000 having a distal end 2010 and "coiled wings" 2005. As shown, system 2000 may have four "coiled wings" but any number of "coiled wings" may be implemented. The "coiled wings" in FIG. 20A are shown in an unpressurized state. As the pressure increases inside the system 2000 (e.g., as fluid flows into the system 2000 through a distal end 2010), each of the "coiled wings" 2005 may begin to uncoil and straighten out as the system 2000 expands when fluid is increasingly added causing the pressure. FIG. 20B illustrates the system 2000 in a pressurized state. Here, the "coiled wings" are straightened out and no longer in the coiled position. As pressure is removed, the system 2000 may reform and revert into the coil-like shape due to stresses in the material.

Figure 21A:
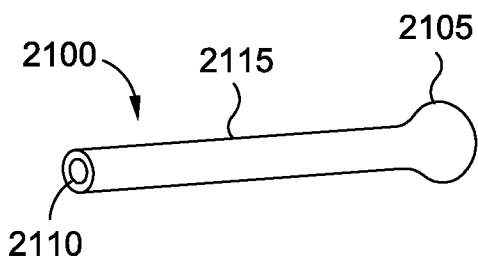
FIG. 21A illustrates a perspective view of a tube-shaped reservoir having a closed end in a first state according to an embodiment of the present invention.
Figure 21B:
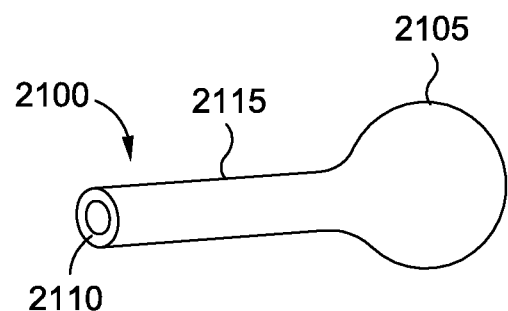
FIG. 21B illustrates a perspective view of the tube-shaped reservoir having a closed end of FIG. 21A in a second state according to an embodiment of the present invention.
Figure 21C:
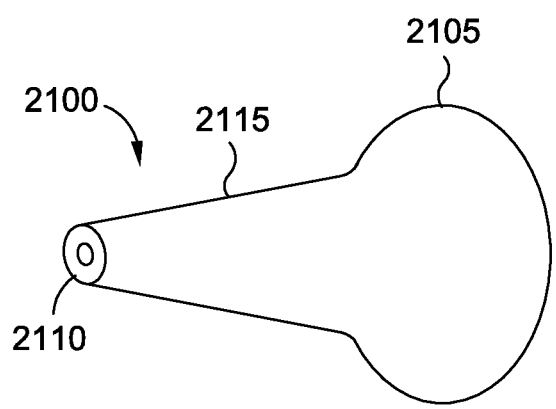
FIG. 21C illustrates a perspective view of a tube-shaped reservoir having a closed end of FIG. 21A in a third state according to an embodiment of the present invention.

FIG. 21A illustrates a compliant reservoir system 2100 having a distal opening 2110, a body portion 2115 and a bulged proximal end 2105. As the pressure increases inside the system 2100 (e.g., as fluid flows into the system 2100 through the distal end 2110), the bulged proximal end 2105 may enlarge. FIG. 21B illustrates the system 2100 in a pressurized state with an enlarged bulged proximal end 2105 storing the fluid. Here, as the fluid collects in the bulged proximal end 2105, the bulged proximal end 2105 may further increase in size. In one embodiment, the body portion 2115 may remain substantially the same size or increase slightly in response to the introduction of fluid. FIG. 21C illustrates the system 2100 when a large amount of fluid is introduced into the system 2100, thereby causing the preferential inflation of the bulged proximal end 2105. However, as shown in FIG. 21C, other portions of the system 2100 may also incrementally increase in size such as the body portion 2115. As pressure is removed, the system 2100 may revert to the shape of FIG. 21A due to stresses in the material.

In addition to, or as an alternative to reservoirs with different shapes and structures (e.g., compliant reservoir system 1900, 2000 and 2100), embodiments of compliant reservoirs may include internal structures such as springs, cages and/or rings.

Figure 22:
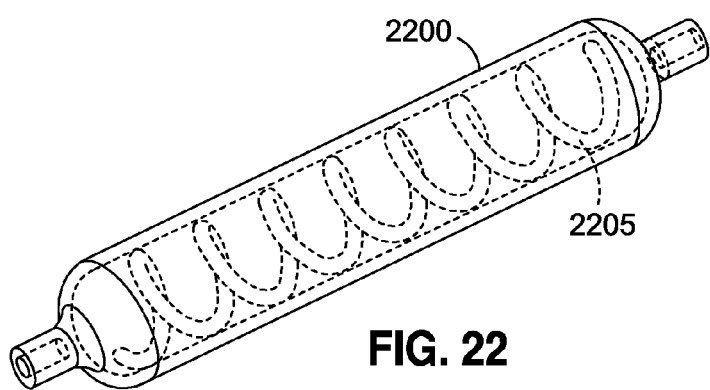
FIG. 22 illustrates a perspective view of a reservoir having an internal spring according to an embodiment of the present invention.

FIG. 22 illustrates an embodiment of a compliant reservoir 2200 which may be integrated into the tubing (e.g., tubing 403 or 503), added as an additional compliant component and/or attached to the access port (e.g., compliant component 516). As shown in FIG. 22, the compliant reservoir 2200 may include a spring 2205 which provides a skeletal structure. As the patient's body presses on the compliant reservoir 2200, the spring 2205 prevents the compliant reservoir 2200 from being kinked, bent or compressed in a way that disrupts flow of fluid or causes unwanted fluid to move into the inflatable portions (e.g., inflatable portions 510 and 610). In one embodiment, the spring 2205 may provide the compliant reservoir 2200 properties including high radial stiffness and low axial stiffness. The radial stiffness allows the compliant reservoir 2200 to support weight applied externally while the low axial stiffness provides for volumetric expansion of the compliant reservoir 2200 internally. In addition, the spring 2205 may provide internal support to resist loading from body tissues without an increase in pressure inside the compliant reservoir 2200. In one embodiment, the spring 2205 and the compliant reservoir 2200 may be configured to increase pressure relative to the volume displaced.

Figure 23:
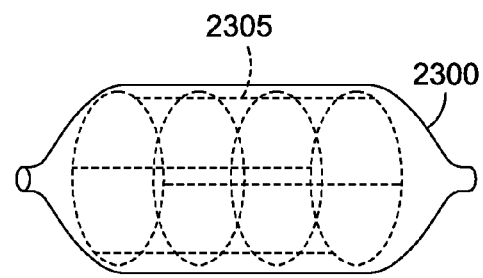
FIG. 23 illustrates a perspective view of a reservoir having an internal cage according to an embodiment of the present invention.

FIG. 23 illustrates one embodiment of a compliant reservoir 2300 having an internal structure in the form of a cage 2305. The compliant reservoir 2300 may be integrated into a tubing (e.g., tubing 403 or 503), added as an additional compliant component and/or attached to the access port (e.g., compliant component 516). As shown in FIG. 23, the compliant reservoir 2300 may include the internal cage 2305, which provides the compliant reservoir with a skeletal structure. As the patient's body presses on the compliant reservoir 2300, the rings and bars of the cage 2305 may prevent the compliant reservoir 2300 from being kinked, bent or compressed in a way that disrupts the flow of fluid or causes unwanted fluid to move into the inflatable portions (e.g., inflatable portions 510 and 610). In one embodiment, the cage 2305 may provide the compliant reservoir 2300 high radial stiffness and low axial stiffness. The radial stiffness may allow the compliant reservoir 2300 to support weight applied externally while the low axial stiffness provides for volumetric expansion of the compliant reservoir 2300 internally. In addition, the cage 2305 may provide internal support to resist loading from body tissues without an increase in pressure inside the compliant reservoir 2300. In one embodiment, the cage 2305 and the compliant reservoir 2300 may be configured to increase pressure relative to the volume displaced.

Figure 24:
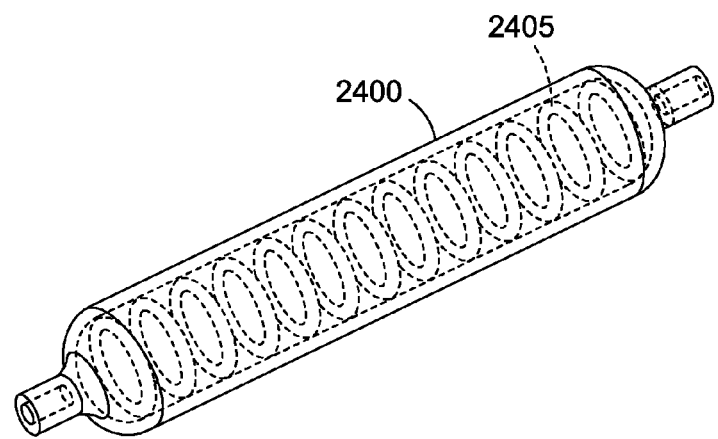
FIG. 24 illustrates a perspective view of a reservoir having internal rings according to an embodiment of the present invention.

FIG. 24 illustrates one embodiment of a compliant reservoir 2400 having an internal structure in the form of parallel rings 2405. The compliant reservoir 2400 may be integrated into a tubing (e.g., tubing 403 or 503), added as an additional compliant component and/or attached to the access port (e.g., compliant component 516). As shown in FIG. 24, the compliant reservoir 2400 may include the parallel rings 2405, which provides the compliant reservoir 2400 with a skeletal structure. In one example, the parallel rings 2405 may be joined together. As the patient's body presses on the compliant reservoir 2400, the rings 2405 may prevent the compliant reservoir 2400 from being kinked, bent or compressed in a way that disrupts flow of fluid or causes unwanted fluid to move into the inflatable portions (e.g., inflatable portions 510 and 610). In one embodiment, the rings 2405 may provide the compliant reservoir 2400 high radial stiffness and low axial stiffness. The radial stiffness may allow the compliant reservoir 2400 to support weight applied externally while the low axial stiffness provides for volumetric expansion of the compliant reservoir 2400 internally. In addition, the rings 2405 may provide internal support to resist loading from body tissues without an increase in pressure inside the compliant reservoir 2400. In one embodiment, the rings 2405 and the compliant reservoir 2400 may be configured to increase pressure relative to the volume displaced.

While the internal structures (e.g., the spring 2205, the cage 2305 and the parallel rings 2405) of FIGS. 22, 23 and may have different configurations, they may provide for different or same pressures. In one embodiment, the spring 2205, the cage 2305 and the parallel rings 2405 may be made of metals or polymers such as stainless steel, titanium, nitinol, PEEK, ultem, delrin, polycarbonate, polysulfone, among other materials. Materials used may further be combined to provide the desired properties. With respect to construction, the spring 2205, the cage 2305 and the parallel rings 2405 may be over-molded and/or contiguous with the compliant reservoir (e.g., compliant reservoirs 2200, 2300 and 2400).

In addition, or as an alternative to the internal structures of FIGS. 22-24, external structures may be utilized to protect a compliant reservoir from being kinked, bent or compressed in a way that disrupts flow of fluid or causes unwanted fluid to move into the inflatable portions (e.g., inflatable portions 510 and 610).

Figure 25:
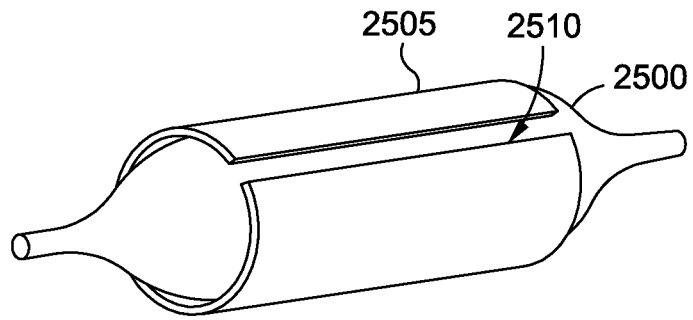
FIG. 25 illustrates a perspective view of a reservoir having an external shell according to an embodiment of the present invention.
Figure 25A:
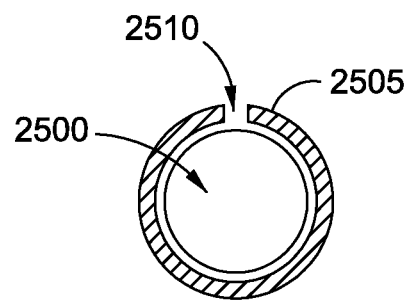
FIG. 25A illustrates a cross-sectional view of the reservoir having the external shell of FIG. 25 according to an embodiment of the present invention.
Figure 26:
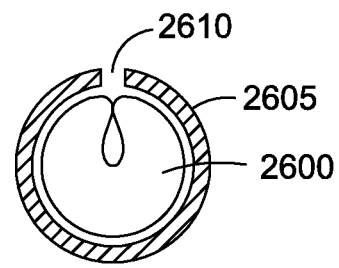
FIG. 26 illustrates a cross-sectional view of another reservoir having an external shell according to an embodiment of the present invention.

FIG. 25 illustrates a reservoir 2500 with an outer protective layer 2505. The outer protective layer 2505 may be an exoskeleton configured to wrap axially about the reservoir 2500. The outer protective layer 2505 may protect the reservoir 2500 from external forces. As shown, the outer protective layer 2505 may include a hinge cut 2510 causing a gap within the outer protective layer 2505. The hinge cut 2510 may allow the outer protective layer 2505 to be deformable, thereby allowing the reservoir 2500 to be compliant even after the fluid-volume level of the reservoir 2500 causes the outer diameter of the reservoir 2500 to exceed the inner diameter of the outer protective layer 2505. In other words, the hinge cut 2510 allows the outer protective layer 2505 to expand (increasing the width of the gap), which in turn allows the reservoir 2500 to continue to expand as it receives additional fluid. FIG. 25A is a cross-sectional view of the reservoir 2500 having the separate, overlaying outer protective layer 2505. In one embodiment, the reservoir 2500 may be attached or integrated with the outer protective layer 2505 (e.g., by using an adhesive). The outer protective layer 2505 may further be used with reservoirs of different shapes. For example, FIG. 26 illustrates a cross sectional view of an outer protective layer 2605 surrounding a u-shaped reservoir 2600. As shown, the outer protective layer 2605 may include an optional hinge cut 2610.

As discussed herein, the reservoirs (e.g., reservoir 2500 of FIG. 25 and reservoir 2600 of FIG. 26, among other embodiments of reservoirs) may be shaped differently. In addition and/or alternatively, the reservoirs may include depressions, pleatings or longitudinal structures along an outer circumferential perimeter. For example, FIG. 27 illustrates a reservoir 2700 having four patterned depressions 2705 which may buckle (inward) in a reproducible manner when suction is applied to the reservoir 2700 by a surgical trocar (not shown). However, other depression patterns are also possible. For example, FIG. 28 illustrates a cross section of a reservoir 2800 having eleven patterned depressions 2805. FIG. 29 illustrates a cross section of a reservoir 2900 having three patterned depressions 2905. While FIGS. 27-29 illustrate reservoirs 2700, 2800 and 2900 having equally spaced depressions of different depths, non-uniformly spaced depressions are also possible for the purpose of guiding deflation.

Figure 30A:
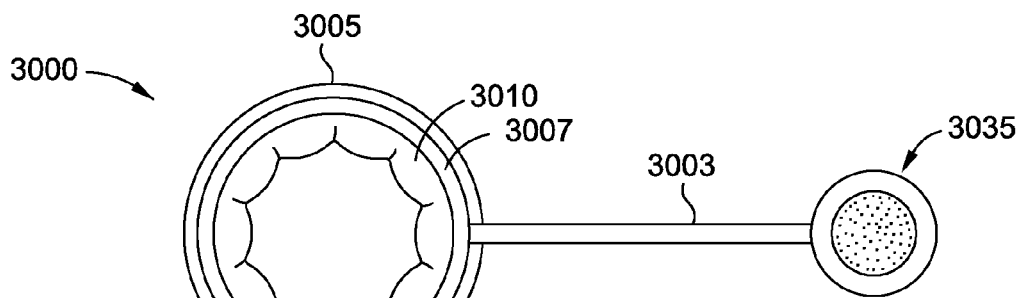
FIG. 30A illustrates a top view of a gastric banding system having a compliant reservoir about the circumference of the gastric band according to an embodiment of the present invention.
Figure 30B:
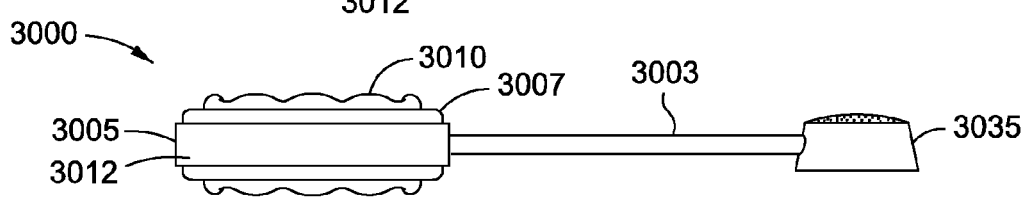
FIG. 30B illustrates a side view of the gastric banding system of FIG. 30A according to an embodiment of the present invention.

In addition and/or as an alternative to different reservoir shapes, a reservoir may be oriented in different ways. FIG. 30A illustrates one embodiment of a compliant reservoir system 3000 which may include a gastric band 3005 having an inflatable portion 3010, a ring 3007 and a compliant portion 3012. The gastric band 3005 may be fluidly coupled to a tubing 3003 and an access port 3035. As shown, the compliant reservoir 3012 may be oriented circumferentially about the ring 3007. The compliant reservoir 3012 may be in fluid communication (not shown) with the inflatable portion 3010 through a hole or other path (e.g., extending across the ring 3007). Accordingly, when a large bolus is swallowed by the patient, the fluid within the inflatable portion 3010 may be dispersed and may flow into the compliant reservoir 3012, thereby allowing the large bolus to pass through. Similar to the reservoirs 910, 1010, 1110 and 1250 of FIGS. 9-12, the compliant reservoir 3012 may be constructed of biocompatible, elastomeric material. FIG. 30B is a side view of the compliant reservoir system 3000 of FIG. 30A.

Figure 31:
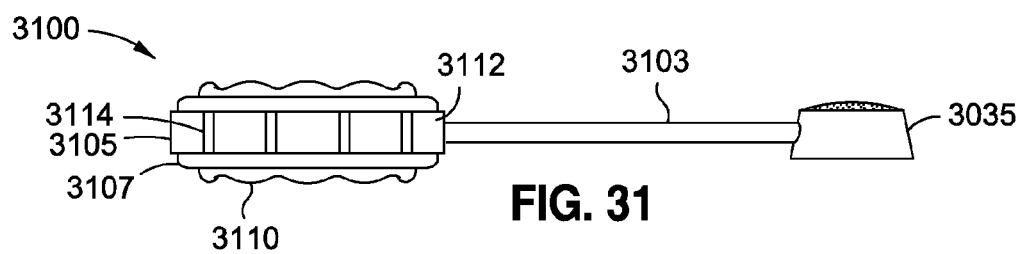
FIG. 31 illustrates a side view of a gastric banding system of having a compliant reservoir about the circumference of the gastric band according to an embodiment of the present invention.

Similar to the compliant reservoir system 3000, a compliant reservoir system 3100 may include a gastric band 3105 having an inflatable portion 3110, a ring 3107 and a compliant portion 3112. The gastric band 3105 may be fluidly coupled to a tubing 3103 and an access port 3135. However, as shown in FIG. 31, the compliant reservoir system 3100 may further include vertical molding portions 3114. The vertical molding portions 3114 may be equally spaced apart about the outer circumference of the compliant reservoir 3112 and may, in one embodiment, be attached to the ring 3107, functioning to provide the compliant reservoir 3112 with structural support. In this manner, the compliant reservoir 3112 may be integrated with the ring 3107.

Figure 32:
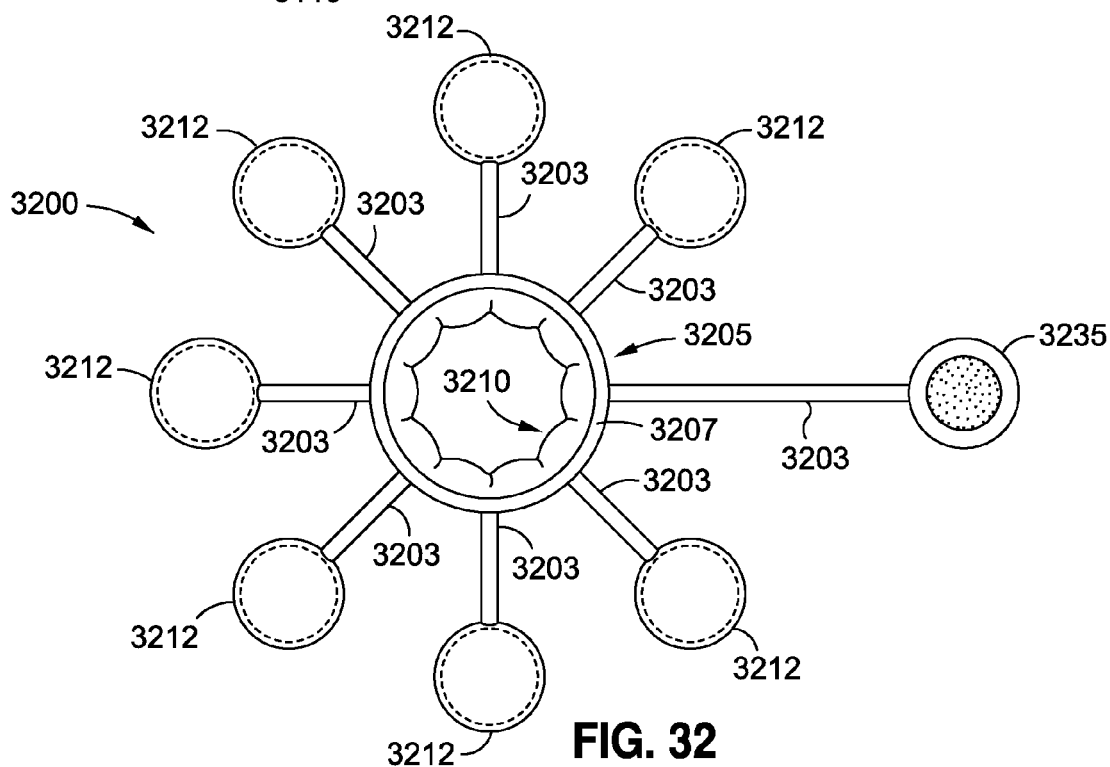
FIG. 32 illustrates an orientation of a gastric banding system having a plurality of reservoirs extending radially from the gastric band according to an embodiment of the present invention.

FIG. 32 illustrates a compliant reservoir system 3200 having a gastric band 3205 with an inflatable portion 3210 and a ring 3207. The gastric band 3205 may in fluid communication with an access port 3235 and a plurality of compliant reservoirs 3212. As shown, seven reservoirs 3212 may be oriented radially around the gastric band 3205 and may be coupled to the gastric band 3205 via corresponding tubing 3203. While each reservoir 3212 is shown to be substantially equidistant from the gastric band 3205, alternative geometries are possible (e.g., one or more of the reservoirs 3212 may be closer to the gastric band 3205 via shorting tubing). In addition, the number of reservoirs 3212 may vary (e.g., any number of reservoirs 3212 between one and twenty inclusive, may be included). These reservoirs 3212 may function similarly as the reservoirs 3012 and 3112 of FIGS. 30A and 31, respectively. For example, when a large bolus is swallowed by the patient, the fluid within the inflatable portion 3210 may be dispersed and may flow into any or all of the compliant reservoirs 3212, thereby allowing the large bolus to pass through. In addition, the reservoir 3212 may be constructed out of any one or a combination of biocompatible, elastomeric material.

Reservoirs of different types, configurations, and orientations having been discussed, attention will now be turned to the fill substance of the gastric banding systems. The fill substances discussed herein may be applicable to any gastric banding system, including any of the compliant reservoir systems discussed above (e.g., systems 900, 1000, 1100, and 1200).

Figure 33A:
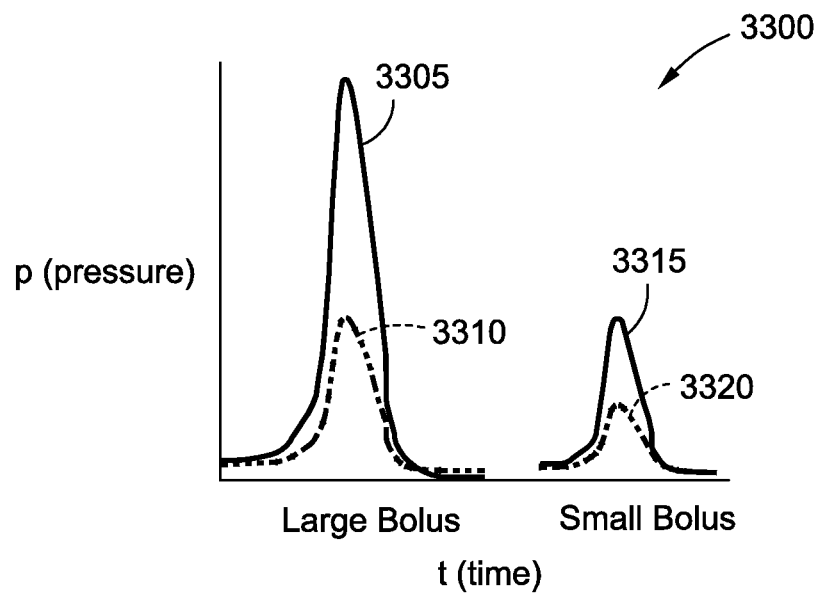
FIG. 33A illustrates a large bolus/small bolus pressure-time graph for two distinct gastric banding systems.

FIG. 33A illustrates a pressure-time graph 3300 comparing a compliant reservoir system utilizing saline or another fluid with a non-compliant gastric banding system. As shown, when a large bolus passes through the constriction of a non-compliant gastric banding system, a large spike in pressure 3305 is exerted whereas the same large bolus passing through the constriction of a compliant reservoir system utilizing saline may result in a lower pressure spike 3310. In addition, a higher pressure spike 3315 may occur when a small bolus passes through the constriction of the non-compliant gastric banding system, and a lower pressure spike 3320 may occur when the same small bolus passes through the constriction of the compliant reservoir system utilizing saline.

While FIG. 33A illustrates the benefits of a compliant reservoir system utilizing saline for situations where a large bolus is present over a non-compliant gastric banding system, further improvement may be possible with respect to small bolus reactions.

Figure 33B:
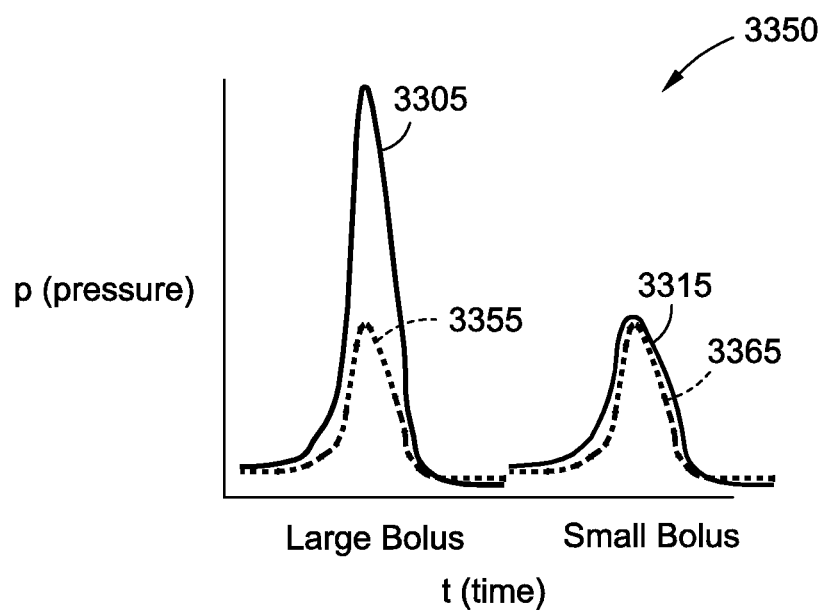
FIG. 33B illustrates a large bolus/small bolus pressure-time graph for two distinct gastric banding systems.

FIG. 33B illustrates a pressure-time graph 3350. The pressure-time spikes 3305 and 3315 correspond to a large bolus and a small bolus, respectively, passing through a constriction formed by a non-compliant gastric banding system. In comparison, the pressure spikes 3355 and 3365 correspond to a large bolus and a small bolus, respectively, passing through a constriction formed by a compliant reservoir system utilizing non-saline substances. More particularly, when a large bolus is introduced, the compliant reservoir system utilizing non-saline substances may perform substantially similar to a compliant reservoir system utilizing saline substances (e.g., comparing pressure spike 3310 of FIG. 33A and pressure spike 3355 of FIG. 33B). However, when a small bolus is introduced, the compliant reservoir system utilizing non-saline substances may perform substantially similar to a non-compliant reservoir system (e.g., comparing pressure spike 3315 of FIG. 33A and pressure spike 3365 of FIG. 33B). The response to large boluses and small boluses as illustrated in pressure spike 3355 and 3365, respectively, may be preferable for providing overall improved efficacy.

These non-saline substances which provide for the preferred pressure spikes 3315 and 3365 of FIG. 33B may include a pseudoplastic fluid, a Bingham plastic, and the like.

In one embodiment, a pseudoplastic fluid may be utilized to fill a gastric banding system (e.g., gastric banding system 500, 600). A pseudoplastic fluid may exhibit a decrease in viscosity under increases in the shear rate. Accordingly, only a slight increase in pressure would lead to relatively low shear rates (and relatively high viscosity) while a more substantial increase in pressure would lead to relatively high shear rates (and relatively low viscosity). In this manner, small to medium increases in pressure within the gastric banding system (e.g., gastric banding system 500, 600) will yield results similar to existing non-compliant gastric banding systems, while under higher pressure spikes, the pseudoplastic fluid (due to its lower viscosity at higher pressures) would flow out of the inflatable portions and into a reservoir, curbing the intensity of the pressure spike. Such large pressure spike may occur, for example, when a large bolus is attempting to pass through a constriction of the non-compliant gastric banding system. Once the pressure minimizes and the baseline pressure in the gastric banding system is re-established, the pseudoplastic fluid may gradually return to the inflatable portions.

In one embodiment, a Bingham plastic may be utilized as the fluid within the gastric banding system (e.g., gastric banding systems 500, 600). The Bingham plastic may be a material which does not flow until a minimum yield stress within the fluid is reached. In other words, prior to reaching the minimum yield stress, the Bingham plastic acts as a solid. However, once the minimum yield stress is reached, the Bingham plastic acts a fluid and may flow from the inflatable portions (e.g., the inflatable portion 510, 610) to a fluidly-coupled reservoirs (e.g., the reservoir 514, 614). Once the pressure minimizes and the baseline pressure is re-established, the Bingham plastic may flow again and may return to the inflatable portions (e.g., inflatable portions 510, 610).

In addition to pseudoplastic fluid, the Bingham plastic and the like, other materials may be used to fill any gastric banding system. Moreover, other configurations, including addition or removing various components of the gastric banding system, may be desirable when other fill substances are considered.

Figure 34A:
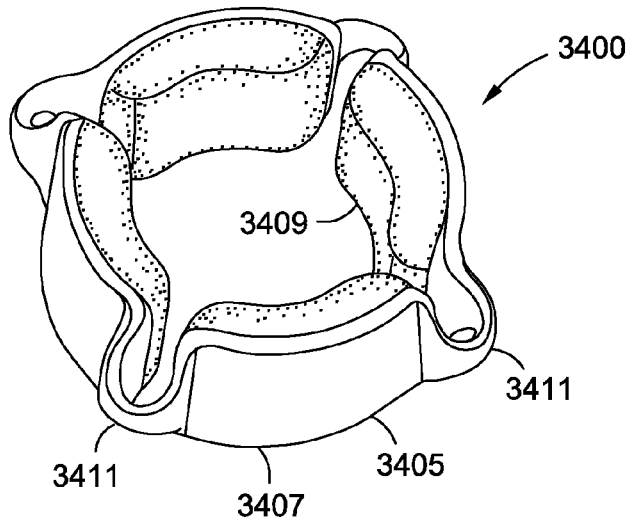
FIG. 34A illustrates a perspective view of a self-contained gastric banding system according to an embodiment of the present invention.

FIG. 34A illustrates a perspective view of one embodiment of a gastric band system 3400 having a different fill material than saline. The gastric band system 3400 may form a circumference about an upper stomach region of a patient and may provide pressure on the patient's stomach to induce satiety. Here, the gastric band system 3400 may include a gastric band 3405 having an outer ring 3407, cushions 3409 and one or more hinges 3411. The cushions 3409 may be filled with a gel and/or other substances. Alternatively or in addition, the cushions 3409 may be low durometer foam pads (e.g., less than 40 durometers). The gastric band 3405 may be self-contained and might not involve fluid systems having components such as tubing and access ports. As shown, the gastric band 3405 may include four cushions 3409 separated by four hinges 3411. However, additional cushions 3409 and/or hinges 3411 may be added, or one or more cushions 3409 and/or hinges 3411 may be removed. The hinges 3411 and the outer ring 3407 may be constructed out of a plastic or other polymer having dimensional stability, low creep and relatively high modulus of elasticity such that it may operate to function as a torsion spring. For example, a PEEK or polysufone material may be utilized, among other materials. Alternatively, the hinges 3411 may be constructed out of metal (e.g., stainless steel, titanium, etc.). In one or more embodiments, when the hinge 3411 is constructed out of a metal, a silicone rubber may encapsulate the hinge 3411. Regardless of the construction of the hinge 3411, each may function as a torsion spring generating a substantially constant force on the patient's stomach even when the inside diameter of the gastric band 3405 increases due to the passage of a large bolus of food. For example, as the radial expansion of the gastric band 3405 occurs as caused by the passing of the large bolus of food, an increase in the lever arm of the hinges 3411 partially opposes (and thus cancels out) the effect of the increasing deflection, thereby resulting in a constant force.

Figure 34B:
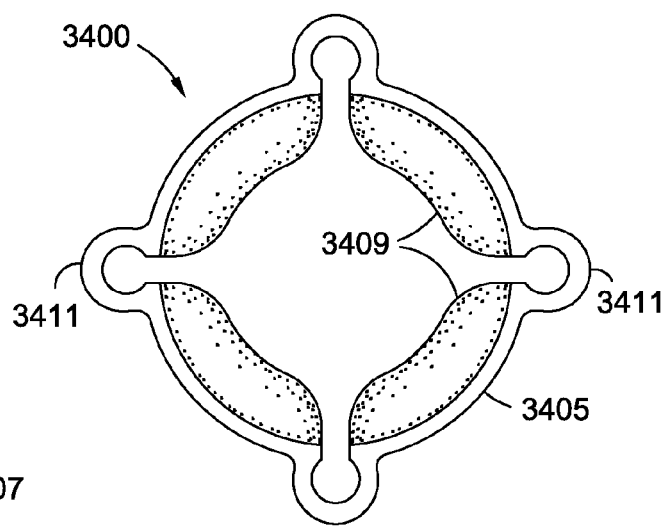
FIG. 34B illustrates a top view of the self-contained gastric banding system of FIG. 34A according to an embodiment of the present invention.

FIG. 34B illustrates a top view of the gastric banding system 3400 of FIG. 34A. As shown, in one embodiment, the hinges 3411 may be integrated with the outer ring 3407 and the cushions 3409 may have a length substantially spanning a non-hinge portion of the outer ring 3407. The gastric banding system 3400 of FIGS. 34A and 34B may include a tunable hoop spring rate and may be customized to have an initial diameter for a given patient.

Figure 35:
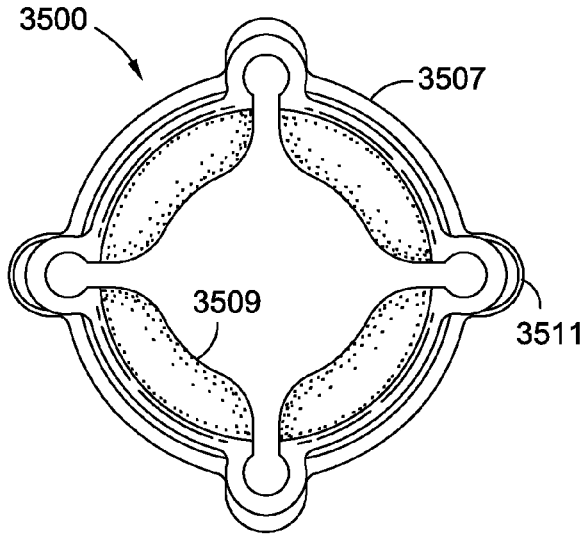
FIG. 35 illustrates a top perspective view of another self-contained gastric banding system according to an embodiment of the present invention.

FIG. 35 illustrates a gas-filled gastric banding system 3500. While similar in appearance to the gastric banding system 3400 of FIGS. 34A and 34B, and including features like one or more hinges 3511 and one or more ring portions 3507, one difference between the gas-filled gastric banding system 3500 and the gastric banding system 3400 is that the cushions 3509 may be constructed out of different materials and may be filled with one or more gases including carbon dioxide, nitrogen, among others. By utilizing the gas-filled cushions 3509, lower radial stiffness may be achieved, thereby reducing discomfort for the patient when a large bolus attempts to pass through the constriction. A suitable gas-impermeable membrane may be used in constructing the cushions 3509 to prevent the gas from leaking out. For example, a silicone rubber may be used. In addition, coatings to further prevent gas leakage such as a diamond-like carbon, titanium nitrite, parylene, aclar, among other gas impermeable substances, and combinations thereof may be applied to the silicone rubber. In one embodiment, the gastric banding system 3500 might not require a traditional access port for occasional adjustment. Instead, an adjustment just prior to implantation may provide a constant pressure configured to serve the constriction and/or the neural stimulation function properly while large boluses of food are able to pass through due to the compressibility of the gas-filled gastric banding system 3500.

Figure 36:
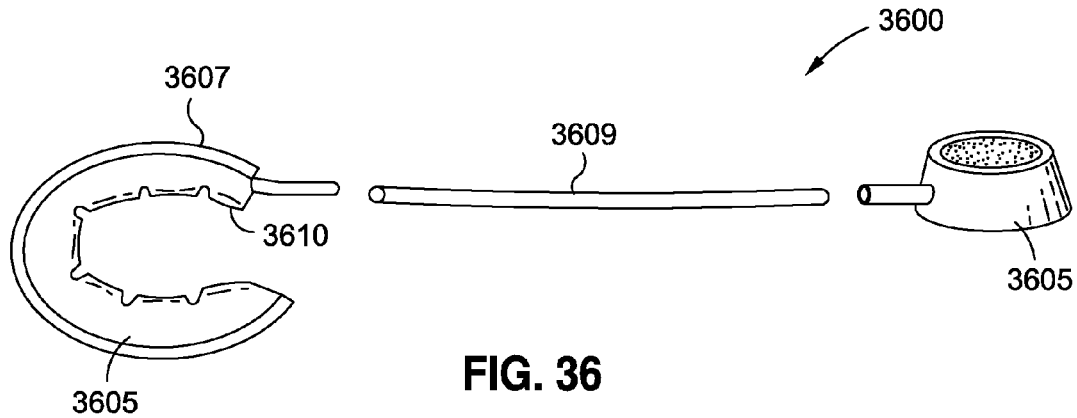
FIG. 36 illustrates an exploded, perspective view of a gastric banding system having gas-impermeable components according to an embodiment of the present invention.

The use of gas as a fill substance is not limited to the embodiment of FIG. 35. For example, as shown in FIG. 36, a gastric banding system 3600 may include a gastric band 3605 having a ring 3607 and an inflatable portion 3610 connected to a tube 3609 and an access port 3635. However, the inflatable portion 3610, the tube 3609 and the access port 3635 may all be constructed out of gas impermeable substances such as silicone rubber and/or coated with gas impermeable substances including, but not limited to, a diamond-like carbon, titanium nitrite, parylene, aclar, among other gas impermeable substances and combinations of substances.

Figure 37A:
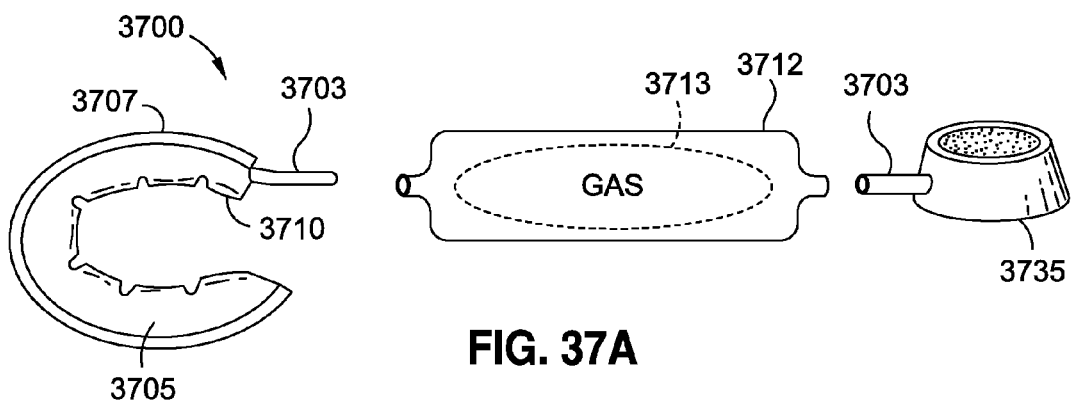
FIG. 37A illustrates an exploded, perspective view of a hybrid gas-fluid gastric banding system having gas-impermeable components according to an embodiment of the present invention.

In a further embodiment, a hybrid gas-saline gastric banding system 3700 is illustrated in FIG. 37A. As shown, the hybrid gas-saline gastric banding system 3700 may include a gastric band 3705 having a ring 3707 and an inflatable portion 3710. The gastric band 3705 may be in fluid communication with a reservoir 3712 and an access port 3735 via tubing 3703. The gastric banding system 3700 may be filled with a standard saline solution. However, a further encapsulated member 3713 may also be present within the hybrid gas-saline gastric banding system 3700. The encapsulated member 3713 may be a balloon filled with a gas such as carbon dioxide, nitrogen, and the like. The encapsulated member 3713 may function to further provide flexibility and/or otherwise lower the radial stiffness within the hybrid gas-saline gastric banding system 3700 by moving from the inflatable portion 3710 to the reservoir 3712 when a large bolus is attempting to pass through the constriction of the gastric band 3705. In one embodiment, the encapsulated member 3713 is within the fluid path and may travel to any component of the gastric banding system 3700 in response to fluid movement through, e.g., the tubing 3703. In one embodiment, the encapsulated member 3713 may be configured to be located within or traverse back into the inflatable portion 3710 when a large bolus is not attempting to pass through (e.g., when the hybrid gas-saline gastric banding system 3700 is in an equilibrium state).

In one embodiment, the encapsulated member 3713 may be constructed out of silicone rubber and may be coated with one or more materials to enhance the ability of the silicone rubber to be gas impermeable thereby preventing the encapsulated member 3713 from leaking.

In one embodiment, the encapsulated member 3713 might not be designed to not fit through the tubing 3703 and traverse between the different components of the hybrid gas-saline gastric banding system 3700. In other words, the encapsulated member 3713 may permanently reside in any one of the components, e.g., the reservoir 3712.

Figure 37B:
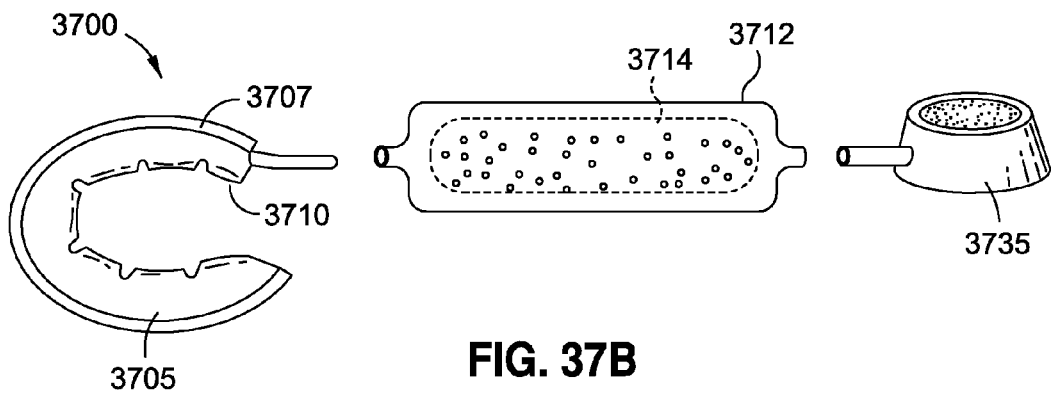
FIG. 37B illustrates an exploded, perspective view of a hybrid foam-fluid gastric banding system having gas-impermeable components according to an embodiment of the present invention.

FIG. 37B illustrates the hybrid gas-saline gastric banding system 3700 utilizing a different encapsulated member 3714 in place of the encapsulated member 3713 of FIG. 37A. The encapsulated member 3714 may have the functionality similar to the encapsulated member 3713 of FIG. 37A, but may be constructed out of a closed cell foam instead of gas.

Modifications may be further made to the hybrid gas-saline gastric banding system 3700. For example, other compliant portions may be added. Alternatively and/or in addition, in one embodiment, the hybrid gas-saline gastric banding system 3700 as discussed above with respect to FIGS. 37A and 37B may be further modified to eliminate the access port 3735 leaving only the gastric band 3705, the reservoir 3712 and one of the encapsulated members 3737 or 3738 (not shown). Eliminating the access port 3735 renders the hybrid gas-saline gastric banding system 3700 self-adjusting and may provide constant pressure on the stoma of the patient.

Figure 38A:
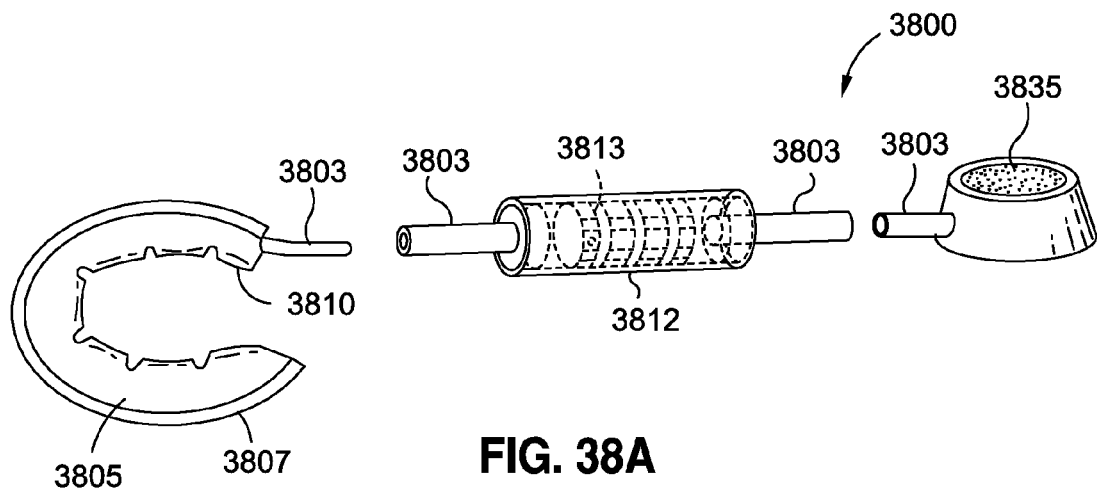
FIG. 38A illustrates an exploded, perspective view of a hybrid gas-fluid gastric banding system having a gas-spring according to an embodiment of the present invention.

FIG. 38A illustrates another embodiment of a hybrid gas-saline gastric banding system 3800. As shown, the hybrid gas-saline gastric banding system 3800 may include a gastric band 3805 having a ring 3807 and an inflatable portion 3810. The gastric band 3805 may be in fluid communication with a reservoir 3812 and an access port 3835 via tubing 3803. The gastric banding system 3800 may be filled with a standard saline solution. The reservoir 3812 may be cylindrical in shape and may be constructed out of a silicon rubber or another durable, gas impermeable material. The tubing 3803 may be held in place within the reservoir 3812 by an adhesive layer or patch. In addition, the reservoir 3812 may house a gas spring 3813. In one embodiment, the gas spring 3813 may be retained in the reservoir 3813 by radial interference (e.g., the gas spring 3813 may be designed to fit tightly within the reservoir 3812 to avoid slippage or other un-intended movement). In one embodiment, the gas spring 3813, while being movably fixed within the reservoir 3812, may still allow for fluid to pass through by having uneven surfaces (e.g., non-circular geometry which creates gaps and/or openings for fluid to pass through between an outside surface of the gas spring 3813 and an inner diameter of the reservoir 3812). Generally, the gas spring 3813 may operate to provide volume flexibility and/or low radial stiffness in the gastric banding system 3800. For example, when a large bolus of food passes through a constriction of the gastric band 3805, pressure caused by the bolus on the inflatable portion 3810 may cause a transfer of fluid from the inflatable portion 3810 to the reservoir 3812. One function of the gas spring 3813 is to alleviate the pressure spike caused by the food bolus by moving a piston within the gas spring 3813 and winding the gas spring 3813. Once the pressure is removed (e.g., the bolus having been passed through the constriction), the gas spring 3813 may unwind and revert back to a non-compressed orientation.

Figure 38B:
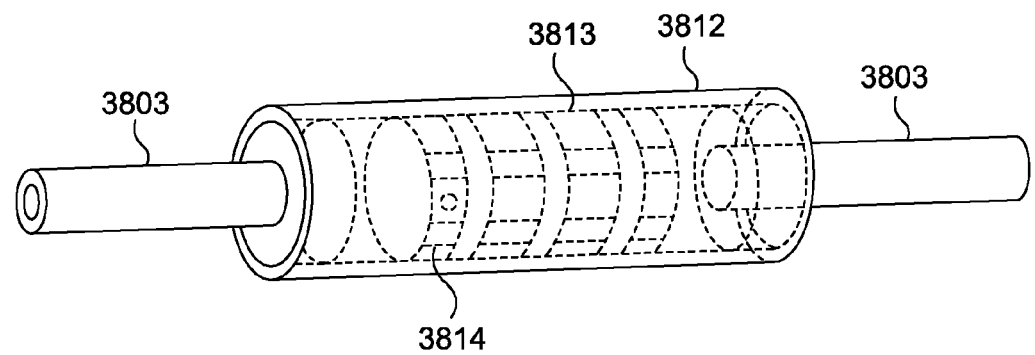
FIG. 38B illustrates a close-up view of the gas-spring within a reservoir of FIG. 38A according to an embodiment of the present invention.
Figure 38C:
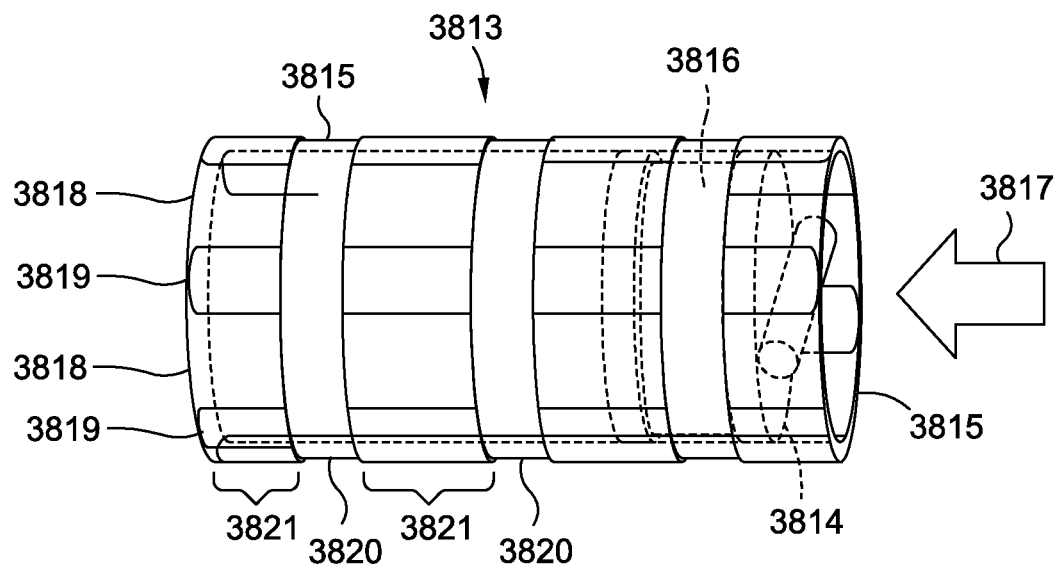
FIG. 38C illustrates a close-up view of the gas-spring of FIG. 38A according to an embodiment of the present invention.

FIG. 38B illustrates the reservoir 3812 and the gas spring 3813 apart from the other portions of the hybrid gas-saline gastric banding system 3800. FIG. 38C illustrates a further deconstructed view of the gas spring 3813 apart from the reservoir 3812. As shown in FIG. 38C, a pin 3814 may be fixed in place to the inner diameter of the gas spring housing 3815 thereby limiting the movement of the piston 3816. Arrow 3817 illustrates a direction of fluid pressure (e.g., caused by a large bolus passing through the constriction of the gastric band 3805) which may move the piston 3816 and compress the gas within the gas spring housing 3815. The gas within the gas spring housing 3815 may be sealed between the piston 3816 and compressed when pressure is introduced. In one embodiment, the piston 3816 and the inner surface of the gas spring housing 3815 may be formed out of materials with very low coefficient of friction such that the overall friction force does not overly prevent the piston 3816 from moving when a fluid pressure is introduced. In one embodiment, the outside surface of the gas spring housing 3815 may include contact segments 3821 and fluid passageway segments 3820 configured in an alternating manner. An outer diameter of any given fluid passageway segment 3820 may be smaller than an outer diameter of any given contact segment 3821. The contact segments 3821 may further include curved portions 3818 for contacting an inner diameter of the reservoir 3812 of FIG. 38B, thereby holding or fixing the gas spring 3813 in place. The contact segments 3821 may further include flat portions 3819 which might not contact the inner diameter of the reservoir 3812, thereby allowing fluid flowing through the fluid passageway segment portions 3818 to also flow through the contact segments 3821. In this manner, fluid within the gastric banding system 3800 may flow from, for example, the gastric band 3805 to the access port 3835, and vice versa. In one embodiment, the flat portions 3819 and the curved portions 3813 of each contact segment 3821 may alternate in configuration around the circumference of the gas spring housing 3815.

Figure 38D:
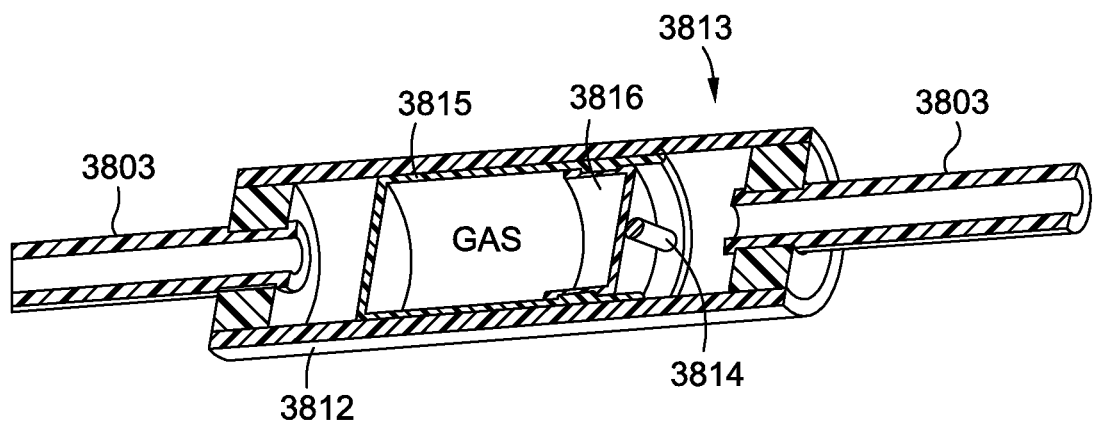
FIG. 38D illustrates a cross-sectional view of the gas-spring of FIG. 38A according to an embodiment of the present invention.

FIG. 38D is a cross-sectional view of the reservoir 3812 and the gas spring 3813 apart from the other portions of the hybrid gas-saline gastric banding system 3800 to better illustrate the configuration of the components therein. Appropriate materials to construct one or more parts of the gas spring 3813 (e.g., gas spring housing 3815, piston 3816, etc.) may include gas-impermeable and/or saline-impermeable substances such as plastics like PTFE.

In addition to and/or as an alternative to a hybrid gas-saline gastric banding system of FIG. 38 having a reservoir (e.g., the reservoir 3812) functioning as the gas-saline component, other components of the gastric banding system may be the gas-saline component. For example, an access port of any gastric banding system may be the gas-saline component.

Figure 39:
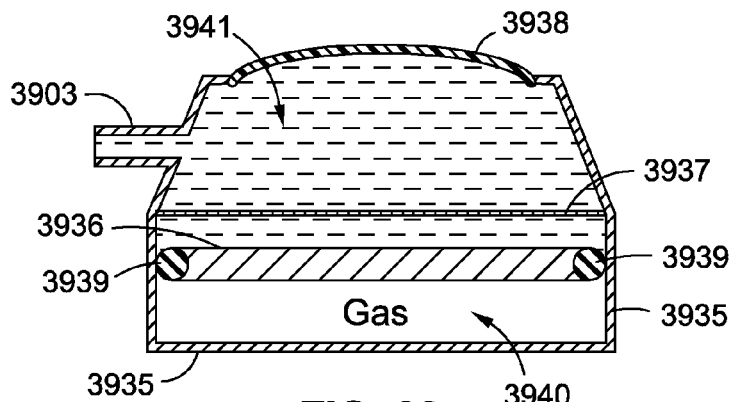
FIG. 39 illustrates a close up view of an access port for a gastric banding system according to an embodiment of the present invention.
Figure 40:
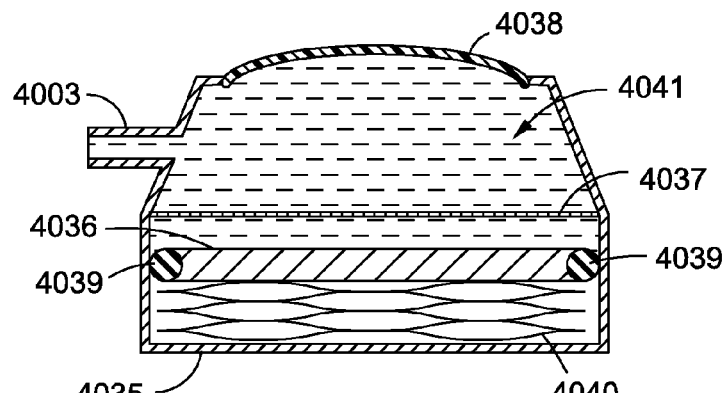
FIG. 40 illustrates a close up view of another access port for a gastric banding system according to an embodiment of the present invention.
Figure 41:
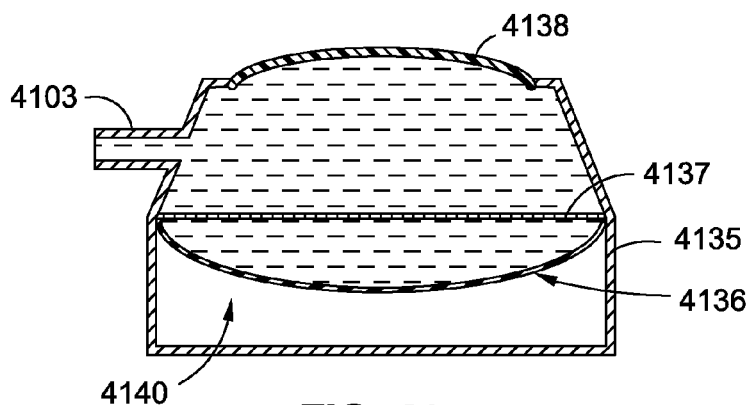
FIG. 41 illustrates a close up view of another access port for a gastric banding system according to an embodiment of the present invention.

FIGS. 39-41 illustrate various embodiments of access ports 3935, 4035, 4135. While the rest of the gastric banding system is not shown in these figures, the access ports 3935, 4035, 4135 may be in fluid communication with other components of the gastric banding system (e.g., a gastric band and/or a reservoir) via tubes 3903, 4003, 4103, respectively. For example, access ports 3935, 4003, 4103 may each be the access port 435 or 535.

Turning to FIG. 39, in one embodiment, the access port 3935 may include a movable surface 3936 which may move in response to a pressure change within the gastric banding system. For example, the movable surface 3936 may be a complaint portion that moves to increase the volume of the fluid portion 3941 (and therefore increases compliance) when the pressure increases within the gastric banding system (e.g., in response to a large bolus moving through a constriction of the gastric band). Once the pressure is reduced (e.g., the large bolus passing through the constriction), the movable surface 3936 may return to its original position, thereby decreasing the volume of the fluid portion 3941 of the access port 3935. The access port 3935 may further include a septum 3938, a fluid-permeable membrane 3937, o-rings 3939 and a gas spring portion 3940 filled with a gas 3935.

Alternatively, the gas spring portion 3940 may be replaced with a wave spring, a cantilever spring, a constant force spring, a coil spring, a leaf spring, a Belleville spring, a hybrid polymer coil-air spring and the like. In addition, a vacuum (not shown) may be incorporated in order to achieve the desired pressure response.

FIG. 40 illustrates an example of an access port 4035 having a wave spring 4040. The access port 4035 may be in fluid communication with other components of the gastric banding system (e.g., a gastric band and/or a reservoir) via tube 4003. In one embodiment, the access port 4035 may include a movable surface 4036 which may move in response to a pressure change. For example, the movable surface 4036 may be a complaint portion that moves to increase the volume of the fluid portion 4041 (and therefore increases compliance) in response to a large bolus moving through a constriction of the gastric band (not shown). Once the pressure is reduced (e.g., the large bolus passes through the constriction), the movable surface 4036 may return to its original position thereby decreasing the volume of the fluid portion 4041 of the access port 4035. The access port 4035 may further include a septum 4038, a fluid-permeable membrane 4037, o-rings 4039 and a wave spring 4040.

In one embodiment, the spring (e.g., gas spring 3940 of FIG. 39 or wave spring 4040 of FIG. 40) may be removed as shown in FIG. 41. Here, the moving surface 4136 may comprise a flexible membrane that deforms when subjected to pressures above a certain threshold (which in one example, may be set to approximate the pressure induced when a large bolus is passing through a constriction). Once the pressure falls below the threshold again (e.g., when the large bolus passes through the constriction), the moving surface 4136 may return to its original configuration. The moving surface 4136 may be constructed out of silicone or another biocompatible flexible polymer, among other materials. The moving surface 4136 may be attached to the inner wall of the access port 4135 or may be integrated with a septum 4138 of the access port 4135.

Each of the access ports 3935, 4035 and 4135 may include a corresponding septum 3938, 4038 and 4138. The septum 3938, 4038 and 4138 may function to allow a penetrating needle to add or remove fluid thereby adjusting the total fluid volume within the corresponding gastric banding system. In addition, the access ports 3935, 4035 and 4135 may include a corresponding fluid-permeable membrane 3937, 4037 and 4137 having a plurality of small openings (not shown) which may be large enough to allow fluid to pass through, but are small enough to prevent the passage of the needle. The fluid-permeable membranes 3937, 4037 and 4137 may be constructed out of a metal, ceramic, carbon, polymer or any combination thereof. Other materials may also be used so long as the material prevents the passage of the needle. The fluid-permeable membranes 3937, 4037 and 4137 may be attached to the inner wall of the corresponding access port 3935, 4035 and 4135.

In addition, the access ports 3935 and/or 4035 may include a corresponding sealing ring 3939 and 4039 to prevent fluid from entering the spring portions 3940 and 4040. The sealing rings 3939 and 4039 may be a polymer o-ring, a metal seal ring, a ceramic seal ring, a polymer seal ring and the like.

In addition to using pressure to control the flow of fluid, gas, among other substances within a gastric banding system, specific restriction devices may also be utilized. For example, a one-way valve, a pressure relief valve, orifices, turbulence controllers, sponges, environment-adapting devices, among other restriction devices may control a rate at which a component (e.g., a compliant reservoir) may receive fluid from another component (e.g., a gastric band).

Figure 42:
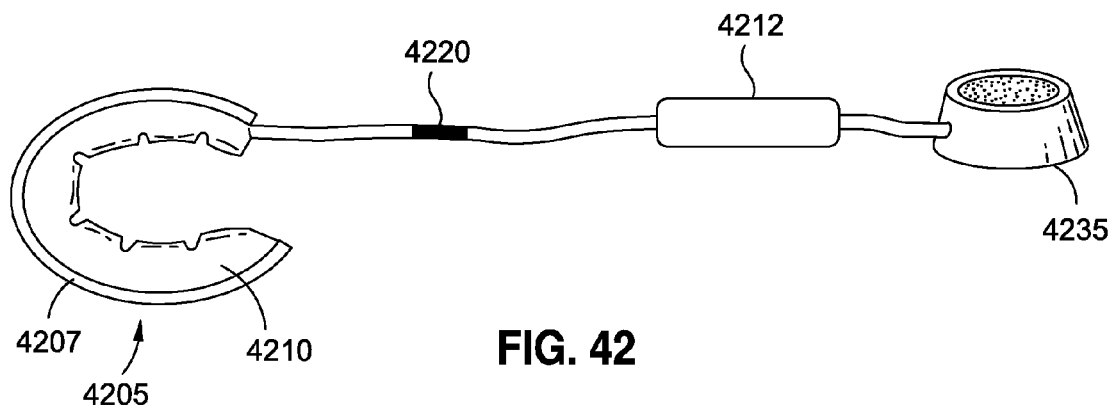
FIG. 42 illustrates a perspective view of a gastric banding system having a flow rate restrictor according to an embodiment of the present invention.

FIG. 42 illustrates an embodiment of a gastric banding system 4200 having a gastric band 4205, an inflatable portion 4210, and a ring 4207 in fluid communication with a reservoir 4212 through a restriction device 4220. Also shown is an access port 4235 in fluid communication with the above-mentioned components of the gastric banding system 4200. The restriction device 4220 may be electronically controlled, modulated with an external adjustment system or may be a passive restriction device configured to be independent from being controlled by an external tool or device.

Figure 43:
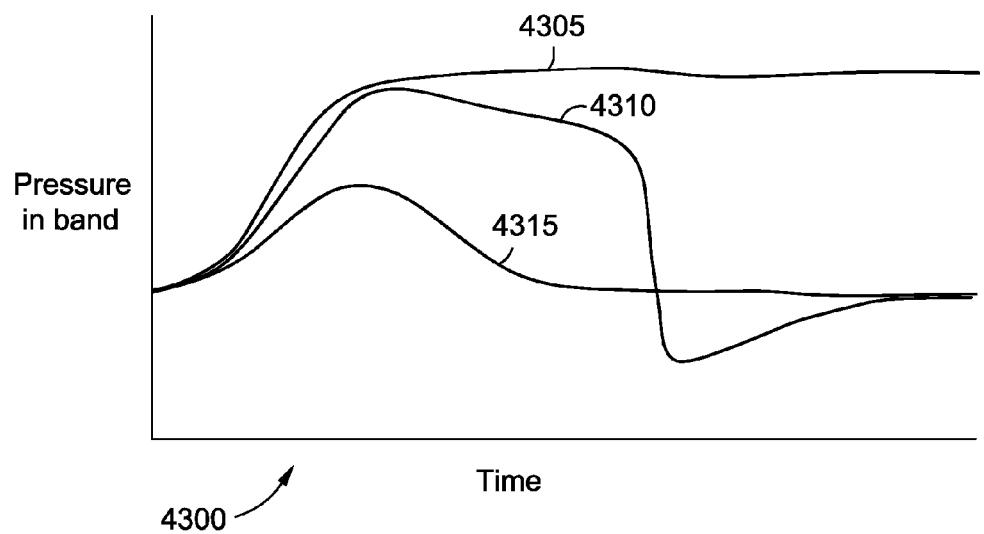
FIG. 43 illustrates a time-pressure curve for a gastric banding system without a flow rate restrictor and a time-pressure curve for a gastric banding system with a flow rate restrictor.

In practice, any one (or more) of a plurality of restriction devices (e.g., restriction device 4220) may be used within the fluid path of the gastric banding system 4200 or any other gastric banding system. Further, additional restriction devices may be added to achieve the desired flow rates. FIG. 43 illustrates a graph 4300 depicting how the time-pressure curve may change when such a restriction device 4220 is used (e.g., an orifice having an inner diameter which limits the flow rate of the fluid in both directions) in one embodiment. For comparison, line 4305 is a time-pressure curve corresponding to a standard non-compliant band. As shown, the pressure may sharply rise when a large bolus encounters the constriction formed by the standard non-compliant band may become obstructed. As shown, the pressure may remain high for the duration of the obstruction caused by the bolus, and the patient may experience discomfort for a long period of time. Line 4315 is a time-pressure curve corresponding to a compliant band without a restriction device. As shown, the large bolus of food may cause only a modest increase in pressure (and hence, lesser patient discomfort) as the bolus passes through a constriction formed by the compliant band without the restriction device. This illustrates a potential drawback in the compliant band without a restriction device as the patient might not be aware that he or she has eaten an inappropriately large piece of food.

Line 4310 is a time-pressure curve corresponding to a compliant band with a restriction device (e.g., as shown in FIG. 42). As shown by the line 4310, the pressure may rise quickly causing the patient to feel pressure for a short period of time as the fluid drains slowly from the band (e.g., the gastric band 4205) and into the reservoir (e.g., the reservoir 4212). After a short period of time (which may serve as a reminder to the patient to modify his or her eating pattern and to avoid eating large pieces of food) the band drains enough fluid into the reservoir to allow the bolus to pass through, thereby returning the pressure near equilibrium.

Balloons, reservoirs, access ports and flow control devices having been discussed, attention will now be turned to the gastric band portion of a gastric banding system.

Figure 44A:
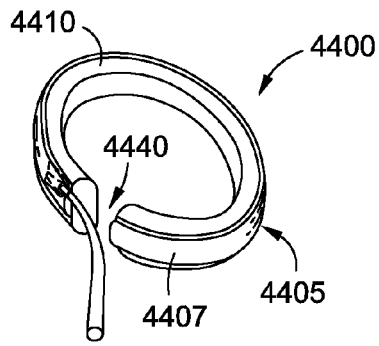
FIG. 44A illustrates an always-open gastric banding system according to an embodiment of the present invention.

FIG. 44A illustrates an embodiment of an always-open gastric banding system 4400 including a gastric band 4405 having a ring 4407 and an inflatable portion 4410. Instead of having a flexibly-stiff ring locked in place at an open end (as traditionally utilized in a standard gastric band), the gastric band 4405 does not include a locking portion and replaces the flexibly-stiff ring with a more inflexible ring (e.g., ring 4407) such as a snap ring, a split ring, retaining ring and the like. The more inflexible ring (e.g., the ring 4407) may be constructed out of metal and a corresponding spring rate may be adjusted to provide a substantially constant force on the outside of the patient's stomach. In one embodiment, the adjustability of the inflatable portion (e.g., the inflatable portions 4410) may be eliminated. As shown, in this embodiment of FIG. 44, the other components (access port, tubing, etc.) of a standard gastric band system may be removed. In operation, once the gastric banding system 4400 is implanted, the gastric band 4405 may flex open when a large bolus moves through the constriction of the gastric band 4405 on the stomach region. Once the large bolus passes the constriction of the gastric band 4405, the gastric band 4405 may return to its original orientation. As shown, the gastric banding system 4400 may include a variable width gap 4440 between the opposite ends of the gastric band 4405. The gap 4440 may serve to provide a more effective response to a patient's anatomy and physiological conditions (e.g., swallowing a large bolus).

Figure 44B:
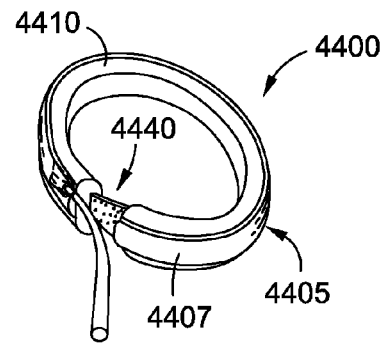
FIG. 44B illustrates an always-open gastric banding system having an elastic member according to an embodiment of the present invention.

FIG. 44B illustrates another embodiment of the gastric banding system 4400 of FIG. 44A. As shown, the gastric banding system 4400 further includes elastic members 4450, which may be tethered to "close" the variable width gap 4440. In this embodiment, the elastic members 4450 may be constructed out of a flexible polymer and may function to enhance the ability of the gastric banding system 4400 to remain in place.

Figure 45:
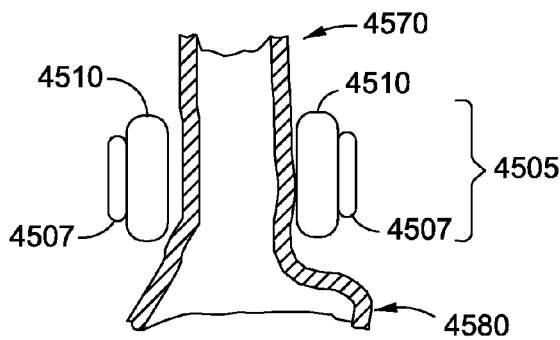
FIG. 45 illustrates a cross-sectional view of a gastric band located about an esophageal-gastric junction of a patient.

In addition to and/or as an alternative to gastric banding systems having an "open" configuration (e.g., the gastric banding system 4400), a gastric band may also be configured to have portions of various sizes. FIG. 45 illustrates a cross-sectional view of the standard gastric band 4505 having a ring 4507 providing structural support to an inflatable portion 4510. As shown, the standard gastric band 4505 is placed or fixed about the esophageal-gastric junction between a patient's esophagus 4570 and stomach 4580.

Figure 46:
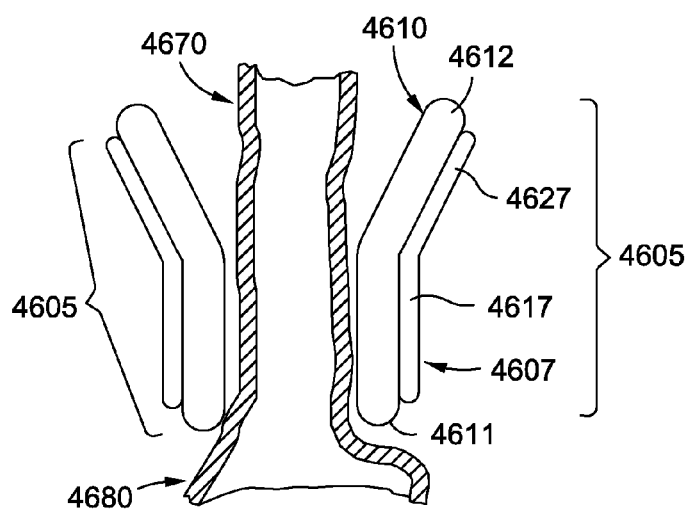
FIG. 46 illustrates a cross-sectional view of a gastric band having a funnel shape according to an embodiment of the present invention.

FIG. 46 illustrates an embodiment with a wider section. As shown in the cross-sectional view of FIG. 46, the improved gastric band 4605 may still include a ring 4607 and an inflatable portion 4610. However, the design of the ring 4607 may include a standard portion 4617 and a wider portion 4627, and the inflatable portion 4610 may include a corresponding standard portion 4611 and a corresponding wider portion 4612. The wider portions 4612 and 4627 may be placed orad (closer or toward the mouth of the patient) as compared to the standard portions 4611 and 4617. The wider portions 4612 and 4627 may operate to stimulate and restrict the patient's esophageal-gastric junction when the patient is not eating or swallowing small boluses. When the patient swallows medium-sized boluses, the wider portions 4612 and 4627 may channel the medium bolus through the standard portions 4611 and 4617. And when the patient swallows large boluses, the wider portions 4612 and 4627 may function to relieve the stress on the patient's tissue and assist to prevent formations of pouch dilatations. The wider portions 4612 and 4627, as shown in FIG. 46, may increase in diameter in the orad direction. Optional suture tabs (not shown) may also be added to the gastric band 4605, for example, when the additional width of the wider portions 4612 and 4627 render it preferable that a standard gastro-gastric suturing process is not used. In one embodiment, the wider portions 4612 and 4627 may be adjustable.

In one embodiment, the wider portions 4612 and 4627 may have the same properties as the standard portions 4611 and 4617 (e.g., same materials, durometer, balloon-to-ring width ratio). Additionally, and/or as an alternative, the height of the ring 4607 and/or the height of the inflatable portion 4610 may be adjustable and might not span the entire height of the gastric band 4600 (not shown).

Figure 47A:
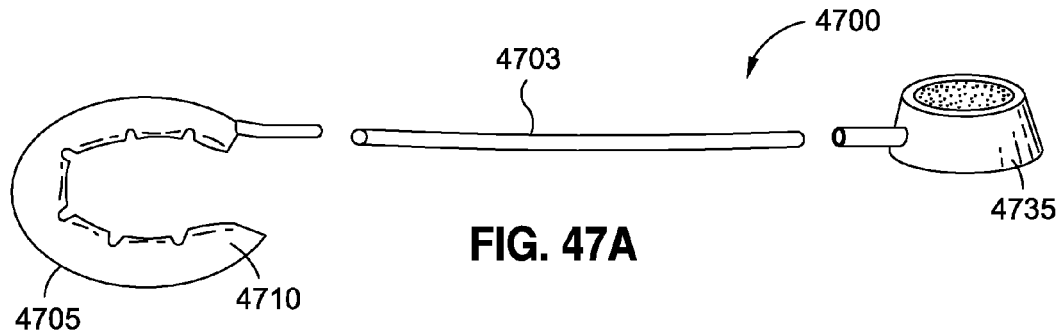
FIG. 47A illustrates an exploded, perspective view of a gastric banding system including a gastric band without a ring according an embodiment of the present invention.
Figure 47B:
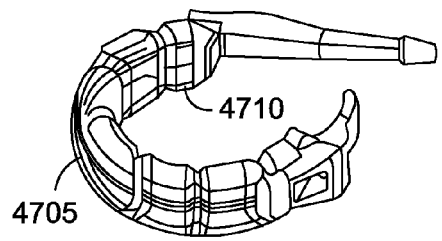
FIG. 47B illustrates a perspective view of the gastric band of FIG. 47A according to an embodiment of the present invention.

Further configurations of a gastric band system may include alterations to the ring portion. For example, FIG. 47A illustrates a gastric banding system 4700 having a gastric band 4705, a tube 4703 and an access port 4735. As shown, the gastric band 4705 may include an inflatable portion 4710 without the presence of a ring. By eliminating the ring, the gastric banding system 4700 may be more compliant. As shown, the gastric banding system 4700 may rely on the inflatable portion 4710 alone for ring structure. FIG. 47B illustrates a perspective view of the gastric band 4705 without the ring structure, and with the other structures of the gastric banding system 4700 omitted.

Figure 48A:
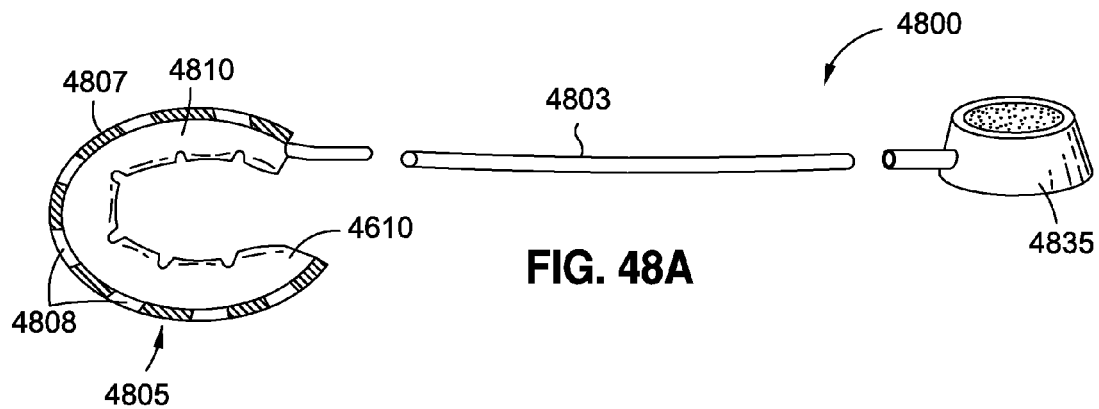
FIG. 48A illustrates an exploded, perspective view of a gastric banding system including a gastric band having a ring with holes according an embodiment of the present invention.
Figure 48B:
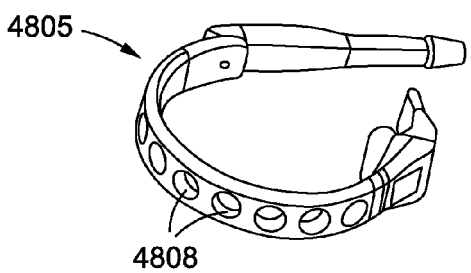
FIG. 48B illustrates a perspective view of the gastric band of FIG. 48A according to an embodiment of the present invention.

FIG. 48A illustrates another embodiment of a gastric banding system 4800 having a gastric band 4805, a tube 4803 and an access port 4835. As shown, the gastric band 4805 may include inflatable portion 4810 and modified ring 4807 having holed portions 4808. The addition of the holed portions 4808 may increase the compliance of the gastric banding system 4800. FIG. 48B illustrates a perspective view of the gastric band 4805 with holed portions 4808. The inflatable portion 4810 and the other structures of the gastric banding system 4800 have been omitted for clarity.

Figure 49A:
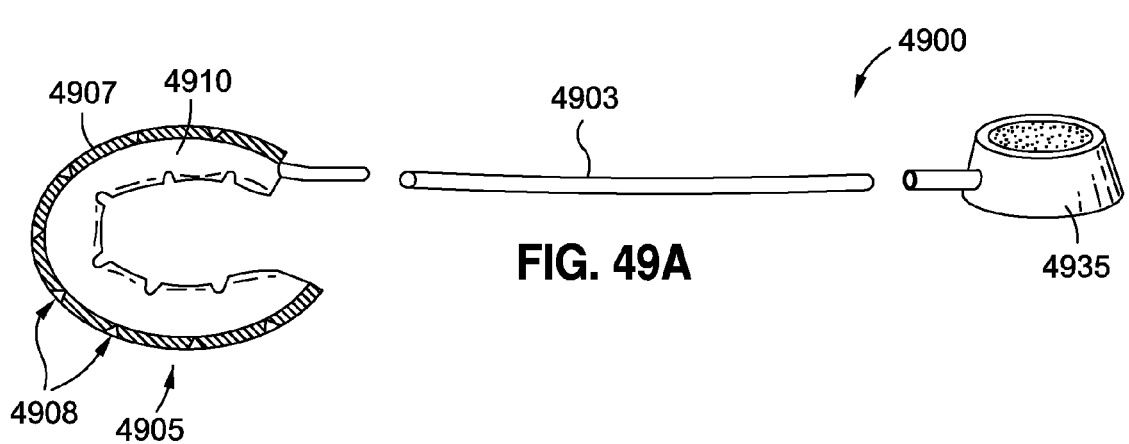
FIG. 49A illustrates an exploded, perspective view of a gastric banding system including a gastric band having a ring with cut-out portions according an embodiment of the present invention.
Figure 49B:
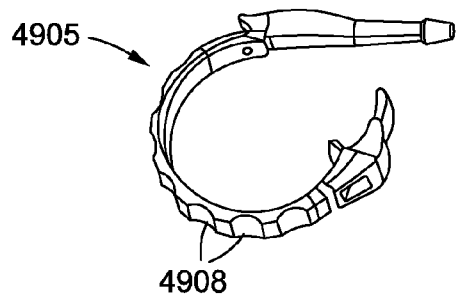
FIG. 49B illustrates a perspective view of the gastric band of FIG. 49A according to an embodiment of the present invention.

FIG. 49A illustrates another embodiment of a gastric banding system 4900 having a gastric band 4905, a tube 4903 and an access port 4935. As shown, the gastric band 4905 may include an inflatable portion 4910 and a modified ring 4907 having cut-out or tapered portions 4908. The cut-out or tapered portions 4908 may increase the compliance of the gastric banding system 4900. FIG. 49B illustrates a perspective view of the gastric band 4905 with the cut-out or tapered portions 4908. The inflatable portion 4910 and the other structures of the gastric banding system 4900 have been omitted for clarity.

The gastric bands 4705, 4805 and 4905 may be more flexible (e.g., by having decreased ring stiffness) than a standard gastric band, thereby resulting in gastric banding systems 4700, 4800 and 4900, respectively, having muted pressure or force spikes on the tissues (e.g., in the esophageal-gastric junction) in a patient when the patient consumes a large bolus of food. Furthermore, each of the gastric bands 4705, 4805 and 4905 may have different, configurable torsional and ring stiffness characteristics to further create an ergonomically ideal function to serve the patient.

Figure 50A:
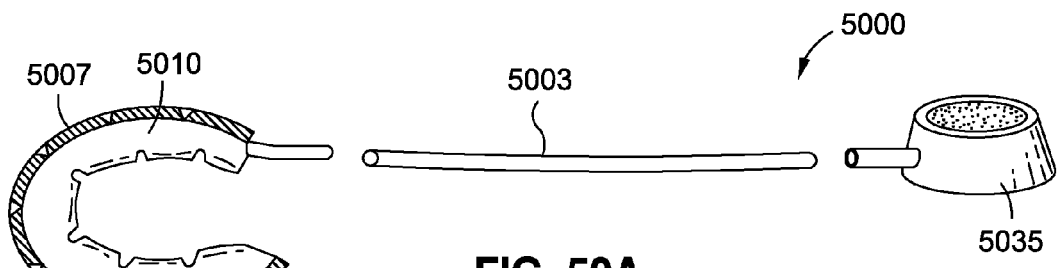
FIG. 50A illustrates an exploded, perspective view of a gastric banding system including a gastric band having a modified ring according an embodiment of the present invention.

In additional to gastric bands 4705, 4805 and 4905, a gastric band 5005 of a gastric banding system 5000 as illustrated in FIG. 50A may serve as another alternative providing the desired compliance performance curve. As shown, FIG. 50A of the gastric banding system 5000 includes the gastric band 5005, a tube 5003 and an access port 5035. The gastric band 5005 may also include an inflatable portion 5010 and a modified ring 5007 having a modified surface texture/topography. The modified surface texture/topography may increase the compliance of the gastric banding system 5000.

Figure 50B:
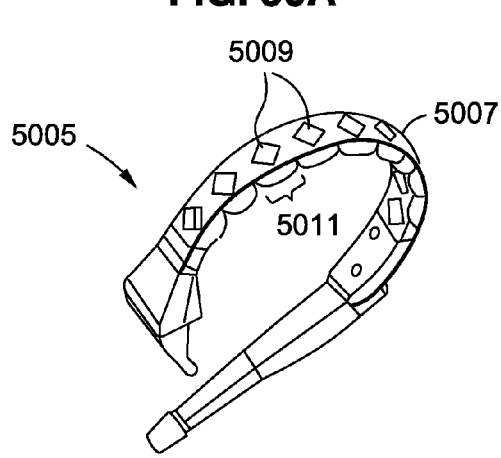
FIG. 50B illustrates a perspective view of the gastric band of FIG. 50A according to an embodiment of the present invention.

FIG. 50B illustrates a perspective view of the gastric band 5005 with the modified surface texture/topography of the modified ring 5007. The inflatable portion 5010 and the other structures of the gastric banding system 5000 have been omitted for clarity. In this example, the modified surface texture/topography may be a combination of a uniform set of diamond-shaped indentions or apertures 5009 along a length of the ring 5007 such that each diamond-shaped indention or aperture 5009 correlates with a different, inwardly-tapered segment-like portion 5011 of the ring 5007.

Figure 51A:
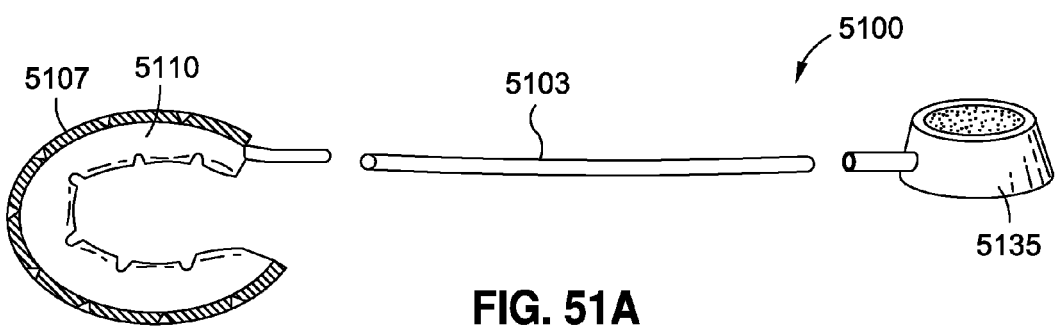
FIG. 51A illustrates an exploded, perspective view of a gastric banding system including a gastric band having a modified ring according an embodiment of the present invention.

FIG. 51A may serve as another alternative providing the desired compliance performance curve. As shown, the gastric banding system 5100 includes a gastric band 5105, a tube 5103 and an access port 5135. The gastric band 5105 may also include an inflatable portion 5110 and a modified ring 5107 having a tapered or thin body portion. The tapered body portion may increase the compliance of the gastric banding system 5000 by increasing the flex of the ring 5107.

Figure 51B:
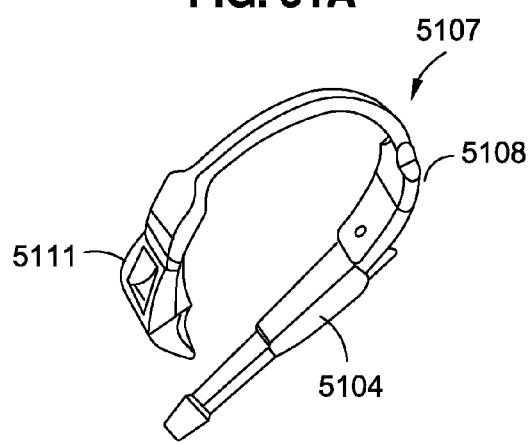
FIG. 51B illustrates a perspective view of the gastric band of FIG. 51A according to an embodiment of the present invention.

FIG. 51B illustrates a perspective view of the gastric band 5105 with the tapered body portion 5108. The inflatable portion 5110 and the other structures of the gastric banding system 5100 have been omitted for clarity. In this example, the tapered body portion 5108 may be a bar connecting the head 5104 (e.g., buckle) to a tail 5111 (e.g., belt) along a length of the ring 5107.

FIGS. 50A-50B and FIGS. 51A-51B merely illustrate examples of different gastric bands that may be utilized to customize the compliance performance curve. However, one skilled in the art will recognize that, while not shown, other embodiments may include additional cuts, breaks, and/or strategic layering using adhered or sliding surfaces to fine tune the compliance curve. In addition and/or alternatively, increasing the length of the ring (e.g., the ring 5007, 5107) may further tune the compliance curve.

The compliance, stiffness uniformity, or assembly strength of an overall gastric banding system may further be altered by varying the length, surface texture/topography, geography, taper of the end features (e.g., the area closest to the tail or buckle of the gastric band). Also, utilizing various assembly compositions, segments, portions or pieces of stiffer or softer material suspended in the band may adjust the resulting compliance of the overall band.

For instance, FIGS. 52A-52D illustrate four examples of tails or buckles of a gastric band with various over-molded interface features. Other portions of the gastric band such as the body of the ring (e.g., body 5108) and the head (e.g., head or belt 5111) have been omitted for clarity. However, any of the examples shown in FIGS. 52A-52D may be compatible with any of the gastric bands described herein or known in the art.

Figure 52A:
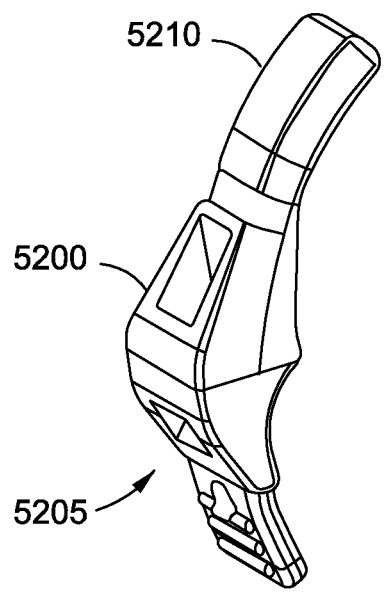
FIG. 52A illustrates a close-up perspective view of a belt of a gastric band according to an embodiment of the present invention.

FIG. 52A illustrates a buckle or a tail 5200 having an insertion portion 5205 to receive a belt or head (not shown). In addition, the tail 5200 may include an interface 5210 for attaching to the body of the ring (not shown). Here, the interface 5210 is shown to be substantially uniform in shape having four substantially similar smooth faces.

Figure 52B:
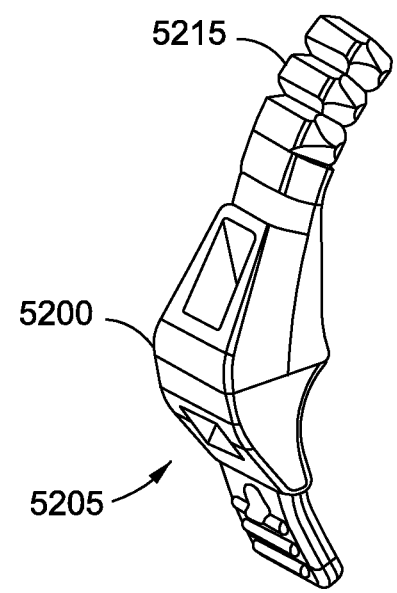
FIG. 52B illustrates a close-up perspective view of a belt of a gastric band according to an embodiment of the present invention.

FIG. 52B also illustrates the buckle or tail 5200 having the insertion portion 5205, but attached to an interface 5215. Here, the interface 5215 has many cut-out portions on a surface substantially parallel to the insertion portion 5205 while having pyramid-shaped protrusions along a surface substantially orthogonal to the insertion portion 5205. As compared to FIG. 52A, the more complex surface topography as embodied in the cut-out portions on the interface 5215 of FIG. 52B may increase the compliance of the tail 5200.

Figure 52C:
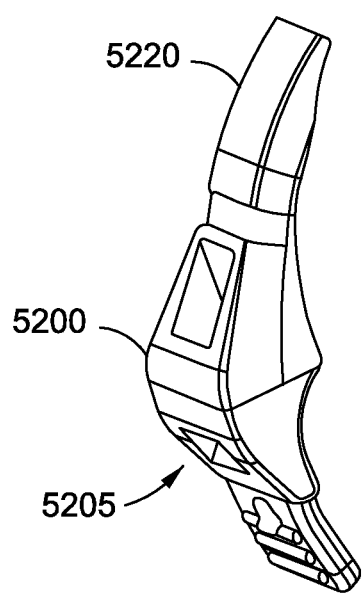
FIG. 52C illustrates a close-up perspective view of a belt of a gastric band according to an embodiment of the present invention.

FIG. 52C illustrates the buckle or tail 5200 having the insertion portion 5205, but attached to an interface 5220. The interface 5220 may be similar to the interface 5210 of FIG. 52A with one important distinction—namely that the interface 5220 tapers on one side as it extends away from the insertion portion 5205. The tapering may improve the compliance of the tail 5200.

Figure 52D:
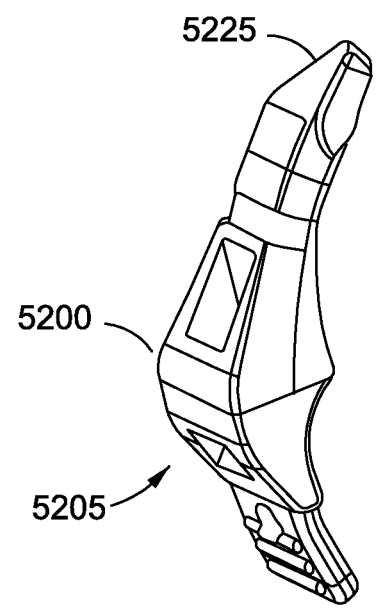
FIG. 52D illustrates a close-up perspective view of a belt of a gastric band according to an embodiment of the present invention.

FIG. 52D illustrates the buckle or tail 5200 having the insertion portion 5205, but attached to an interface 5225. The interface 5225 may be similar to the interface 5220 of FIG. 52C with one important distinction—namely that the interface 5225 tapers on multiple sides as it extends away from the insertion portion 5205. The additional tapering may further improve the compliance of the tail 5200.

Such examples serve to illustrate various degrees of compliance. Different patients may benefit from different gastric banding system compliances and these examples of ring variations may serve to fine tune the overall compliance of a gastric banding system to provide patients with a customizable compliance.

Figure 53A:
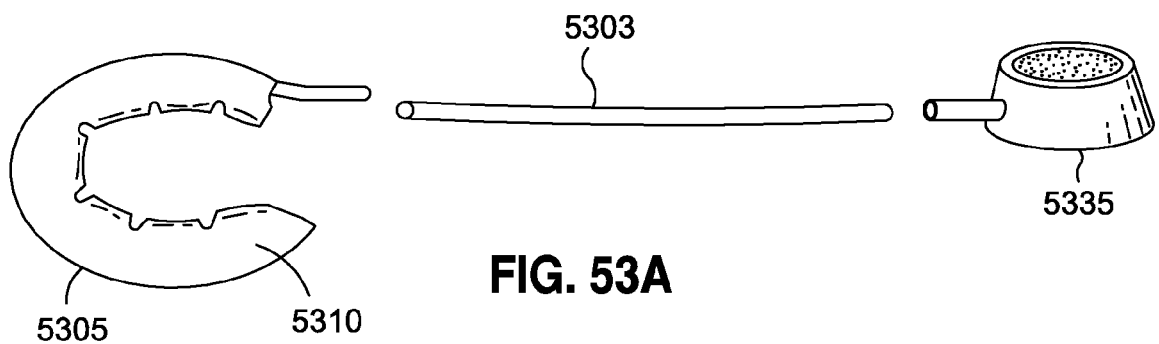
FIG. 53A illustrates an exploded, perspective view of a gastric banding system including a gastric band without a ring according an embodiment of the present invention.

FIG. 53A illustrates a dynamic ring gastric banding system 5300 which may include a gastric band 5305, a tube 5303 and an access port 5335. The gastric band 5305 may also include an inflatable portion 5310. The gastric band 5305 is obstruction-tolerant and may utilize non-fluid transfer means directly integrated into the gastric band itself. More particularly, the inflatable portion 5310 may be filled with a highly compliant, easily compressible or incompressible material medium. For example, the material fill may be incompressible, yet highly compliant and elastic (e.g., a gel) or compressible and non-elastic (e.g., a foam or mesh matrix).

Figure 53B:
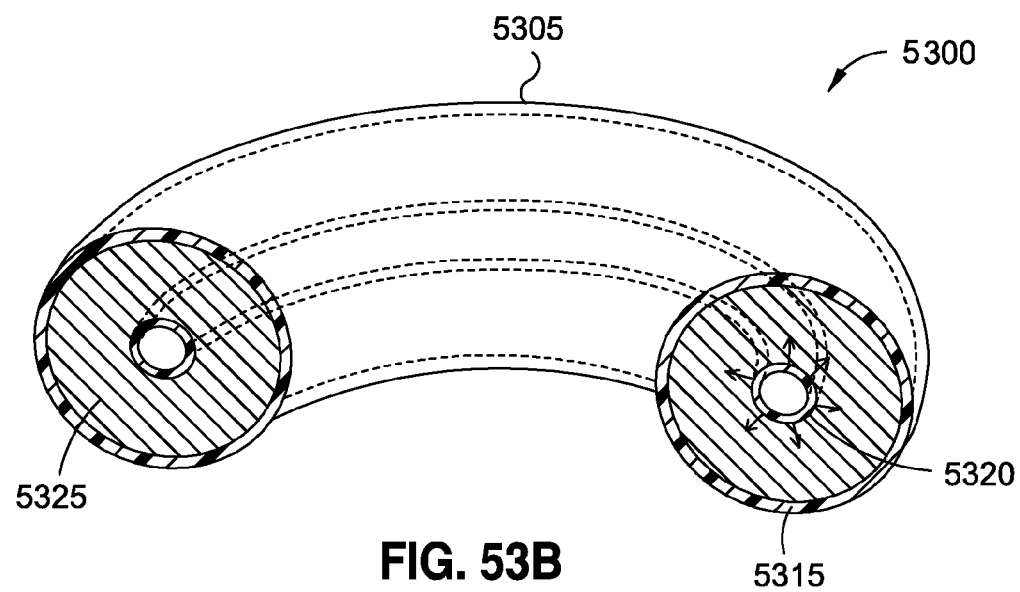
FIG. 53B illustrates a perspective, cross-sectional view of the gastric band of FIG. 53A according to an embodiment of the present invention.

FIG. 53B illustrates a cross-sectional view of the gastric band 5305 of FIG. 53A. As shown, the gastric band 5305 may include an outer shell 5315, a compliant core tubing 5320 in fluid communication with the rest of the gastric banding system 5300 (as shown in FIG. 53A). The compliant core tubing 5320 may be an inner tubing having a particular length and diameter. The outer shell 5315 may span (or be disposed about) the length of the compliant core tubing 5320 and may have a diameter greater than the diameter of the compliant core tubing 5320. The compliant core tubing 5320 may be surrounded by a material medium 5325 such as a gel, foam or mesh matrix.

The compliant core tubing 5320 may be a fluid lumen for saline injection and may expand when filled with increased volumes of saline. In one embodiment, when the compliant core tubing 5320 expands with saline, the material medium 5325 may be compressed, causing the gastric band to be less compliant and less tolerant to obstruction. By adjusting the saline or fluid fill, the compliance of the gastric band may be controlled.

By utilizing gel or other fill materials, the compressibility and compliance within the gastric band 5305 may be promoted. For example, where the inflatable portion of the gastric band 5305 is fixed at a maximum volume, the gel provides compressibility within that volume via the material properties of the gel. Accordingly, when a bolus of food passes through the constriction of the gastric band 5305, the gel may compress itself into the available volume within the gastric band 5305. The compliant core tubing 5320 which runs through the gel medium and is also contained within the inflatable portion of the gastric band 5305, acts as a medium by which an incompressible fluid (e.g., saline) when filled in the compliant core tubing 5320, occupies some of the inflatable volume. By occupying more of the inflatable volume, the compressible fill material has less volume to compress. Furthermore, the compliant core tubing 5320 allows adjustments via saline injection/removal such that when more saline is injected, the more volume within the band is occupied, leaving less volume for the compressible medium to act when a bolus passes through the constriction, thus increasing the sense of restriction.

This embodiment allows for dynamic resistance to be built directly into the basic frame and structure of existing gastric band technology. Furthermore, this embodiment is passive and the dynamic resistance may be inherent to the material properties of the design. Also, such an embodiment provides the benefit of reducing the need for additional chambers, external reservoirs or fluid flow between the chambers and/or reservoirs.

Figure 54A:
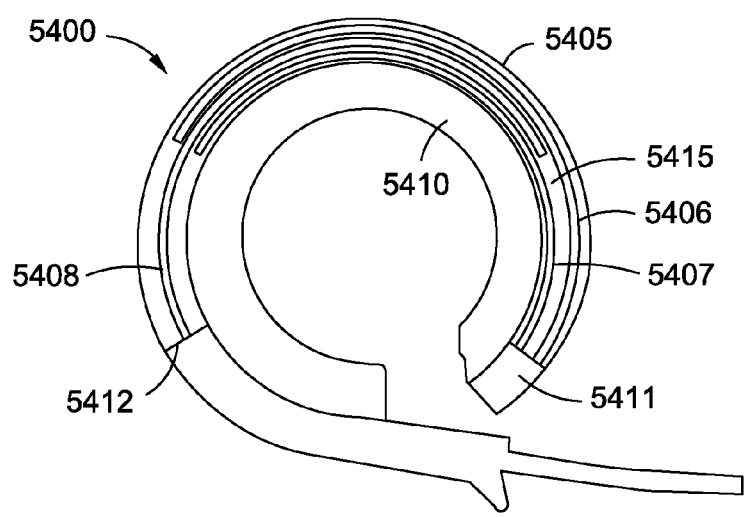
FIG. 54A illustrates a cross sectional view of a gastric band according an embodiment of the present invention.

FIG. 54A illustrates a gastric band 5400 which may include a ring 5405 having tubes, rods or strips 5406, 5407 and 5408 constructed out of any of a plurality of materials such as metals, polymers, and the like. These tubes, rods or strips 5406, 5407 and 5408 may be immersed in viscous fluid within a chamber 5415 located on the outside of a fluid reservoir 5410, which may be in fluid communication with other portions of the gastric banding system. Some other portions of the gastric banding system have been removed for clarity. As shown, the ring 5405 primarily includes the chamber 5415 which has a first and second tube, rod or strip 5406 and 5407 attached to a first end 5411 of the ring 5405, while the third tube, rod or strip 5408 is attached to the second end 5412 of the ring 5405 and located proximally between the first and second tube, rod or strip 5406 and 5407. By immersing these structures (e.g., the first, second and third tube, rod or strips 5405, 5406 and 5407) in viscous fluid, unique physical characteristics such as speed limiters and viscosity effects that manipulate the movement and forcing characteristics of the gastric band 5400 when under load may be obtained. Generally, when a large load is applied, the fluid and the tubes, rods or strips 5406, 5407, 5408 work to strongly resist, and when the load is small, the fluid and the tubes, rods or strips 5406, 5407, 5408 do not provide much resistance. Certain examples of fluids which may be used include but are not limited to thixotropic, viscoelastic and Bingham-type fluids.

Figure 54B:
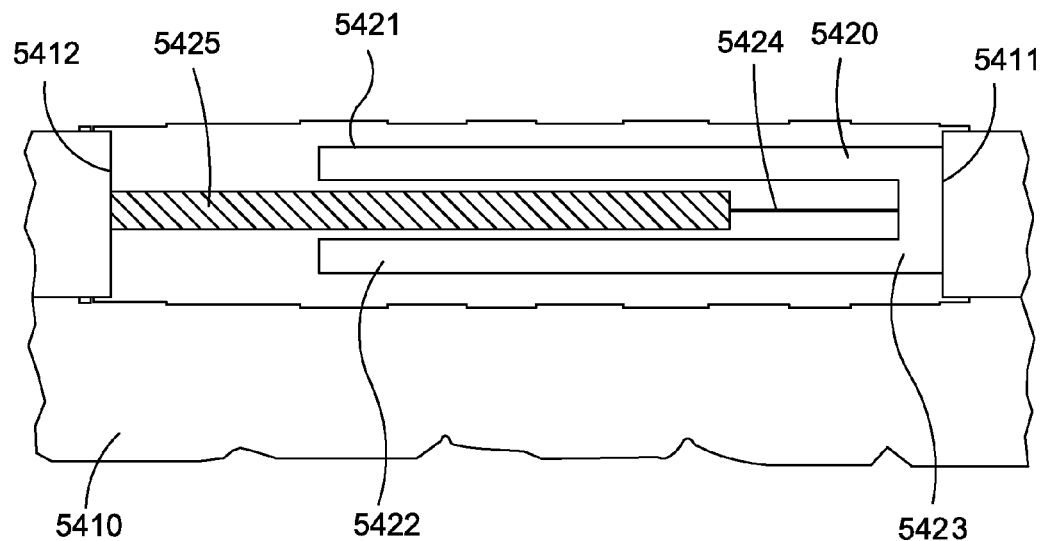
FIG. 54B illustrates a close-up, cross-sectional view of the gastric band of FIG. 54A according to an embodiment of the present invention.

FIG. 54B illustrates a close-up view with an alternative structure. Here, between the first end 5411 and the second end 5412 of the ring 5405 exists a chamber 5415 filled with viscous fluid and a first tube, rod or strip 5420 and a second tube, rod or strip 5425. The first tube, rod or strip 5420 may include a first portion 5421, a second portion 5422 and a joining portion 5423 which joins the first portion 5421 to the second portion 5422 and also attaches the first tube, rod or strip 5420 to the first end 5411 of the ring. The second tube, rod or strip 5425 may be attached to the second end 5412 of the ring 5405 and may be positioned between the first portion 5421 and the second portion 5422 of the first tube, rod or strip 5420. The second tube, rod or strip 5425 may also be attached to the joining portion 5423 of the first tube, rod or strip 5420 via a spring, band or string 5424. In this manner, when a load is applied (e.g., a bolus passing through the constriction formed by the ring 5405), the first tube, rod or strip 5420 may be pulled away from the second tube, rod or strip 5423 but still remain tethered by the stretched ring, band or string 5424. Similar to the configuration of FIG. 54A, the structural configuration of FIG. 54B provides a system which acts to strongly resist displacement (temporarily) when a large load is applied, and to easily displace when the load is small.

FIGS. 55-58 illustrate additional alternative embodiments of how the ring portion (e.g., ring 5405) may be modified to strongly resist displacement (temporarily) when a large load is applied, and to easily displace when the load is small. More particularly, a damping mechanism may be employed to resist displacement when a load greater than a predetermined threshold is applied, and to not resist displacement when a load smaller than a predetermined threshold is applied.

Figure 55:
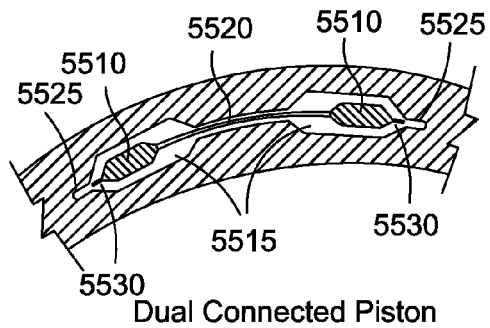
FIG. 55 illustrates a gastric band featuring dual connected pistons according to an embodiment of the present invention.

For example, as shown in FIG. 55, dual connected pistons 5510 may be utilized to achieve the desired characteristics. The pistons 5510 may be located in their respective orifices 5515, and immersed with thixotropic, viscoelastic and/or Bingham-type fluids. The pistons 5510 may be tethered to one another by a connecting band 5520. The pistons 5510 are respectively fixed to an anchor point 5525 via springs 5530. As shown, the orifices 5515 may be cavities formed within the ring 5505 via, for example, molding. The size of the orifices 5515 (e.g., length) and the distance between the orifices 5515 may define the compliance of the ring 5505. As a bolus engages the constriction and applies a load to the ring 5505, the pistons 5510 may move away from one another and migrate from the proximal end of the orifices 5515 to the distal end of the orifices 5515. However, the pistons 5510 may limit the ring 5505 from further expansion when they press against the distal end of the orifices 5515. As the bolus passes through the constriction, the pistons 5510 may move back towards one another.

Figure 56:
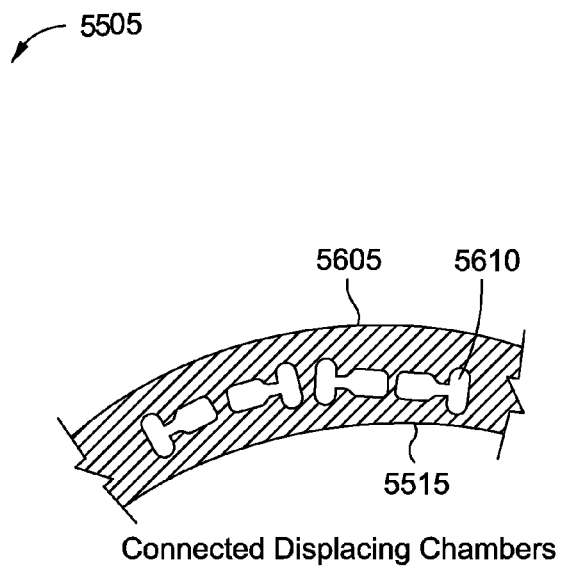
FIG. 56 illustrates a gastric band featuring connected displacing chambers according to an embodiment of the present invention.

FIG. 56 illustrates a plurality of distinct sets of connected displacing chambers 5610 within a ring 5605. The chambers 5610 may be filled with thixotropic, viscoelastic and/or Bingham-type fluids. As a bolus engages the constriction and applies a load to the ring 5605, the fluid characteristics may cause the ring 5605 to strongly resist displacement (temporarily) when a large load is applied, and to easily displace when the load is small.

Figure 57:
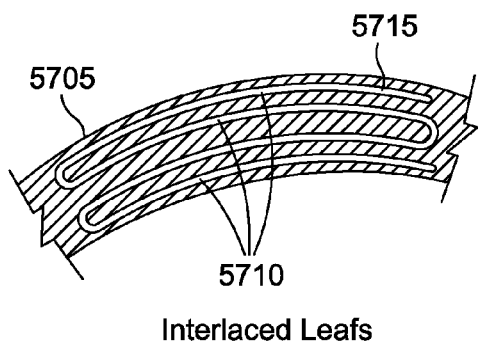
FIG. 57 illustrates a gastric band featuring interlaced leaves according to an embodiment of the present invention.

FIG. 57 illustrates interlaced leaves 5710 immersed within thixotropic, viscoelastic and/or Bingham-type fluids. As a bolus engages the constriction and applies a load to a ring 5705, the fluid characteristics may cause the ring 5705 to strongly resist displacement (temporarily) when a large load is applied, and to easily displace when the load is small.

Figure 58:
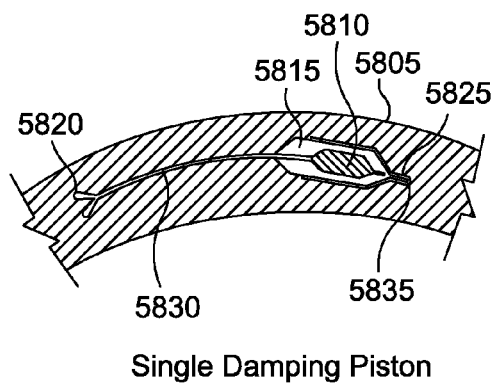
FIG. 58 illustrates a gastric band featuring a single damping piston according to an embodiment of the present invention.

FIG. 58 illustrates a single damping piston. The piston 5810 may be tethered to anchor points 5820 and 5825 on opposite sides of an orifice 5815 housing the piston 5820 by connecting bands 5830 and 5835. The connecting bands 5830 and 5835 may have different (e.g., opposite) tension such that when a load is applied, the band 5830 may displace in one manner (shorten) while the band 5835 displaces in another manner (lengthens) thereby causing the piston 5820 to move from one end of the orifice 5815 to the other end of the orifice 5815. As shown, the orifice 5815 may be a cavity formed within a ring 5805 via, for example, molding. The size of the orifice 5815 (e.g., length) along with the tension of the connecting bands 5830 and 5835 may define the compliance of the ring 5805. The orifice 5810 may also be filled with a thixotropic, viscoelastic and/or Bingham-type fluid which may have fluid characteristics causing the ring 5505 to strongly resist displacement (temporarily) when a large load is applied, and to easily displace when the load is small.

While other structural configurations are possible to provide the effects described above, certain embodiments have been disclosed to clarify the concepts.

Other methods for dialing in gastric band performance curves and characteristics include utilizing force threshold mechanisms such as release hooks or magnets that release under a specific increased load. This may allow the gastric band to expand quickly after the limit load is reached. After the load and subsequent expansion passes, the stressed structure of the gastric band brings the load limit device back together in a closed, set configuration for operation under normal loads. This device will then remain closed, providing normal restriction and compliance until a load greater than a predetermined threshold is reached. This concept is intended to maintain the normal operating performance of the gastric band while adding a security feature to temporarily loosen the gastric band under extreme loading conditions to prevent patient injury. By varying the number, size and strength of the magnets as well as the allowable magnet separation when expanded and characteristics of the surrounding structural geometry, the resulting performance curves may be customized.

Figure 59A:
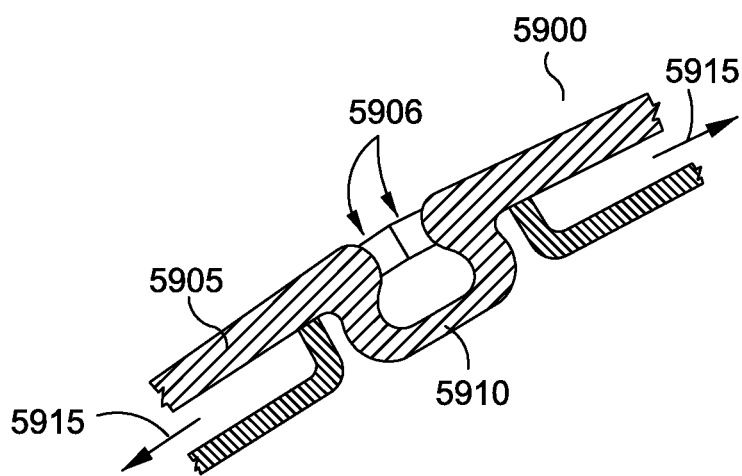
FIG. 59A illustrates a gastric band featuring a force limit release device in a closed position according to an embodiment of the present invention.
Figure 59B:
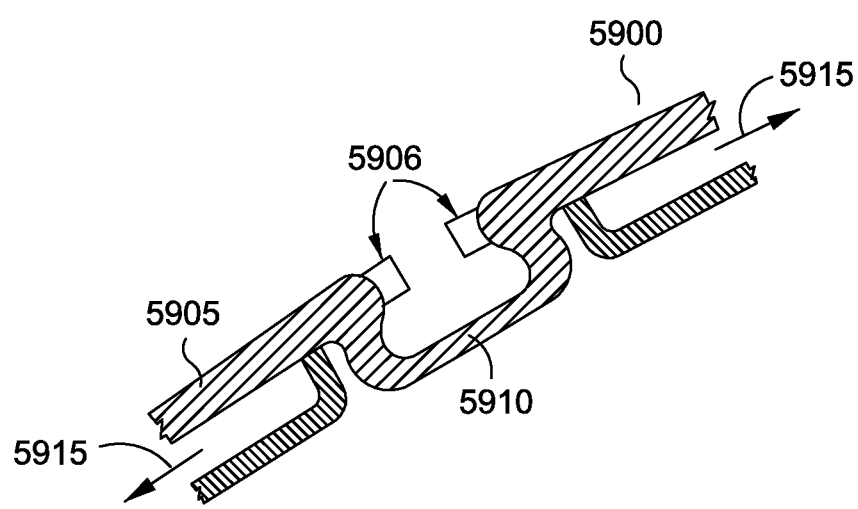
FIG. 59B illustrates a gastric band featuring a force limit release device in an open position according to an embodiment of the present invention.

FIGS. 59A and 59B illustrate a load limit device 5906 integrated into a ring 5905 of a gastric band 5900. FIG. 59A illustrates the load limit device 5906 in a first state (closed). Here, the load limit device 5906 may be a pair of magnets which are attracted to and in contact with one another. The load limit device 5906 may be positioned opposite to the structural member 5910. When a load (e.g., caused by a bolus passing through the constriction of the gastric band 5900) is applied in the direction of arrows 5915 great enough to separate the load limit device 5906, the magnets of the load limit device 5906 may release from one another, thereby expanding the ring 5905 under excess load to allow the bolus to pass through. FIG. 59B illustrates the ring 5905 when the load limit device 5906 is separated under an excess load. Once the bolus passes through, the structural member 5910 (which may be loaded under expansion) may return the load limit device 5906 back together and return the ring 5905 back to the configuration as shown in FIG. 59A. The structural member 5910 may be preloaded in tension or compression while the load limit device 5906 is in the closed position of FIG. 59A to help customize the resulting performance characteristic.

As shown in FIGS. 59A and 59B, the load limit device 5906 includes magnets. However, release hooks or other components which are capable of releasing upon introduction of a load and reengaging after the passage of the load may be utilized in addition or in place of the magnets.

In further embodiments, features may be added to a gastric band in order to limit the maximum expansion that can be obtained under high loads (e.g., a load greater than a predetermined threshold). These features may be configured to work in conjunction with the elastomeric backbone of the gastric band to limit the increased stretch that might occur in certain gastric band designs, thereby allowing for a region of linear elastic expansion with a tunable maximum expansion that prevents over expansion and/or material failure. For example, a stretch limiter may be a conformally flexible but inelastic component that may take the form of a wire, monofilament or strap. Additionally and/or alternatively, the stretch limiter may be a structural, biocompatible material such as titanium wire, polypropylene filament, Teflon, titanium, very high strength and modulus silicone and/or any other appropriate material.

Figure 60:
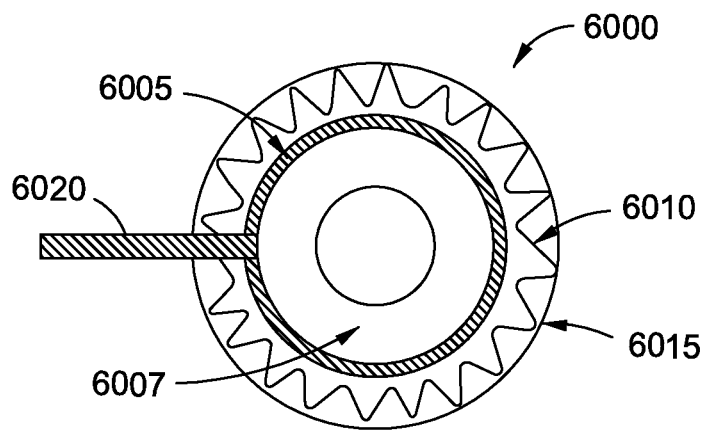
FIG. 60 illustrates a gastric band featuring an encapsulated stretch limiter according to an embodiment of the present invention.

FIG. 60 illustrates an example of features which may limit the maximum expansion of a gastric band 6000. As shown, the gastric band 6000 may include standard components such as a ring 6005 surrounding the inflatable portion 6007 which is in fluid communication with the rest of the gastric banding system (not shown) via the tubing 6020. In addition, the gastric band 6000 may include a stretch limiter 6010 and a protective capsule 6015. The stretch limiter 6010 may be encapsulated in a chamber adjacent to the ring 6005 of the gastric band 6000, and may be made from material and processes similar to the over-molded reservoir of the typical gastric band. Here, the protective capsule 6015 may be separated from the reservoir 6007 and collapsed/evacuated over the stretch limiter 6010. With the gastric band 6000 in a relaxed state, the stretch limiter 6010 may be loose with a predetermined amount of slack. As the gastric band 6000 becomes over-expanded, the stretch limiter 6010 may extend outwards and when fully extended, may contact the inner wall of the protective capsule 6015, and prevent further expansion.

Figure 61:
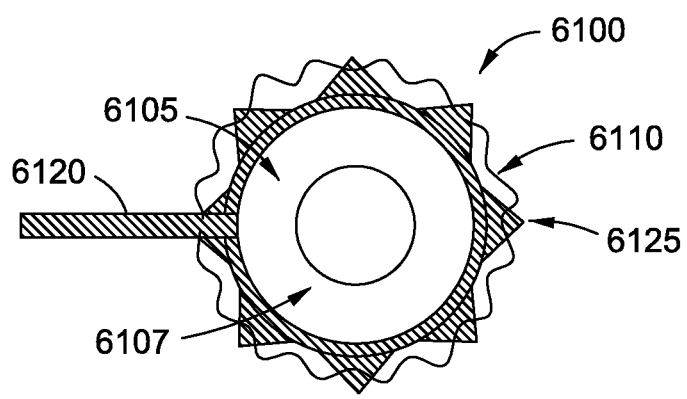
FIG. 61 illustrates a gastric band featuring an external stretch limiter according to an embodiment of the present invention.

FIG. 61 illustrates another embodiment of a gastric band 6100 having a stretch limiter 6110. Here, the stretch limiter 6110 may be attached or laced through limiter guides 6125 on the outer side of the elastomeric ring 6105. In other words, the tip of the limiter guides 6125 may extend beyond the stretch limiter 6110 via holes, cuts or slits on the stretch limiter 6110 which may be formed via molding. As the inflatable portion 6107 expands, the limiter guides 6125 may press and stretch against the stretch limiter 6110, thereby increasing tension. However, the stretch limiter 6110, when expanded to a certain predetermined threshold, may prevent further expansion of the inflatable portion 6107. In this manner, the overall system may function very similarly to the gastric band 6000 of FIG. 60.

Figure 62:
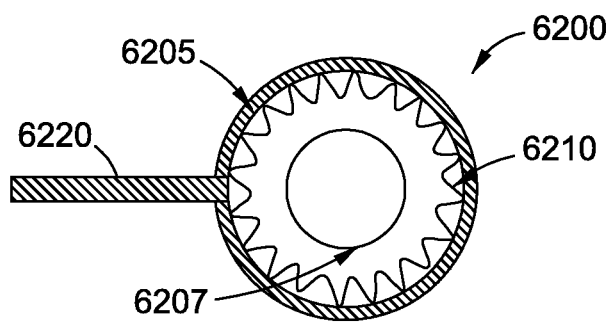
FIG. 62 illustrates a gastric band featuring an internal stretch limiter according to an embodiment of the present invention.

FIG. 62 illustrates yet another example of a gastric band 6200 having a stretch limiter 6210. Here, the stretch limiter 6210 may be disposed inside the inflatable portion 6207 and as fluid volume increases within the inflatable portion 6207, the stretch limiter 6210 may expand to contact the outer wall of the inflatable portion 6207. In this example, the stretch limiter 6210 may have a very high modulus elastomer that is flexible enough to be loose and with slack inside the inflatable portion 6207. When fully extended, the stretch limiter 6210 may prevent further expansion of the inflatable portion 6107. The stretch limiter 6210 may also be sufficiently wide and round as to not adversely affect the structures pressed against it.

The embodiments described with respect to FIGS. 60-62 may be as shown (extending about substantially the entire circumference of the gastric band) or may be limited to only a portion designated as an elastic region. The elastic region would then serve as a pressure relief or regulator for the gastric band and the stretch limiters utilized therein would ensure the structural integrity of the elastic region.

Furthermore, although various compliant components are illustrated in one or more of the figures, it should be understood that any combination of the various compliant components may be utilized in different embodiments. For example, an embodiment may include one compliant component (e.g., only the ring, the tubing, or the access port may be compliant). In other embodiments, any combination of the ring, the tubing, and the access port may be compliant. For example, an embodiment may include a compliant ring and a compliant port, an embodiment may include compliant tubing and a compliant port, or an embodiment may include a compliant ring and compliant tubing. Any combination of compliant components is within the scope of the present invention.

Unless otherwise indicated, all numbers expressing quantities of ingredients, volumes of fluids, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A self-adjusting gastric band system for the treatment of obesity that adjusts to allow a bolus to pass through a constriction in a patient's stomach, the self-adjusting gastric band system comprising:
   a gastric band having:
   i) an inflatable portion having an outer portion and an inner portion, the inner portion configured to be placed around a portion of the patient's stomach to thereby create the constriction in the patient's stomach, and
   ii) a ring attached to the outer portion of the inflatable portion of the gastric band, the ring having at least three segment portions, the ring defining a thickness in a radial direction when the gastric band is configured banded about the portion of the patient's stomach, wherein each segmented portion includes a through-hole extending through the thickness of the ring, and at least a plurality of the through-holes are aligned in the radial direction with the outer portion of the inflatable portion of the gastric band, and wherein when the band is banded a common plane extends through the inflatable portion and the at least three through-holes;
   an access port fluidly coupled to the inflatable portion of the gastric band to fill and drain a fluid into or out of the inflatable portion; and
   a compliant reservoir fluidly coupled to the inflatable portion and the access port, the compliant reservoir capable of relaxing the constriction formed in the stomach by the gastric band by receiving fluid from the inflatable portion thereby allowing the bolus to pass through the relaxed constriction.

2. The self-adjusting gastric band system of claim 1 wherein the through-hole is diamond-shaped.

3. The self-adjusting gastric band system of claim 2 wherein the segmented portions are inwardly-tapered.

4. The self-adjusting gastric band system of claim 1 wherein the ring further comprises:
   a belt attached to a first end of the ring; and
   a buckle attached to the second end of the ring configured to receive and secure the belt.

5. The self-adjusting gastric band system of claim 1, wherein all of the through-holes are situated over the inflatable portion of the gastric band.

6. The self-adjusting gastric band system of claim 1, wherein at least one of the through-holes is situated radially adjacent to the inflatable portion of the gastric band.

7. The self-adjusting gastric band system of claim 1, wherein at least one of the through-holes is situated oppositely facing the inflatable portion of the gastric band.

* * * * *